US009238669B2

(12) United States Patent
Seeberger et al.

(10) Patent No.: US 9,238,669 B2
(45) Date of Patent: Jan. 19, 2016

(54) OLIGOSACCHARIDES AND OLIGOSACCHARIDE-PROTEIN CONJUGATES DERIVED FROM *CLOSTRIDIUM DIFFICILE* POLYSACCHARIDE PS-I, METHODS OF SYNTHESIS AND USES THEREOF, IN PARTICULAR AS VACCINES AND DIAGNOSTIC TOOLS

(75) Inventors: Peter H. Seeberger, Kleinmachnow (DE); Christopher E. Martin, Berlin (DE); Felix Broecker, Berlin (DE); Chakkumkal Anish, Berlin (DE)

(73) Assignee: Max-Planck-Gesellschaft zur Foerderung der Wissenschaften e. V., Munich (DE)

( * ) Notice: Subject to any disclaimer, the term of this patent is extended or adjusted under 35 U.S.C. 154(b) by 11 days.

(21) Appl. No.: 14/236,620

(22) PCT Filed: Jul. 30, 2012

(86) PCT No.: PCT/EP2012/003240
§ 371 (c)(1),
(2), (4) Date: Mar. 18, 2014

(87) PCT Pub. No.: WO2013/017254
PCT Pub. Date: Feb. 7, 2013

(65) Prior Publication Data
US 2014/0193416 A1 Jul. 10, 2014

Related U.S. Application Data

(60) Provisional application No. 61/514,095, filed on Aug. 2, 2011.

(30) Foreign Application Priority Data

Aug. 2, 2011 (EP) .................... 11006355

(51) Int. Cl.
*C07H 15/04* (2006.01)
*C07H 3/06* (2006.01)
*C07H 5/04* (2006.01)
*C07H 3/08* (2006.01)
*C07H 13/08* (2006.01)
*C07H 15/20* (2006.01)
*C07K 16/12* (2006.01)
*G01N 33/569* (2006.01)

(52) U.S. Cl.
CPC .. *C07H 3/06* (2013.01); *C07H 3/08* (2013.01); *C07H 5/04* (2013.01); *C07H 13/08* (2013.01); *C07H 15/04* (2013.01); *C07H 15/20* (2013.01); *C07K 16/1282* (2013.01); *G01N 33/56911* (2013.01)

(58) Field of Classification Search
None
See application file for complete search history.

(56) References Cited

FOREIGN PATENT DOCUMENTS

WO 2009033268 A1 3/2009

OTHER PUBLICATIONS

Ada et al., "Carbohydrate-protein conjugate vaccines", Clin. Microbiol. Infect., vol. 9, pp. 79-85 (2003).
Astronomo et al., "Carbohydrate vaccines: developing sweet solutions to sticky situations?", Nature Rev., vol. 9, pp. 308-324 (2010).
Collot et al., "New thioglycoside derivatives for use in odourless synthesis of MUXF3 N-glycan fragments related to food allergens", Tetrahedron, vol. 64, pp. 1523-1535 (2008).
Danieli et al., "First Synthesis of *C. difficile* PS-II Cell Wall Polysaccharide Repeating Unit", Organic Letters., vol. 13, No. 3, pp. 378-381 (2011).
Danishefsky et al., "A Highly Convergent Total Synthetic Route to Glycopeptides Carrying a High-Mannose Core Pentasaccharide Domain N-linked to a Natural Peptide Motif", Chem. Eur. J., vol. 3, No. 10, pp. 1617-1628 (1997).
Delcros et al., "Effect of Spermine Conjugation on the Cytotoxicity and Cellular Transport of Acridine", J. Med. Chem., vol. 45, pp. 5098-5111 (2002).
Dubois et al. "Chemical Approaches to Baterial Vaccines, Synthesis of Mycrobacterial Oligosaccharide• Protein Conjugates for Use as Serodiagnostics and Immunogens", Bioorganic & Medicinal Chemistry Letters, vol. 6, No. 12, pp. 1387-1392 (1996).
Ganeshapillai et al. "*Clostridium difficile* cell• surface polysaccharides composed of pentaglycosyl and hexaglycosyl phosphate repeating units", Carbohydrate Research, 343, pp. 703-710 (2008).
Hecht et al., "Recent advances in carbohydrate-based vaccines", Curr. Opin. Chem. Biol., vol. 13, pp. 354-359 (2009).
Koehler et al, "Continuous cultures of fused cells secreting antibody of predefined specificity", Nature, vol. 256, pp. 495-497 (1975).
Lee et al., "The potential value of *Clostridium difficile* vaccine: An economic computer simulation model", Vaccine, vol. 28, pp. 5245-5253 (2010).
Leyva et al., "Rapid and sensitive anthrone—sulfuric acid assay in microplate format to quantify carbohydrate in biopharmaceutical products: Method development and validation", Biologicals, vol. 36, pp. 134-141 (2008).

(Continued)

*Primary Examiner* — Eric Olson
(74) *Attorney, Agent, or Firm* — Caesar Rivise, PC

(57) ABSTRACT

The invention relates to a synthetic oligosaccharide representing part of the repeating unit of the *Clostridium difficile* glycopolymer PS-I and having the sequence of the pentasaccharide a-L-Rhap-(1→3)-β-D-Glcp-(1→4)-[a-L-Rhap-(1→3]-a-D-Glcp-(1→2)-a-D-Glcp or a synthetic fragment or derivative thereof. Preferably, the claimed synthetic oligosaccharide bears at least one linker L for conjugation to a carrier protein or for immobilization on a surface. Further aspects of the invention relate to advantageous methods for synthesizing said synthetic oligosaccharide and oligosaccharide-protein conjugate as well as to uses thereof, in particular as vaccines and diagnostic tools.

2 Claims, 8 Drawing Sheets

(56) References Cited

OTHER PUBLICATIONS

Figure 1:
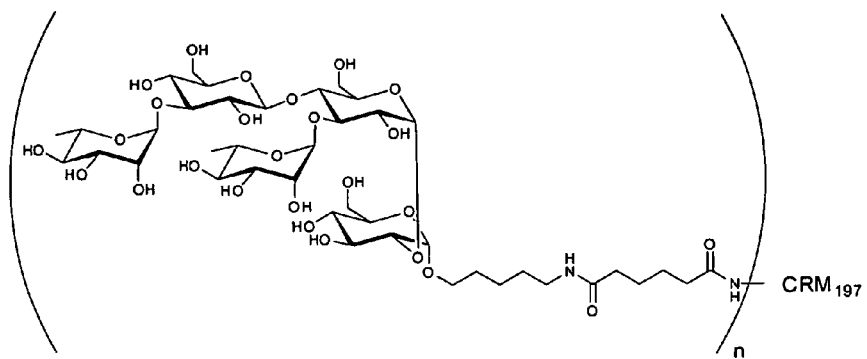

Liu et al., "A Suzuki-Miyaura coupling mediated deprotection as key to the synthesis of a fully lapidated malarial GPI disaccharide", Chem. Commun., pp. 1708-1709 (2004).

Love et al., "Automated Solid-Phase Synthesis of Protected Tumor-Associated Antigen and Blood Group Determinant Oligosaccharides", Angew. Chem. Int. Ed., vol. 43, pp. 602-605 (2004).

Milhomme et al. "Access to Antigens Related to Anthrose Using Pivotal Cyclic Sulfite/Sulfate Intermediates", The Journal of Organic Chemistry, vol. 76, pp. 5985-5998 (2011).

Nicolaou et al., "A General and Highly Efficient Solid Phase Synthesis of Oligosaccharides. Total Synthesis of a Heptasaccharide Phytoalexin Elicitor (HPE)", J. Am. Chem. Soc., vol. 119, pp. 449-450 (1997).

Oberli et al. "A Possible Oligosaccharide-Conjugate Vaccine Candidate for *Clostridium difficile* is Antigenic and Immunogenic", Chemistry & Biology, vol. 18, pp. 580-588 (2011).

Plante et al., "Halobenzyl Ethers as Protecting Groups for Organic Synthesis", J. Am. Chem. Soc., vol. 122, pp. 7148-7149 (2000).

Rountree et al., "Synthesis of a Novel Polyhydroxylated Salicylic Acid Lactone Framework", Organic Letters, vol. 11, No. 4, pp. 871-874 (2009).

Snapper et al., "A Model for Induction of T Cell-Independent Humoral Immunity in Response to Polysaccharide Antigens", J. Immunol., vol. 157, pp. 2229 (1996).

Werz et al., "Synthesis of a Spore Surface Pentasaccharide of *Bacillus anthracis*", Eur. J. Org. Chem., vol. 12, pp. 1976-1982 (2007).

Xia et al., "Use of 1,2-dichloro4,5-dicyanoquinone (DDQ) for cleavage of the 2-naphthylmethyl (NAP) group", Tetrahedron Letters, vol. 41, pp. 169-173 (2000).

Yu et al., "Glycosyl trifluoroacetimidates. Part 1: Preparation and application as new glycosyl donors", Tetrahedron Letters, vol. 42, pp. 2405-2407 (2001).

Zhang et al. "Linking Carbohydrates to Proteins Using N-(2,2-Dimethoxyethyl)-6-hydroxy Hexanamide", Tetrahedron, vol. 54, pp. 11783-11792 (1998).

International Search Report for PCT/EP2012/003240 dated Sep. 11, 2012.

Conjugate 1: MS (MALDI-TOF)

Conjugate 1: HPLC (blue $t_R$= 22.49 min, overlaid with unconjugated $CRM_{197}$ standard red $t_R$= 22.86 min)

Conjugate 1: SDS-PAGE (Lanes: 1: molecular weight marker (Invitrogen bench marker); 2: unconjugated $CRM_{197}$ standard; 3, 4, 5: conjugate 1)

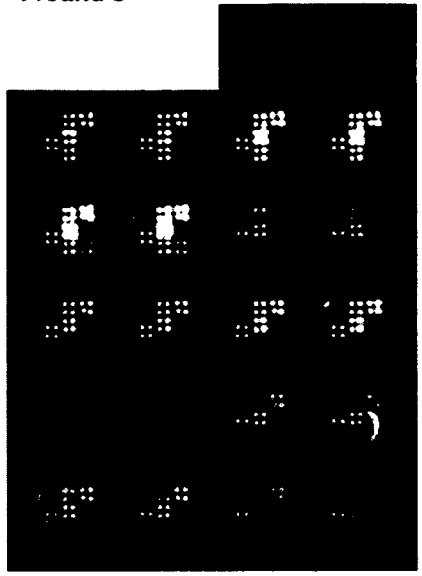

| | | prebleed 1:50 | prebleed 1:50 |
|---|---|---|---|
| primed 1:50 | primed 1:50 | boosted (week 3) 1:50 | boosted (week 3) 1:50 |
| boosted (week 5) 1:50 | boosted (week 5) 1:50 | primed 1:250 | primed 1:250 |
| boosted (week 3) 1:250 | boosted (week 3) 1:250 | boosted (week 5) 1:250 | boosted (week 5) 1:250 |
| primed 1:1000 | primed 1:1000 | boosted (week 3) 1:1000 | boosted (week 3) 1:1000 |
| boosted (week 5) 1:1000 | boosted (week 5) 1:1000 | boosted (week 5) 1:2000 | boosted (week 5) 1:2000 |

Fig. 11

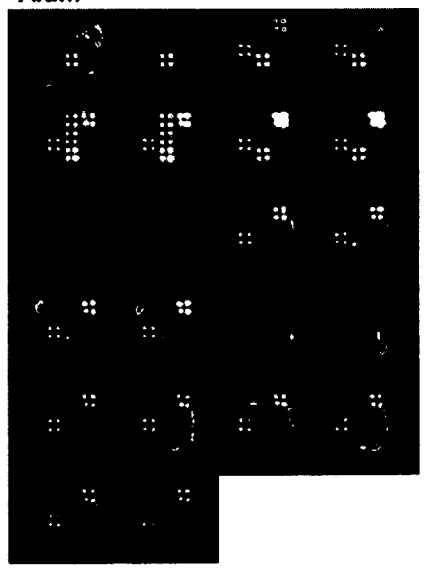

| prebleed 1:50 | prebleed 1:50 | primed 1:50 | primed 1:50 |
|---|---|---|---|
| boosted (week 3) 1:50 | boosted (week 3) 1:50 | boosted (week 5) 1:50 | boosted (week 5) 1:50 |
| primed 1:250 | primed 1:250 | boosted (week 3) 1:250 | boosted (week 3) 1:250 |
| boosted (week 5) 1:250 | boosted (week 5) 1:250 | primed 1:1000 | primed 1:1000 |
| boosted (week 3) 1:1000 | boosted (week 3) 1:1000 | boosted (week 5) 1:1000 | boosted (week 5) 1:1000 |
| boosted (week 5) 1:2000 | boosted (week 5) 1:2000 | | |

Fig. 12

OLIGOSACCHARIDES AND OLIGOSACCHARIDE-PROTEIN CONJUGATES DERIVED FROM *CLOSTRIDIUM DIFFICILE* POLYSACCHARIDE PS-I, METHODS OF SYNTHESIS AND USES THEREOF, IN PARTICULAR AS VACCINES AND DIAGNOSTIC TOOLS

BACKGROUND

*Clostridium difficile* is a Gram-positive, spore forming anaerobic bacterium that colonizes the intestinal tract of humans thus leading to *C. difficile* infections (CDI). CDI has become the most commonly diagnosed cause of hospital-acquired diarrhea, particularly in the risk groups including elderly and immunodeficient patients as well as those receiving antibiotic treatment. A steep rise in CDI incidents over the past decade is attributed to the emergence of the hypervirulent, and now predominant strain ribotype 27, causing epidemic outbreaks with increased morbidity, mortality and high relapse rates. The costs to treat patients have greatly increased, particularly in the case of recurring CDI. Preventive methods, such as vaccination of risk groups, may be useful and cost-efficient means to avoid future infections. Although vaccination against *C. difficile* should be economically feasible (B. Y. Lee et al., *Vaccine*, 2010, 28, 5245) a vaccine has not yet been developed.

Carbohydrates exposed on the cell-surface of pathogens are often immunogenic and constitute potential candidates for vaccine development. When covalently connected to carrier proteins, carbohydrate antigen vaccines can elicit a long lasting T-cell dependent protection (C. Snapper and J. Mond, *J. Immunol.*, 1996, 157, 2229). Several vaccines containing carbohydrates, isolated from biological sources, are in routine use (G. Ada and D. Isaacs, *Clin. Microbiol. Infect.*, 2003, 9, 79). Vaccines based on synthetic carbohydrate antigens against bacteria, viruses, parasites and cancer are currently in preclinical and clinical development (a) R. D. Astronomo and D. R. Burton, *Nature Rev.*, 2010, 9, 308; b) M.-L. Hecht, P. Stallforth, D. V. Silva, A. Adibekian and P. H. Seeberger, *Curr. Opin. Chem. Biol.*, 2009, 13, 354).

The chemical structure of two *C. difficile* cell-surface polysaccharides, PS-I and PS-II has been elucidated recently (J. Ganeshapillai et al., *Carbohydr. Res.*, 2008, 343, 703; WO 2009/033268 A1). Initial focus has been turned towards the PS-II hexasaccharide antigen that is believed to be common to several *C. difficile* strains (a) E. Danieli et al., *Org. Lett.*, 2010, 13, 378; b) M. Oberli, M.-L. Hecht, P. Bindschädler, A. Adibekian, T. Adam and P. H. Seeberger, *Chem. Biol.*, 2011, 18, 580). The synthetic PS-II hapten is immunogenic when conjugated to a carrier protein and antibodies found in the stool of *C. difficile* patients bind to the synthetic PS-II hexasaccharide (Oberli et al., ibid.). The pentasaccharide phosphate repeating unit PS-I was reported as [→4)-α-Rhap-(1→3)-β-Glcp-(1→4)-[α-Rhap-(1→3)]-α-Glcp-(1→2)-α-Glcp-(1→P] and it is suggested to be specific for the strain ribotype 27.

In conclusion, the pathogen *C. difficile* represents a major risk for patients and causes significant costs to health care systems. Unfortunately, however, currently no licensed vaccine against *C. difficile* is available.

Thus, a main object of the present invention is to provide novel and effective means to prevent and/or to treat *C. difficile* associated diseases, in particular related to the hypervirulent strain ribotype 027. A further object is to provide novel and effective means to detect *C. difficile* in a sample and/or a *C. difficile* infection in a subject. A further object is to provide novel and effective means to identify a certain strain of *C. difficile* in a sample and/or a *C. difficile* infected subject. A further object is to provide novel and effective standards for immunoassays for the detection of *C. difficile*.

The present inventors succeeded in the first total synthesis of a pentasaccharide derived from the repeating unit of the *C. difficile* polysaccharide PS-I, and its conjugation to the diphtheria toxoid $Crm_{197}$.

Consequently, the above main object of the invention is achieved by providing the synthetic oligosaccharide, in particular pentasaccharide, the oligosaccharide-protein conjugate and the composition according to the invention. Further objects are achieved by providing the antibody, the methods of detection and identification, and the methods of synthesis according to the invention.

DESCRIPTION OF THE INVENTION

The present invention provides an oligosaccharide, in particular synthetic oligosaccharide, derived from the repeating unit of the *Clostridium difficile* glycopolymer PS-I and an oligosaccharide-protein conjugate comprising said oligosaccharide coupled to a protein carrier.

More specifically, the oligosaccharide is the pentasaccharide having the sequence α-L-Rhap-(1→3)-β-D-Glcp-(1→4)-[α-L-Rhap-(1→3]-α-D-Glcp-(1→2)-α-D-Glcp or a (synthetic) fragment or derivative thereof.

The term "derivative" as used herein means generally any structurally related molecule having the same scaffold as the basic molecule but which is modified by the addition, deletion or substitution of one or more functional groups. For example, the "oligosaccharide derivative" as used herein may be obtained by replacement of one or more of the hydroxyl groups by other functional groups or atoms or by introducing additional substituents such as linker groups.

The term "fragment" as used herein includes tetra-, tri-, di- and monosaccharides which are constituting units of the pentasaccharide having the sequence α-L-Rhap-(1→3)-α-D-Glcp-(1→4)-[α-L-Rhap-(1→3]-α-D-Glcp-(1→2)-α-D-Glcp from above or from a derivative thereof, in particular a derivative comprising one or more linker group(s).

Preferably, the oligosaccharide bears at least one linker L for conjugation to a carrier protein or for immobilization on a surface.

The linker or spacer group L may be any moiety that enables to couple the oligosaccharide to a carrier molecule or to the surface of a microarray. A large variety of such linker groups are known in the art and a suitable linker group can be selected in dependence from the respective carrier molecule or surface group. For example, L may be an aliphatic or aromatic residue, e.g. an alkyl(en) group or phenyl(en) group, comprising a reactive functional group, such as an amino group, preferably a primary amino group, (activated) carboxy group, aldehyde, azide, alkenyl or alkinyl group. In specific embodiments L may comprise a polyether or polyester chain. In particular, L is selected from the group comprising primary alkylamines, alkyl or aralkyl residues with a terminal aldehyde, azide, alkine or alkene group or (activated) carboxy group, and alkylaryl and aryl residues, e.g. phenyl residues, comprising a reactive amine, aldehyde or azide group, or (activated) carboxy group.

In a specific embodiment of the invention, L is $(CH_2)_nNH_2$, with n being an integer from 2 to 50, preferably 3 to 20 or 3 to 10, such as 4 to 8.

The carrier may be any carrier molecule known in the art, in particular in the field of vaccine development, e.g. as disclosed in Hecht et al., Curr. Opin. Chem. Biol. 13, 354-359. (2009). More specifically the carrier is a protein carrier selected from the group comprising diphtheria toxoid $CRM_{197}$, tetanus toxoid (TT), outer membrane protein (OMP), bovine serum albumin, (BSA), keyhole limpet hemocyanine (KLH), diphtheria toxoid (DT), cholera toxoid (CT), recombinant *Pseudomonas aeruginosa* exotoxin A (rEPA), *Clostridium difficile* toxin A (TcdA), *Clostridium difficile* toxin B (TcdB).

The synthetic pentasaccharide derived from the repeating unit of *C. difficile* PS-I will induce an immunogenic and antigenic response in mice, livestock and human patients.

Consequently, an aspect of the present invention relates to a vaccine against the pathogen *Clostridium difficile* comprising at least one of the group consisting of the synthetic oligosaccharide, the oligosaccharide-protein conjugate, or a conjugate of the oligosaccharide according to the invention or derivative thereof with a non-protein carrier molecule.

The oligosaccharide-protein conjugate or the oligosaccharide, in particular the pentasaccharide, of the invention may be advantageously used for preparing a pharmaceutical composition for the treatment or prevention of a disease caused by a pathogenic strain of *Clostridium difficile.*

In a related aspect they may be used in a method for the treatment or prevention of a disease caused by the pathogen *Clostridium difficile.*

In a further related aspect they may be used as diagnostic tools for detecting *Clostridium difficile* or identifying a certain strain of *Clostridium difficile* in a sample and/or a *Clostridium difficile* infection in a subject. Such a method may be, e.g. a diagnostic method for *Clostridium difficile* infection comprising the use of the synthetic oligosaccharide of the invention or a mixture thereof. They may for example be used as effective standards for immunoassays for the detection of *C. difficile.*

A further aspect of the invention relates to an antibody having specificity for an immunogenic determinant derived from or comprising the repeating unit of the *Clostridium difficile* glycopolymer PS-I. More specifically, the immunogenic determinant comprises or consists of the pentasaccharide of the invention.

In a specific embodiment, said antibody has been raised against a oligosaccharide-protein conjugate wherein the oligosaccharide is the pentasaccharide 1 or a derivative thereof and the protein carrier is diphtheria toxoid $CRM_{197}$.

The antibody may be a polyclonal or monoclonal antibody and monoclonal antibodies can be readily prepared by standard methods of the art (e.g. Köhler and Milstein (1975), Nature, 495-497).

The present invention also provides very favourable and efficient methods for synthesizing the pentasaccharide and pentasaccharide-protein conjugates selectively and in high yields.

These methods involve the use of one or more of molecules 2, 2', 3, 4, 5, 20, 21, 22, 23, 24, 27, 29, 30, 30', 31, 32, 32', 33, 33', 34' as shown or defined below as intermediates or building blocks for preparing the pentasaccharide α-L-Rhap-(1→3)-β-D-Glcp-(1→4)-[α-L-Rhap-(1→3)]-α-D-Glcp-(1→2)-α-D-Glcp or of a derivative thereof.

2'

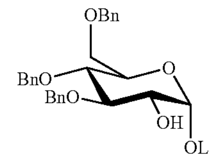

2 L = $(CH_2)_5NBnCbz$

3

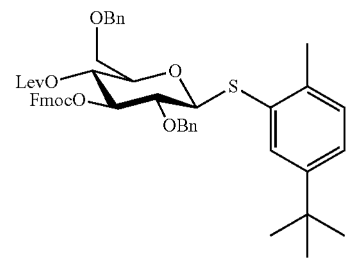

4

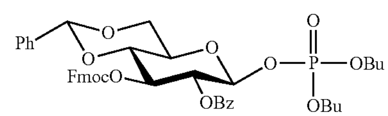

5

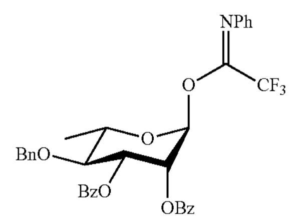

20'

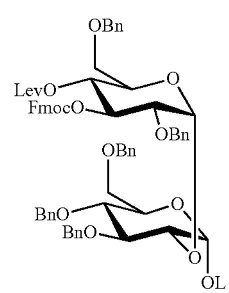

20 L = $(CH_2)_5NBnCbz$

21'

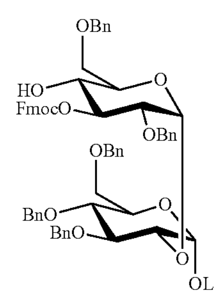

21 L = $(CH_2)_5NBnCbz$

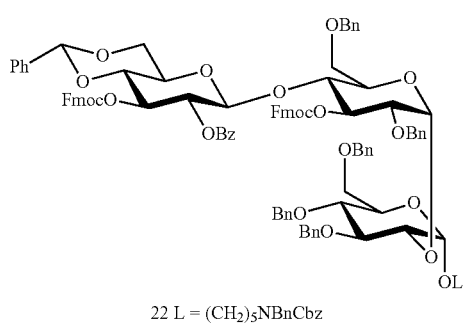
22 L = (CH₂)₅NBnCbz
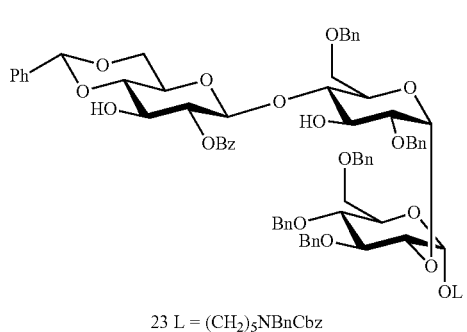
23 L = (CH₂)₅NBnCbz
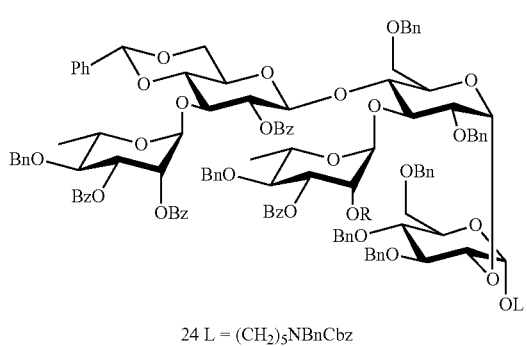
24 L = (CH₂)₅NBnCbz
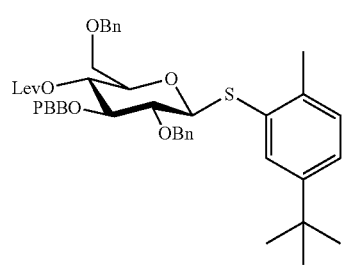
27
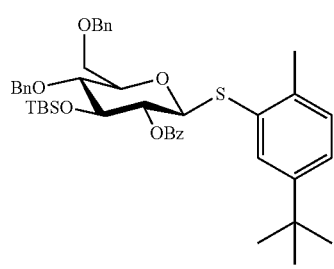
29
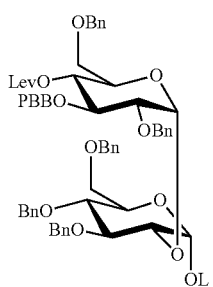
30 L = (CH₂)₅NBnCbz
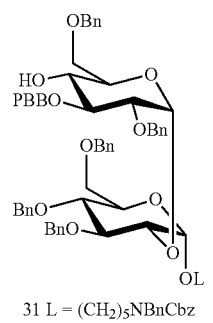
31 L = (CH₂)₅NBnCbz
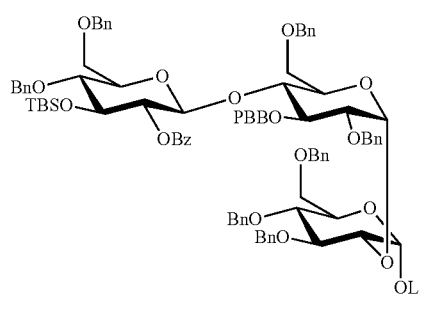
32 L = (CH₂)₅NBnCbz
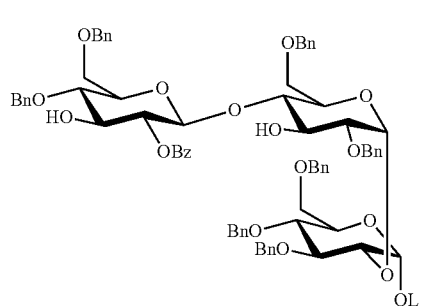
33 L = (CH₂)₅NBnCbz -continued

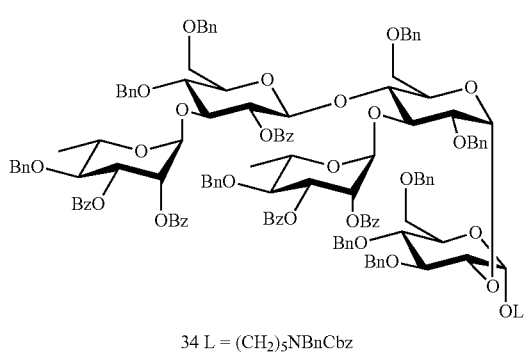

34 L = (CH₂)₅NBnCbz

A first preferred method (method A) for synthesizing the pentasaccharide 1 shown in Scheme 1 below

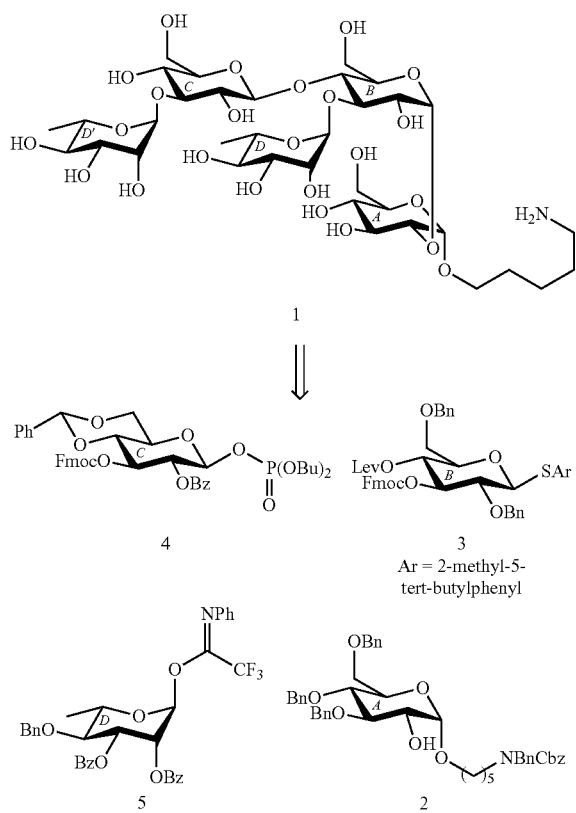

Scheme 1. Retrosynthetic analysis of pentasaccharide 1.

Ar = 2-methyl-5-tert-butylphenyl comprises assembling the monosaccharide building blocks 2 and 3 or 4 shown in Scheme 1 to yield the corresponding disaccharide 21 of Scheme 5, reacting the disaccharide 21 with building block 4 to form the trisaccharide 23 of Scheme 5, subjecting the trisaccharide 23 to a bis-glycosylation reaction with 2 molecules of building block 5 shown in Scheme 1 to yield the fully protected pentasaccharide 24 in Scheme 5 and finally, after deprotection, to yield pentasaccharide 1.

This method can be generalized for preparing other pentasaccharides having the sequence α-L-Rhap-(1→3)-β-D-Glcp-(1→4)-[α-L-Rhap-(1→3)]-α-D-Glcp-(1→2)-α-D-Glcp-L according to the invention wherein the specific amino linker of compound 1 is replaced by any linker L, in particular any linker L as defined herein. This linker may also be present on a position (sugar moiety) different from the specific position (sugar moiety) indicated above. The generalized method comprises assembling a monosaccharide building block 2', wherein the specific protected amino linker of building block 2 is replaced by a protected or unprotected linker L, in particular a linker L as defined herein, and building blocks 3 or 4 shown in Scheme 1 to yield the corresponding disaccharide 21', reacting the disaccharide 21' with building block 4 to form the trisaccharide 23', subjecting the trisaccharide 23' to a bis-glycosylation reaction with 2 molecules of building block 5 shown in Scheme 1 to yield the fully protected pentasaccharide 24' in Scheme 5 and finally, after deprotection, to yield pentasaccharide 1', wherein the specific amino linker of pentasaccharide 1 is replaced by a different linker L, in particular a linker L as defined herein.

The method for preparing the oligosaccharide-protein conjugate of the present invention typically comprises coupling the oligosaccharide of the invention bearing a linker or spacer group L, in particular wherein L is $(CH_2)_n NH_2$, with n being an integer from 2 to 50, preferably from 3 to 20, with a protein carrier.

More specifically, said method comprises providing a pentasaccharide having the sequence α-L-Rhap-(1→3)-β-D-Glcp-(1→4)-[α-L-Rhap-(1→3]-α-D-Glcp-(1→2)-α-D-Glcp-L bearing a linker L=$(CH_2)_n NH_2$, with n being an integer from 2 to 50, preferably from 3 to 20, and reacting the unique terminal amine of the linker L with one of the two NHS-activated esters of Di(N-succinimidyl) adipate to form an amide and subsequent coupling of the activated amide moiety to the protein carrier. The protein carrier may be any carrier disclosed above and in one specific embodiment the protein carrier is $CRM_{197}$.

In the following, the methods of synthesis according to the invention are outlined in more detail with respect to preferred embodiments but are not limited thereto.

General Oligosaccharide Synthesis

The present inventors developed very effective methods for synthesizing a pentasaccharide having the sequence α-L-Rhap-(1→3)-β-D-Glcp-(1→4)-[α-L-Rhap-(1→3)]-α-D-Glcp-(1→2)-α-D-Glcp-L that comprises the PS-I repeating unit but differs from the natural pentasaccharide by the linker L. In a preferred embodiment, the oligosaccharide was designed to carry a primary amine at the reducing terminus via a linker to facilitate conjugation to a protein carrier and attachment to microarrays or other surfaces. Based on the retrosynthetic analysis (Scheme 1), the pentasaccharide 1—wherein the linker comprises the $(CH_2)_5 NH_2$ group—can be assembled from the monosaccharide building blocks 2 and 3 or 4, and the monosaccharide building block 5 and these assembling steps are outlined in more detail below.

However, it is to be understood that analogous assembling steps can be performed using an analogous building block 2' differing from building block 2 only by the presence of a different linker, in particular such as defined herein, resulting in an analogous pentasaccharide 1'.

The 1,2-cis glycosidic linkages of the glucose residues A and B were installed early in the synthesis by employing the non-participating protecting groups 2-naphthylmethyl (NAP) and benzyl in 2-positions. The temporary protecting groups Lev and Fmoc present in the glucose building blocks B and C were chosen for their compatibility with automated solid phase synthesis (K. R. Love and P. H. Seeberger, *Angew. Chem. Int. Ed.*, 2004, 43, 602). Both Rha residues D and D' were installed in a single bisglycosylation reaction.

Following placement of the NAP-protection in thioglycoside 6 (S. J. Danishefsky, S. Hu, P. F. Cirillo, M. Eckhardt and P. H. Seeberger, *Chem. Eur. J.,* 1997, 3, 1617) the terminal linker carrying a latent amine was introduced by union of thioglucoside 7 and the linker prior to subsequent DDQ-mediated cleavage of the C-2 napthyl ether in order to produce glucose building block 2 (Scheme 2) a) J.-G. Delcros, S. Tomasi, S. Carrington, B. Martin, J. Renault, I. S. Blagbrough and P. Uriac, *J. Med. Chem.,* 2002, 45, 5098; b) J. Xia, S. A. Abbas, R. D. Locke, C. F. Piskorz, J. L. Alderfer and K. L. Matta, *Tetrahedron Lett.,* 2000, 41, 169)

Scheme 2. Synthesis of building block 2.

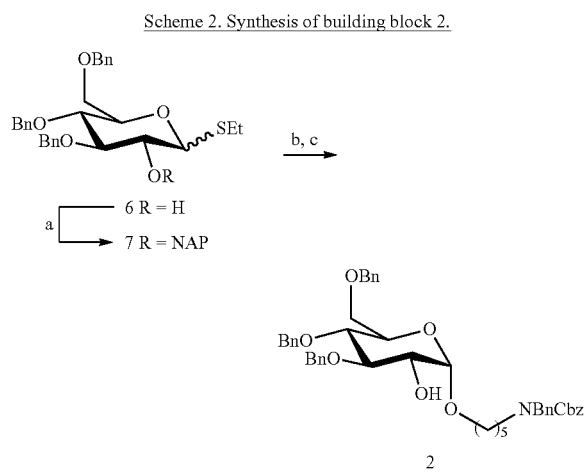

Reagents and conditions: a) NaH, NAPBr, DMF, 0° C. to rt, 92%;
b) HO(CH₂)₅NBnCbz, NIS, TfOH, toluene/dioxane, -40° C. to -20° C.;
c) DDQ, DCM, H₂O, 35% over 2 steps.

The synthesis of thioglucoside 11 that served as common precursor for building blocks 3 and 4 commenced from β-d-glucose pentaacetate 8 (Scheme 3). Use of the nontoxic and odorless 2-methyl-5-tert-butyl-thiophenol group ensured exclusive formation of β-anomer of thioglucoside 9 (M. Collot, J. Savreux and J.-M. Mallet, *Tetrahedron,* 2008, 64, 1523). The acetyl groups were removed and the 4- and 6-hydroxyl groups of the resulting tetraol were regioselectively protected as a 4,6-O-benzylidene acetal (J. S. S. Rountree and P. V. Murphy, *Org. Lett.,* 2009, 11, 871) to afford diol 10. Regioselective placement of a TBS-ether protecting group at the 3-OH gave thioglycoside 11 (K. C. Nicolaou, N. Winssinger, J. Pastor and F. DeRoose, *J. Am. Chem. Soc.,* 1997, 119, 449).

Scheme 3. Synthesis of monosaccharide building blocks 3 and 4.

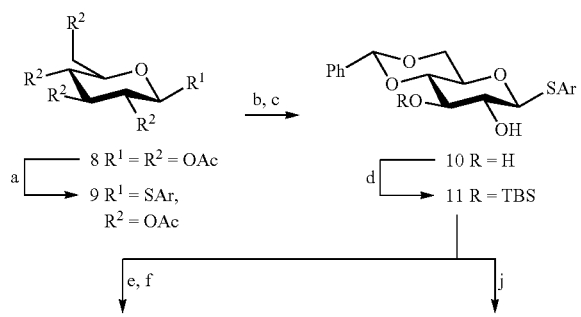

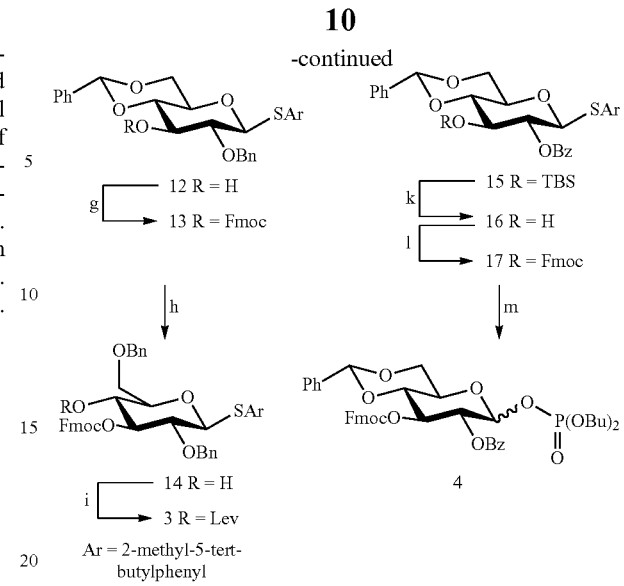

Ar = 2-methyl-5-tert-butylphenyl

Reagents and conditions: a) 2-methyl-5-tert-butylthiophenol, BF₃·OEt₂, DCM, 85%;
b) NaOMe, MeOH, rt; c) benzaldehyde dimethyl acetal, CSA, MeCN, 87% over 2 steps;
d) TBS—Cl, imidazole, DMF, 0° C., 69%; e) NaH, BnBr, DMF, 0° C. to rt; f) 1M TBAF in THF, 0° C. to rt, 93% over 2 steps; g) Fmoc—Cl, pyridine, DCM, 95%; h) TES, TfOH, DCM, 4 Å MS, -78° C., 73%; i) Lev₂O, pyridine, DCM, 3 days, 79%; j) BzCl, DMAP, pyridine, 70° C., 88%. k) TBAF·3H₂O, AcOH, DMF, 35° C., 91%; l) Fmoc—Cl, pyridine, DCM, 96%; m) HOPO (OBu)₂, NIS/TfOH, DCM, 4 Å MS 0° C., 81%.

Synthesis of building block 3 began with the installation of the non-participating benzyl group at the 2-position of 12 to favor the formation of the α-glycosidic linkage between monosaccharides A and B fragments. Subsequent placement of the 3-O-Fmoc-protection furnished compound 13. Finally, the regioselective opening of the 4,6-O-benzylidene acetal with TES-TfOH and protection of the free 4-hydroxyl gave orthogonally protected building block 3. Preparation of differentially protected glucosyl phosphate 4 from 11 followed a similar route. In anticipation of the formation of a 1,2-trans linkage between the B and C saccharide fragments, a participating benzoyl group was installed at the 2-position of 15. During TBAF-mediated desilylation of 15, careful control of the TBAF:AcOH ratio was essential to prevent benzoyl-migration from the C2- to C3-positions. Fmoc-protected thioglycoside 17 was further converted to glycosyl phosphate 4.

Synthesis of the rhamnosyl building block 5 to provide the D fragment commenced with the bis-benzoylation of 4-methoxyphenyl glycoside 18 (Scheme 3) (D. B. Werz, A. Adibekian and P. H. Seeberger, *Eur. J. Org. Chem.,* 2007, 12, 1976). CAN-mediated removal of the anomeric p-methoxyphenyl group yielded the free lactol that was immediately converted into rhamnosyl N-phenyl trifluoroacetimidate 5 (B. Yu and H. Tao, *Tetrahedron Lett.,* 2001, 42, 2405).

Scheme 4. Synthesis of rhamnosyl building block 5.

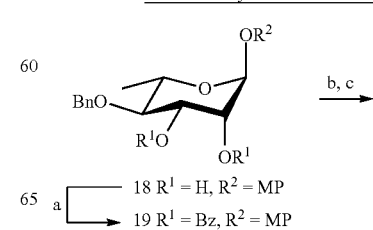

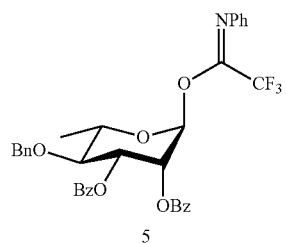

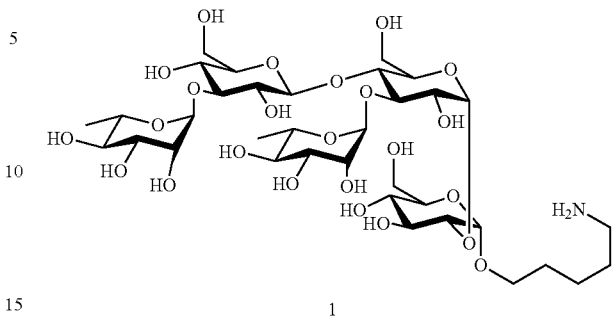

Reagents and conditions: a) BzCl, DMAP, pyridine, DCM, 0° C. to rt, 97%; b) CAN, MeCN, H$_2$O; c) CF$_3$C(NPh)Cl, Cs$_2$CO$_3$, DCM, 74% over 2 steps.

Reagents and conditions: a) 3, NIS/TfOH, Et$_2$O, -35° C. to -10° C., 70%; b) N$_2$H$_4$•H$_2$O, AcOH/pyridine, DCM, 94%; c) 4, TMSOTf, DCM, 4 Å MS, -35° C. to -7° C.; d) NEt$_3$, DCM, rt, 38% over 2 steps; e) 5, TMSOTf, DCM, 4 Å MS, -30° C. to -15° C., 81%; f) NaOMe, THF/MeOH, 50° C.; g) H$_2$, 10% Pd/C, MeOH, H$_2$O, The assembly of the pentasaccharide target was achieved in seven linear steps by combining the monosaccharide building blocks in sequence (Scheme 5).

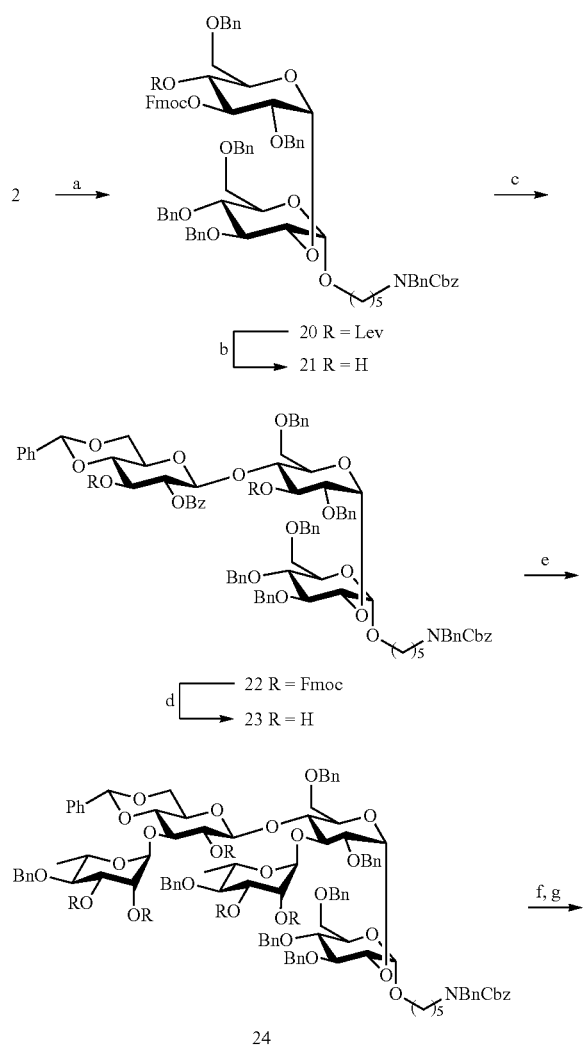

Installation of the α-glycosidic linkage was the result of the union of glycosylating agent 3 and nucleophile 2. Disaccharide 20 was obtained in good yield and stereoselectivity when NIS and TfOH in Et$_2$O was employed as promoter system. Selective cleavage of the levulinic ester with hydrazine hydrate in pyridine/AcOH, did not compromise the integrity of the Fmoc-group but cleanly produced disaccharide acceptor 21. Thioglucoside building block 17, a very storage-stable monomer unit had been intended for the installation of the next glycosidic linkage to form trisaccharide 22. Upon a variety of conditions only traces of the desired product 22 were isolated. As a first means to remedy the situation, replacement of the anomeric leaving group was executed. Glycosyl phosphate 4 was activated by TMSOTf to promote the glycosylation of 21 and afforded 22, although purification was achieved only following Fmoc cleavage to yield 23. Conversion of diol 23 to fully protected pentasaccharide 24 was achieved by bis-glycosylation using rhamnosyl-imidate 5 in the presence of TMSOTf. Final deprotection of compound 24 required two transformations: saponification of the benzoate esters and catalytic hydrogenation of the aromatic groups gave pentasaccharide 1. Careful comparison of the spectroscopic data for synthetic pentasaccharide 1 and NMR spectra of native PS-I revealed excellent agreement.

In summary, the first synthesis of the *C. difficile* cell-surface PS-I pentasaccharide 1 was achieved employing a linear strategy that serves to scout reaction conditions for automated solid phase synthesis and to identify robust and efficient monosaccharide building blocks. Four such building blocks 2-5 were prepared. Glycosyl phosphate 4 proved a significantly better building block than identically protected thioglycoside 3.

The present inventors also developed an alternative route of synthesis based on a similar strategy as outlined above which is even more efficient and results in greatly improved yields of the PS-I pentasaccharide product.

The innovation of this improved synthesis relies on the use of the protecting group para-bromobenzyl (PBB) [Plante et al., J. Am. Chem Soc. 122:7148-7149, 2000; Liu et al., Chem.

Commun. 1708-2709; 2004]. Building block 27, modified with PBB at C-3 was obtained in three steps from intermediate 12 described above (Scheme 3). PBB-containing 27 was used for the following pentasaccharide synthesis rather than Fmoc-containing 3 used in the method outlined above.

more stable 29. The 4,6-O-benzylideneacetal ring of previously reported intermediate 15 was opened selectively, followed by

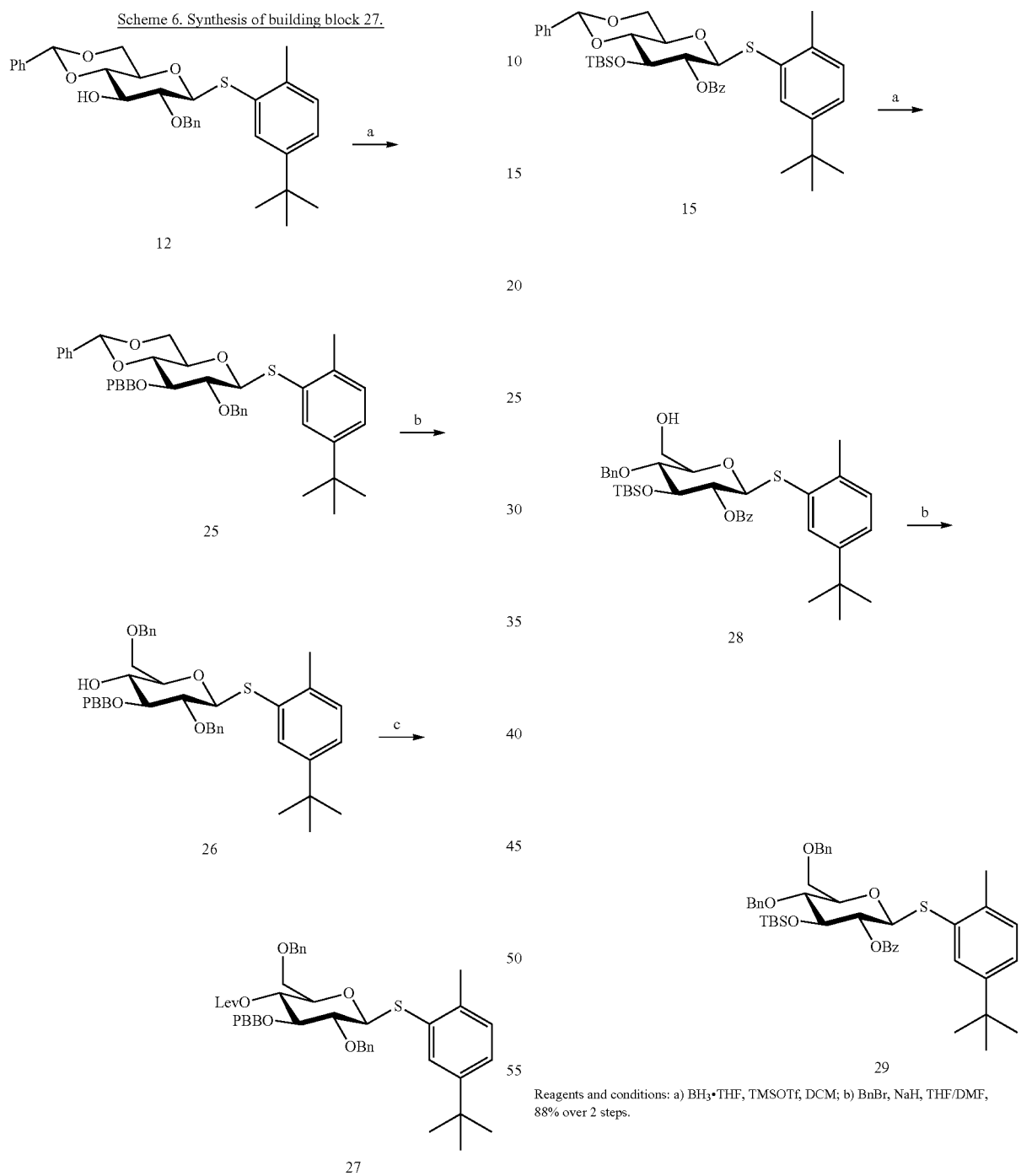

A further improvement of the previous synthesis was achieved by replacing the acid-labile building block 4 with Assembly of the pentasaccharide took place similarly as described above for method A; changes were made in the deprotection steps d), e) and f) (Scheme 8) due to the modified protective group pattern.

Scheme 8. Synthesis of pentasaccharide 1 (method B).
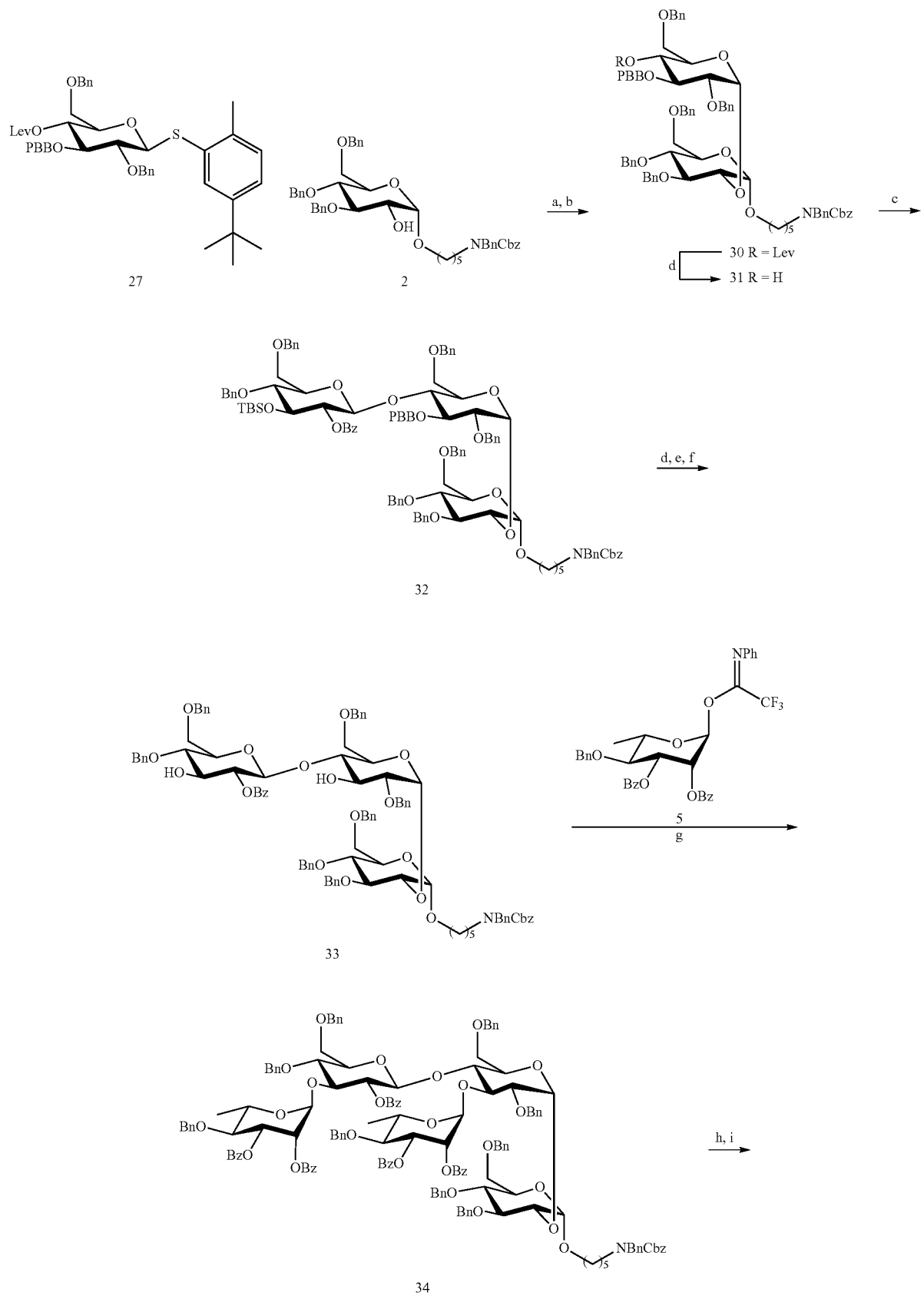

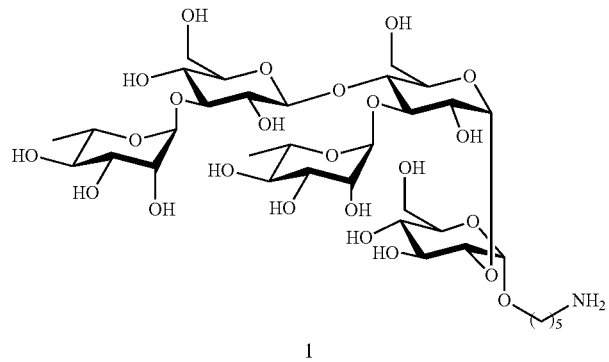

1

Reagents and conditions: a) NIS/TfOH, Et₂O, -20° C. to 0° C., 69%; b) N₂H₄·H₂O, AcOH/Pyridine, DCM, 96%; c) 29, NIS/TfOH, DCM, -30° C. to -10° C., 92%; d) cat. Pd(OAc)₂, (3,4-dimethoxyphenyl)boronic acid, TBABr, K₃PO₄, EtOH, 92%; e) DDQ, aq. NaHCO₃, H₂O, DCM; f) TBAF·3H₂O, AcOH, DMF, 50° C., 68% over 2 steps; g) TMSOTf, DCM, 4 Å MS, -30° C. to -15° C., 88%; h) NaOMe, THF/MeOH, rt; i) H₂, 10% Pd/C, MeOH, H₂O, AcOH, 59% over 2 steps.

Synthesis of the pentasaccharide 1 according to method B preferably comprises assembling the monosaccharide building blocks 2 and 27 shown in Scheme 8 to yield the corresponding disaccharide 30 of scheme 8, reacting the disaccharide 30 with building block 4 or 29 to form the protected trisaccharide 32 of scheme 8, deprotecting the trisaccharide 32 to obtain trisaccharide 33 and subjecting trisaccharide 33 to a bis-glycosylation reaction with 2 molecules of building block 5 shown in Scheme 8 to yield the fully protected pentasaccharide 34 in Scheme 8 and finally, after deprotection, to yield pentasaccharide 1.

Formation of the Glc(1→4)Glc linkage (Scheme 8, step c) proceeded in 92% yield, a huge improvement compared to 38% in method A.

This method can be generalized for preparing other pentasaccharides having the sequence α-L-Rhap-(1→3)-β-D-Glcp-(1→4)-[α-L-Rhap-(1→3)]-α-D-Glcp-(1→2)-α-D-Glcp-L according to the invention wherein the specific amino linker of compound 1 is replaced by any linker L, in particular any linker L as defined herein. This linker may also be present on a position (sugar moiety) different from the specific position (sugar moiety) indicated above. The generalized method comprises assembling a monosaccharide building block 2', wherein the specific protected amino linker of building block 2 is replaced by a protected or unprotected linker L, in particular a linker L as defined herein, and building block 27 shown in Scheme 8 to yield the corresponding disaccharide 30', reacting the disaccharide 30' with building block 4 or 29 to form the corresponding protected trisaccharide 32', deprotecting the trisaccharide 32' to obtain trisaccaride 33', subjecting the trisaccharide 33' to a bis-glycosylation reaction with 2 molecules of building block 5 shown in Scheme 1 to yield the fully protected pentasaccharide 34' and finally, after deprotection, to yield pentasaccharide 1', wherein the specific amino linker of pentasaccharide 1 is replaced by a different linker L, in particular as defined herein.

Synthesis of PS-I Substructures

A comprehensive set of PS-I substructures 35-39 (Scheme 9) carrying an amino-linker was synthesized. The pentasaccharide repeating unit 1 is built up from glucose residues A, B and C and terminal rhamnoses D and D'. Disaccharide 35 contains A and B, trisaccharide 36 A, B and C. The sequence BCD' is covered by trisaccharide 37. Disaccharide 38 covers both the BD and CD' sequence. Rhamnose substructure 39 represents D and D'.

Scheme 9. Pentasaccharide 1 and comprehensive set of substructures 35-39.

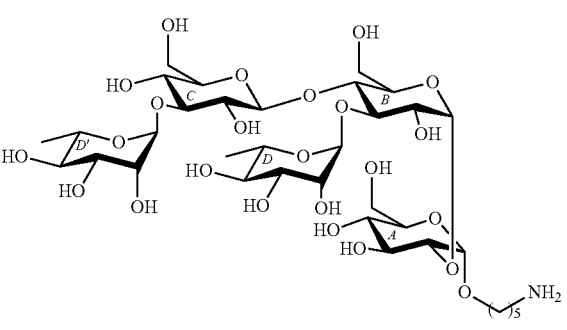

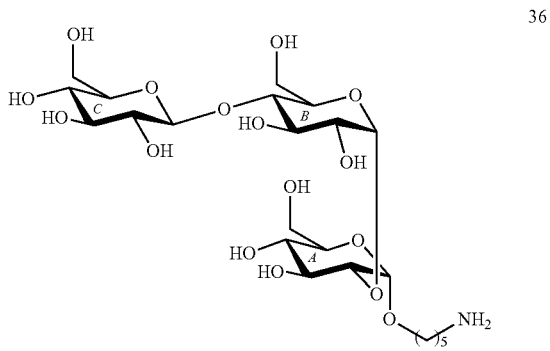

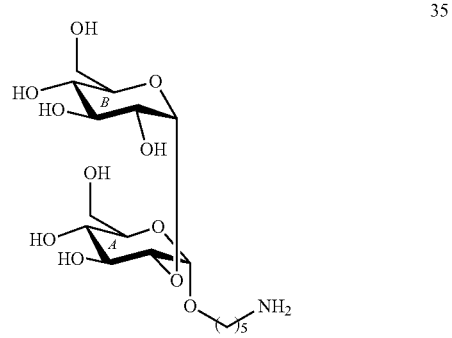

19
-continued

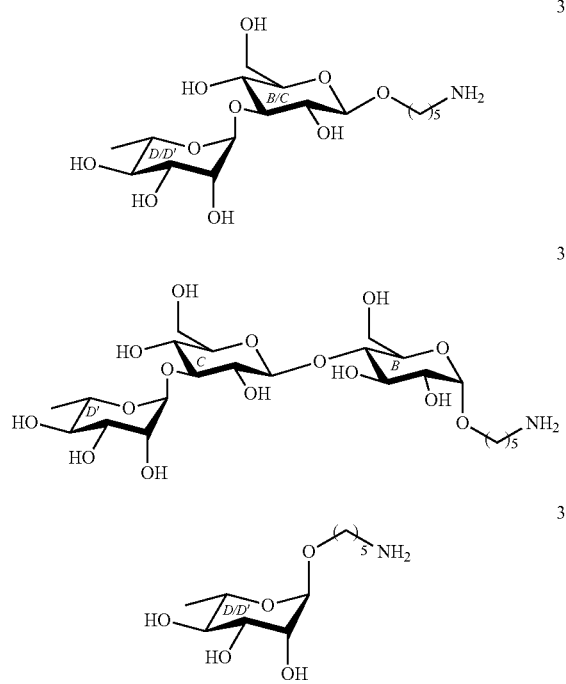

Oligoglucose disaccharide 35 (Scheme 10) and trisaccharide 36 (Scheme 11) were obtained by catalytic hydrogenation of protected disaccharide 31 and trisaccharide 33.

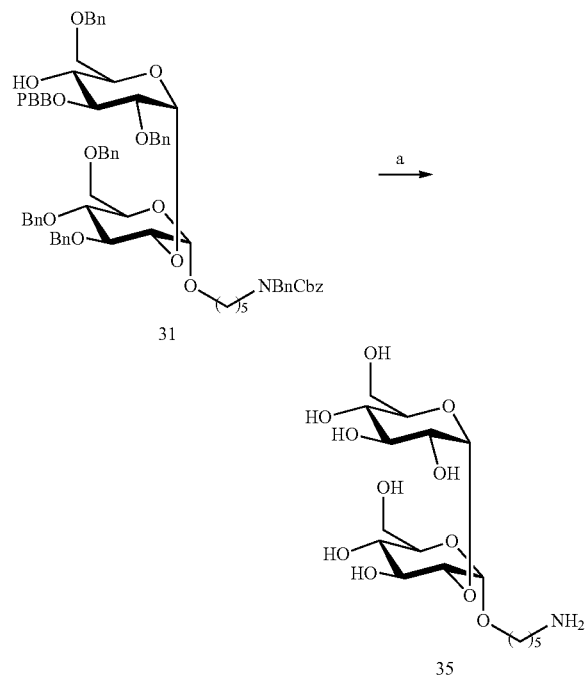

Reagents and conditions: a) H₂, 10% Pd/C, MeOH, THF, H₂O, AcOH, 99%.

20

Scheme 11. Synthesis of 36.

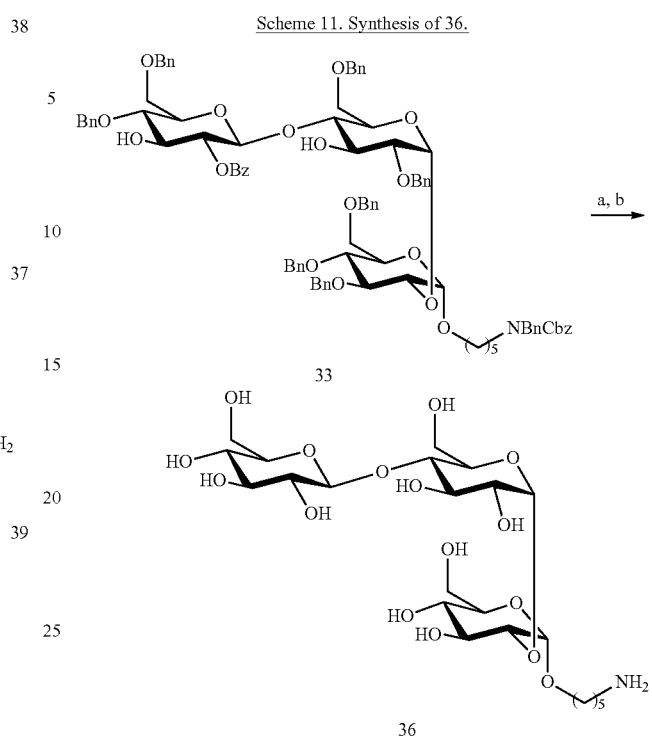

Reagents and conditions: a) NaOMe, THF/MeOH; b) H₂, 10% Pd/C, MeOH, THF, H₂O, AcOH, 66% over 2 steps.

Oligosaccharides 38 (Scheme 12) and 37 (Scheme 13) containing a terminal rhamnose residue were synthesized relying on disaccharide 41 which in its turn was obtained by union of 40 and 5.

Scheme 12. Synthesis of 38.

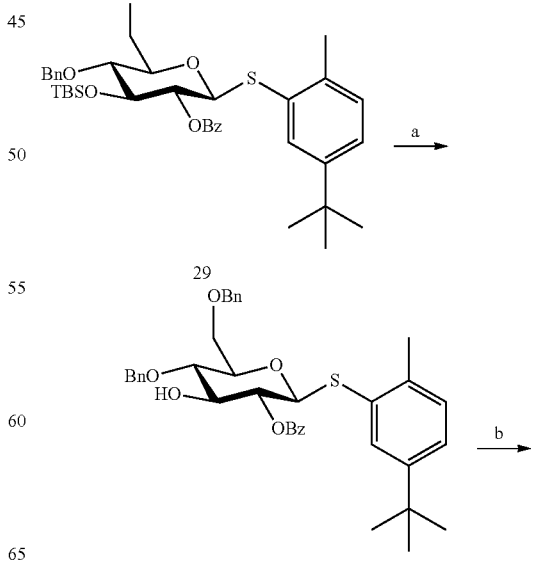

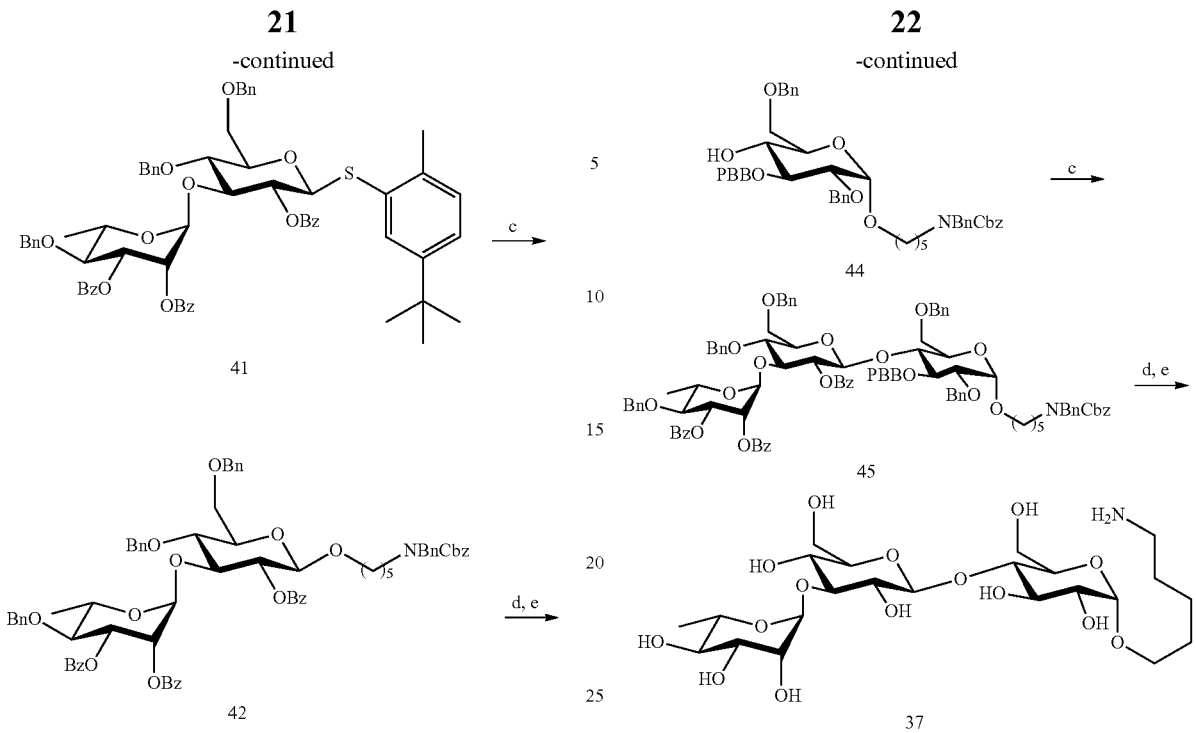

Reagents and conditions: a) TBAF·3H₂O, AcOH, DMF, 35° C.; b) 5, TMSOTf, DCM, 4 Å MS, -40° C. to -20° C., 79% over 2 steps; c) 5-aminopentanol, NIS/TfOH, DCM, -20° C. to 0° C., 91%; d) NaOMe, THF/MeOH; e) H₂, 10% Pd/C, MeOH, THF, H₂O, AcOH, 75% over 2 steps.

Reagents and conditions: a) 5-aminopentanol, NIS/TfOH, Et₂O, -10° C., to 0° C., 39%; b) N₂H₄·H₂O, AcOH/Pyridine, DCM, 81%; c) 41, NIS/TfOH, DCM, -20° C. to 0° C., 95%; d) NaOMe, THF/MeOH; e) H₂, 10% Pd/C, MeOH, THF, H₂O, AcOH, 78% over 2 steps.

Rhamnoside 39 (Scheme 14) bearing an anomeric linker was attained by combining 5 and 5-aminopentanol.

Scheme 14. Synthesis of 39.

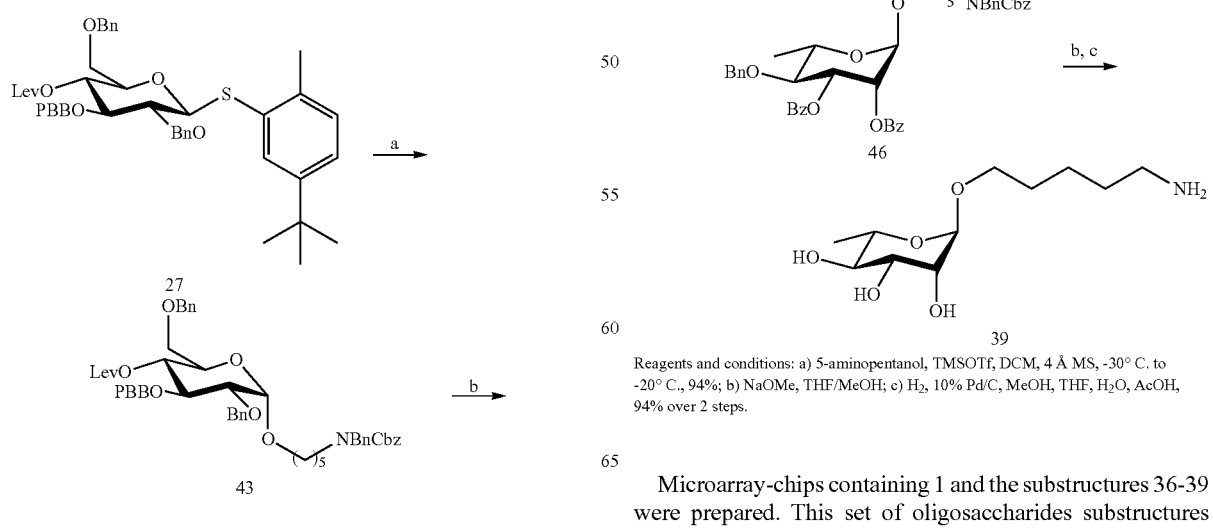

Reagents and conditions: a) 5-aminopentanol, TMSOTf, DCM, 4 Å MS, -30° C. to -20° C., 94%; b) NaOMe, THF/MeOH; c) H₂, 10% Pd/C, MeOH, THF, H₂O, AcOH, 94% over 2 steps.

Figure 6:
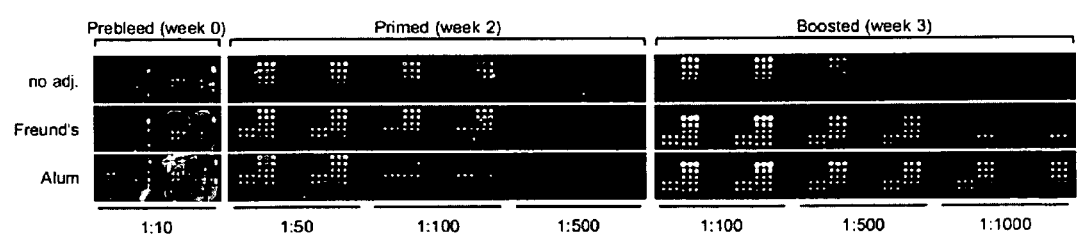

Microarray-chips containing 1 and the substructures 36-39 were prepared. This set of oligosaccharides substructures covalently linked to a surface was used to identify binding epitopes of anti PS-I pentasaccharide antibodies raised in mice (FIG. 6).

The pentasaccharide 1 or 1' obtained as outlined above or a fragment or derivative thereof can be coupled to a carrier protein by a variety of known methods.

A particular advantageous and preferred method uses the approach shown in scheme 15 below. For this the unique, terminal amine of 1 was first reacted with one of the two NHS-activated esters of Di(N-succinimidyl) adipate to form an amide. The coupling of the activated pentasaccharide to $CRM_{197}$ proceeded in phosphate buffer (any other usual buffer providing the desired pH is also suitable) and in one experiment resulted in a load that averaged 3.6 pentasaccharide units per protein, as determined by MALDI-TOF mass spectrometry. However, other pentasaccharide loads (such as e.g. about 9.6 units per carrier molecule) are also possible by varying the reaction conditions (compare Example 3).

Figure 7:
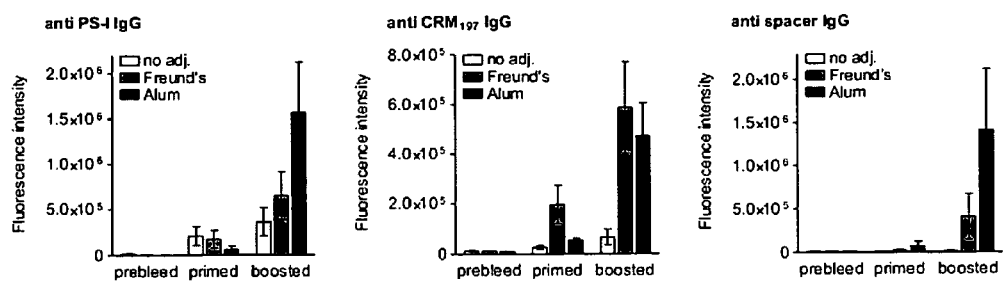

FIG. 7. Antibody titers against the PS-I pentasaccharide (left), $CRM_{197}$ (center), and spacer moiety (right), as determined by microarray analysis FIG. 8. Isotype analysis of the immune response against PS-I pentasaccharide FIG. 9. Microarray design including PS-I pentasaccharide 1 and substructures thereof, 35 through 39

Figure 10:
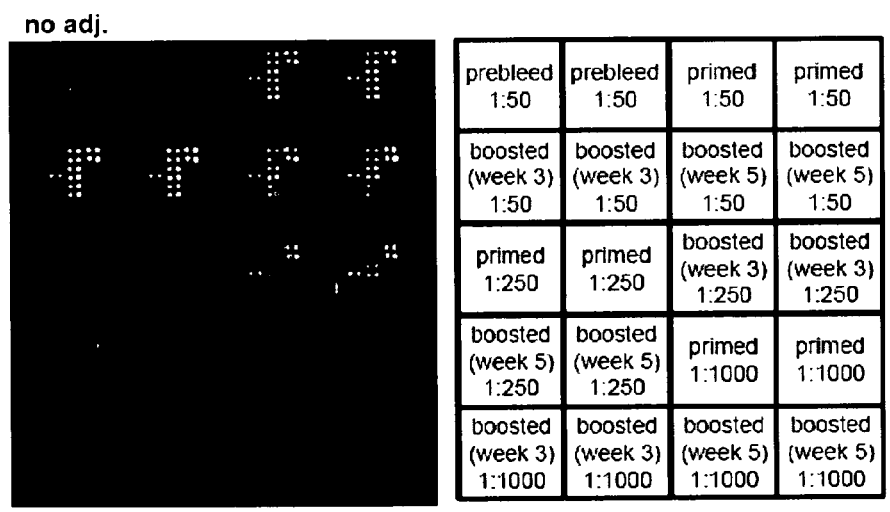

FIG. 10. Immune response against PS-I substructures of mice immunized with PS-I glycoconjugate without adjuvant FIG. 11. Immune response against PS-I substructures of mice immunized with PS-I glycoconjugate and Freund's adjuvant FIG. 12. Immune response against PS-I substructures of mice immunized with PS-I glycoconjugate and Alum adjuvant FIG. 13. Isotype analysis of monoclonal antibodies and their reactivities against PS-I substructures Scheme 15. Synthesis of conjugate 1 (1a).

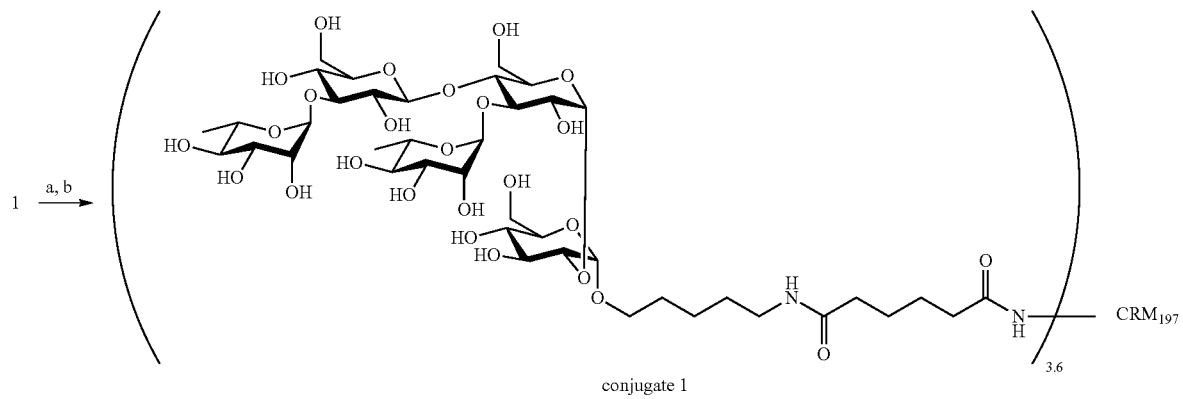

Reagents and conditions: a) Di(N-succinimidyl) adipate, NEt$_3$, DMSO; b) CRM$_{197}$, phosphate buffer (pH 7.5).

Microarray Chips

Oligosaccharides, in particular pentasaccharide 1 and substructures 35 through 39, were immobilized on the surface of NHS-activated glass slides via their terminal primary amine group of the linker moiety. These microarrays were used to detect and quantify oligosaccharide-specific antibodies.

Polyclonal and Monoclonal Antibodies

Monoclonal antibodies (mABs) were generated using the standard method by Köhler and Milstein, 1975. These showed specificity for pentasaccharide 1.

The invention is further illustrating by the following non-limiting Examples and Figures.

FIGURES

FIG. 1. Glycoconjugate 1 composed of hapten 1 (pentasaccharide 1) and protein $CRM_{197}$ FIG. 2. Characterization of glycoconjugate 1a; a) SDS-PAGE; b) MALDI-TOF; c) HPLC FIG. 3. Conjugate reaction resulting in glycoconjugate 1b FIG. 4a. SDS-PAGE analysis of $CRM_{197}$ glycoconjugate 1b FIG. 4b. MALDI-TOF MS analysis of $CRM_{197}$ glycoconjugate 1b FIG. 5. Microarray design FIG. 6. Microarray analysis of immune response against glycoconjugate. Dilutions of pooled sera in PBS are indicated under the microarray images.

EXAMPLE 1

Preparation and Characterization of a Pentasaccharide Based on the Repeating Unit of C. difficile Polysaccharide PS-I The pentasaccharide was designed to provide, by means of a linker group, a primary amine at the reducing terminus to facilitate conjugation to a protein carrier and attachment to microarrays and other surfaces. In the following synthesis, the linker comprises the $(CH_2)_5NH_2$ group and the overall synthesis was performed according to scheme 5 or 8 above as indicated.

General Experimental

Commercial grade reagents and solvents were used without further purification except as indicated below. All batch reactions conducted under an Ar atmosphere. $^1$H-NMR and $^{13}$C-NMR spectra were measured with a Varian 400-MR or Varian 600 spectrometer. The proton signal of residual, non-deuterated solvent (δ 7.26 ppm for CHCl$_3$; δ 4.79 ppm for H$_2$O, 2.84 ppm for acetone) was used as an internal reference for $^1$H spectra. For $^{13}$C spectra, the chemical shifts are reported relative to the respective solvent (δ 77.16 ppm for CDCl$_3$, δ 29.84 ppm for acetone). For $^{13}$C spectra in D$_2$O, MeOH (δ 49.50 ppm) was added as internal standard. Coupling constants are reported in Hertz (Hz). The following abbreviations are used to indicate the multiplicities: s, singlet;

d, doublet; t, triplet; m multiplet. Infrared (IR) spectra were recorded as thin films on a Perkin Elmer Spectrum 100 FTIR spectrophotometer. Optical rotations (OR) were measured with a Schmidt & Haensch UniPol L 1000 at 589 nm and a concentration (c) expressed in g/100 mL. High-resolution mass spectra (HRMS) were recorded with an Agilent 6210 ESI-TOF mass spectrometer at the Freie Universität Berlin, Mass Spectrometry Core Facility. MALDI-TOF spectra were recorded on a Bruker Daltonics Autoflex Speed. Synthetic carbohydrates were measured using a 2,4,6-trihydroxyacetophenone (THAP) matrix, proteins and glycoconjugates were measured using 2,4-dihydroxyacetophenone (DHAP) as matrix.

Analytical thin layer chromatography (TLC) was performed on Kieselgel 60 F254 glass plates precoated with a 0.25 mm thickness of silica gel. The TLC plates were visualized with UV light and by staining with Hanessian solution (ceric sulfate and ammonium molybdate in aqueous sulfuric acid) or a 1:1 mixture of $H_2SO_4$ (2N) and resorcine monomethylether (0.2%) in ethanol. Column chromatography was performed using Kieselgel 60 (230-400 mesh). SEC-HPLC analyses were performed on a TSKgel-G4000SWXL column connected to an Agilent 1200 HPLC system equipped with a PDA detector. Elution buffer was constituted by 100 mM sodium phosphate pH 7.2, 100 mM NaCl flow rate was 0.4 mL/min. SDS PAGE gels were run with 10% SDS PAGE gel in reducing conditions at 130 V and 50 mA, molecular weight marker (Invitrogen bench marker) was used.

Synthesis of Pentasaccharide 1 and Intermediates According to Schemes 1-5

Ethyl-3,4,6-tri-O-benzyl-2-O-(2-naphthalenylmethyl)-1-thio-D-glucopyranoside (7)

To a solution of 6 (284 mg, 0.57 mmol) in anhydrous DMF (1 mL), NaH (20.7 mg, 0.86 mmol) followed by NAP-Br (228 mg, 1.03 mmol) were added at 0° C. The mixture was warmed to room temperature over 1 h, cooled to 0° C. and quenched by the addition of MeOH (0.1 mL). $Et_2O$ was added and the organic layer washed with 0.01 M HCl solution and with saturated aqueous $NaHCO_3$ solution. The phases were separated and the organic layer was dried over $MgSO_4$ and concentrated. Column chromatography (hexanes/ethyl acetate) afforded 7 (335 mg, 0.53 mmol, 92%) in a mixture of α/β-anomers as a white solid. Analytical data is reported for the β-anomer. $[\alpha]_D^{20}$=+26.1° (c=5.3, $CHCl_3$), IR $\nu_{max}$ (film) 3061, 3030, 2864, 1949, 1808, 1603, 1497, 1453, 1360, 1065 $cm^{-1}$; $^1$H-NMR (400 MHz, $CDCl_3$) δ 7.82-7.69 (4H, m, Ar—H), 7.52-7.09 (18H, m, Ar—H), 5.08-5.02 (1H, m, —$CH_2$—Ar), 4.93-4.77 (4H, m, —$CH_2$—Ar), 4.60-4.50 (3H, m, —$CH_2$—Ar), 4.47 (1H, d, J 9.7, 1-H), 3.80-3.54 (4H, m), 3.52-3.41 (2H, m), 2.84-2.66 (2H, m, S—$CH_2$—), 1.31 (3H, t, J 7.3, $CH_3$); $^{13}$C-NMR (100 MHz, $CDCl_3$) δ 138.7, 138.4, 138.2, 135.6, 133.4, 133.2, 128.56, 128.55, 128.5, 128.2, 128.1, 127.92, 127.87, 127.84, 127.80, 127.77, 127.7, 127.2, 126.5, 126.1, 126.0, 86.8, 85.2 (C-1), 82.0, 79.3, 78.2, 75.9, 75.7, 75.2, 73.6, 69.3, 25.2, 15.3; HRMS (ESI): Calcd for $C_{40}H_{42}O_5S$ [M+Na]$^+$ 657.2651. found 657.2651.

N-(Benzyl)benzyloxycarbonyl-5-amino-pentanyl-3,4,6-tri-O-benzyl-β-D-glucopyranoside (2)

Thioglucoside 7 (335 mg, 0.53 mmol) and $HO(CH_2)_5$NBnCbz (518 mg, 1.58 mmol) were coevaporated with toluene (3×10 ml), dried in vacuo, then the compounds were dissolved in a solution of anhydrous toluene:dioxane=2:1 (4.5 ml). The solution was cooled to −40° C., treated with NIS (131 mg, 0.58 mmol) and TfOH (4.7 μl, 53 μmol) and warmed to −20° C. over 1.5 h. The reaction was quenched with pyridine, diluted with DCM and washed with saturated aqueous $Na_2S_2O_3$ solution. The organic layer was dried over $MgSO_4$ and concentrated. Column chromatography on silica gel (hexanes/ethyl acetate) gave a mixture of anomers which was dissolved in DCM (10 ml) and water (1 ml) and treated with DDQ (202 mg, 0.89 mmol) at 0° C. for 2 h. The mixture was diluted with DCM and the organic layer washed with saturated aqueous $NaHCO_3$ solution, dried over $MgSO_4$ and concentrated. Column chromatography on silica gel (hexanes/ethyl acetate) afforded 2 (140 mg, 0.184 mmol, 35%) as a colorless oil. $[\alpha]_D^{20}$=+53.3° (c=5.5), IR $\nu_{max}$ (film) 3458, 3031, 2927, 1952, 1876, 1808, 1454, 1421, 1360, 1229, 1129, 1067 $cm^{-1}$; $^1$H-NMR (400 MHz, acetone-d6) δ 7.48-7.10 (25H, m, Ar—H), 5.15 (2H, bs), 4.99 (1H, d, J 11.4, —$CH_2$—Bn), 4.84 (1H, d, J 11.1, —$CH_2$—Bn). 4.79 (1H, d, J 11.4, —$CH_2$—Bn), 4.75 (1H, bs, 1-H), 4.62-4.49 (5H, m, —$CH_2$—Bn), 3.84-3.86 (6H, m), 3.62-3.47 (2H, m), 3.40 (1H, m), 3.31-3.18 (2H, m, linker-$CH_2$—), 1.67-1.50 (4H, m, linker-$CH_2$—), 1.43-1.29 (2H, m, linker-$CH_2$—); $^{13}$C-NMR (100 MHz, acetone-d6) δ 140.5, 139.8, 139.7, 139.5, 129.3, 129.1, 129.0, 128.9, 128.60, 128.58, 128.43, 128.41, 128.2, 128.0, 99.9 (C-1), 84.3, 78.7, 75.5, 75.4, 74.2, 73.3, 71.5, 70.2, 68.5, 67.4, 24.1; HRMS (ESI): Calcd for $C_{47}H_{53}NO_8$ [M+Na]$^+$ 782.3669. found 782.3633.

(2-Methyl-5-tert-butylphenyl) 2,3,4,6-tetra-O-acetyl-1-thio-β-D-glucopyranoside (9)

1,2,3,4,6-Penta-O-acetyl-β-D-glucopyranose 8 (30 g, 77 mmol) was dissolved in anhydrous DCM (34 mL). 2-Methyl-5-tert-butyl thiophenol (17 mL, 92 mmol, 1.2 eq) were added under stirring. $BF_3.OEt_2$ (13.6 mL, 108 mmol, 1.4 eq) was added dropwise and the resulting yellow solution was stirred over night. After completion the solution was diluted with DCM and extracted with saturated aqueous $NaHCO_3$ and $H_2O$, and the organic layer was dried over $MgSO_4$. The solvent was evaporated in vacuo and the residue was dried in high vacuum. The resulting yellow solid was purified by column chromatography on silica gel (cyclohexane/ethyl acetate) to afford 9 (33.4 g, 65.4 mmol, 85%). $[\alpha]_D^{20}$=−8.0° (c=1.0, $CHCl_3$); IR ($CHCl_3$): 2961, 1747, 1366, 1211, 1034, 912 $cm^{-1}$; $^1$H-NMR (400 MHz, $CDCl_3$) δ 7.52 (1H, d, J 2.0, Ar—H), 7.25-7.10 (2H, m, Ar—H), 5.19 (1H, dd, $J_1J_2$ 9.4, 1-H), 5.10-4.98 (2H, m, 4-H, 2-H), 4.64 (1H, d, J 10.6, 1-H), 4.23 (1H, dd, $J_1$ 12.2, $J_2$ 5.0, 6-Ha), 4.10 (1H, dd, $J_1$12.2, $J_2$ 1.9, 6-Hb), 3.71-3.63 (1H, m, 5-H), 2.34 (3H, s, $CH_3$), 2.07-2.03 (6H, m, OAc), 2.00-1.96 (6H, m, OAc), 1.29 (9H, s, tBu); $^{13}$C-NMR (100 MHz, $CDCl_3$) δ 170.8, 170.3, 169.5, 169.4 (C=O OAc), 149.8, 137.51, 131.47, 130.53, 130.2, 125.8, 87.0 (C-1), 75.9 (C-5), 74.2 (C-3), 70.3 (C-3), 68.3 (C-4), 62.4 (C-6), 31.4 (tBu), 20.89, 20.88, 20.74, 20.70 (OAc), 20.5 ($CH_3$); HRMS (ESI): Calcd for $C_{25}H_{34}O_9S$ [M+Na]$^+$ 533.1816. found 533.1832.

(2-Methyl-5-tert-butylphenyl)-4,6-O-benzylidene-1-thio-β-D-glucopyranoside (10)

Thioglycoside 9 (1.5 g, 2.94 mmol) was dissolved in of methanol (12 mL). Sodium methoxide (58 mg, 1.07 mmol, 0.37 eq) was added and the reaction was stirred over night. After completion, the solution was neutralized with Amberlite IR 120 (H$^+$) ion exchange resin, filtered and concentrated in vacuo. The remainder was dried in high vacuum to give (2-Methyl-5-tert-butylphenyl) 1-thio-β-D-glucopyranoside S1 (1.0 g) which was used for the next reaction step without further purification. Tetrol S1 (1.0 g) was dissolved in anhydrous acetonitrile (11.3 mL) at RT under argon atmosphere and benzaldehyde dimethylacetal (880 μL, 5.84 mmol, 2 eq) and camphorsulfonic acid (7 mg, 0.029 mmol, 0.01 eq) were added. After 2.5 h (TLC: cyclohexane/ethyl acetate, 1:2), the reaction was quenched with triethylamine, and the solvents were evaporated in vacuo to give 1.5 g of colorless oil. The crude product was purified by column chromatography on silica gel (cyclohexane/ethyl acetate) to afford 10 (1.09 g, 2.53 mmol, 87%). $[\alpha]_D^{20}$=−49.4° (c=1.0, $CH_2Cl_2$); IR ($CH_2Cl_2$): 3410, 2963, 2870, 1384, 1264, 1082, 1072, 1029, 1003, 972 $cm^{-1}$; $^1$H-NMR (400 MHz, $CDCl_3$) δ 7.61 (1H, d, J 2.0 Hz, Ar—H), 7.51-7.46 (2H, m, Ar—H), 7.39-7.35 (m, 3H, Ar—H), 7.29-7.23 (m, 2H, Ar—H), 7.16 (1H, d, J=8.0, Ar—H), 5.54 (1H, s, benzylidene-H), 4.64 (1H, d, J 10.0, 1-H), 4.36 (1H, dd, $J_1$ 10.3, $J_2$ 4.5, 6-Ha), 3.90-3.73 (2H, m, 3-H, 6-Hb), 3.59-3.47 (3H, m, 2-H, 4-H, 5-H), 2.86 (1H, d, J 2.2, OH), 2.69 (1H, d, J 2.4, OH), 2.42 (3H, s, $CH_3$), 1.32 (9H, s, t-Bu); $^{13}$C-NMR (100 MHz, $CDCl_3$) δ 149.7, 137.1, 137.0, 131.0, 130.3, 130.2, 129.4, 128.5, 126.4, 125.5 (C-aromatic), 102.0 (C-benzylidene), 88.8 (C-1), 80.4 (C-2), 74.8 (C-3), 73.0 (C-4), 70.5 (C-5), 68.7 (C-6), 31.4 (tBu), 20.6 ($CH_3$); HRMS (ESI): Calcd for $C_{24}H_{30}O_5S$ $[M+Na]^+$ 453.1706. found 453.1714.

(2-Methyl-5-tert-butylphenyl)-4,6-O-benzylidene-3-O-tert-butyldimethylsilyl-1-thio-β-D-glucopyranoside (11)

Compound 10 (658 mg, 1.53 mmol) and imidazole (208 mg, 3.06 mmol, 2 eq) were dissolved in anhydrous DMF (880 μL). TBSCl (346 mg, 2.29 mmol, 1.5 eq) was gradually added with stirring. After 4 h, the solvent was evaporated and the resulting oil was dissolved in DCM. The solution was extracted with 1 M HCl and saturated aqueous $NaHCO_3$ solution, the organic layer was dried over $MgSO_4$ and the solvent was evaporated in vacuo. The colorless solid was dried in high vacuum and the crude product (820 mg) was purified using flash column chromatography (cyclohexane/ethyl acetate) to afford 11 (573 mg, 1.05 mmol, 69%). $[\alpha]_D^{20}$=−49.1° (c=1.0, $CH_2Cl_2$); IR ($CH_2Cl_2$): 3559, 2957, 2928, 2858, 1631, 1383, 1259, 1110, 1086, 1067, 1009 $cm^{-1}$; $^1$H-NMR (400 MHz, $CDCl_3$) δ 7.61 (1H, d, J 2.1, Ar—H), 7.51-7.46 (2H, m, Ar—H), 7.39-7.33 (3H, m, Ar—H), 7.26-7.22 (1H, m, Ar—H), 7.15 (1H, d, J 8.0, Ar—H), 5.52 (1H, s, benzylidene-H), 4.65 (1H, d, J 9.8, 1-H), 4.34 (1H, dd, $J_1$ 10.4, $J_2$ 4.4, 6-Ha), 3.84-3.74 (2H, m, 6-Hb, 3-H), 3.54-3.45 (3H, m, 4-H, 5-H, 2-H), 2.42 (3H, s, $CH_3$), 1.31 (9H, s, tBu), 0.88 (9H, s, tBu), 0.11 (3H, s, $CH_3$), 0.04 (3H, s, $CH_3$); $^{13}$C-NMR (100 MHz, $CDCl_3$) δ 149.7, 137.3, 137.0, 131.4, 130.1, 130.1, 129.1, 128.3, 126.3, 125.3 (C-aromatic), 101.8 (C-benzylidene), 89.0 (C-1), 81.2 (C-4), 76.2 (C-3), 74.0 (C-2), 70.8 (C-5), 68.8 (C-6), 31.4 (tBu), 26.0 (tBu), 20.6 ($CH_3$), −4.2 ($CH_3$), −4.6 ($CH_3$); HRMS (ESI): Calcd for $C_{30}H_{44}O_5SSi$ $[M+Na]^+$ 567.2571. found 567.2584.

(2-Methyl-5-tert-butylphenyl) 4,6-O-benzylidene-2-O-benzyl-1-thio-β-D-glucopyranoside (12)

To a solution of 11 (2.00 g, 3.67 mmol) in anhydrous DMF (20 ml), NaH (0.21 g, 8.81 mmol) and BnBr (1.31 ml, 11.01 mmol) were added at 0° C. The mixture was warmed to room temperature and stirred over night. Then cooled to 0° C., quenched with MeOH and diluted with $Et_2O$. The organic layers were washed with $H_2O$ and brine, dried over $MgSO_4$ and concentrated. Column chromatography on silica gel (hexanes/ethyl acetate) afforded crude (2-methyl-5-tert-butylphenyl) 4,6-O-benzylidene-2-O-benzyl-3-O-tert-butyldimethylsilyl-1-thio-β-D-glucopyranoside S2 (2.4 g), which was taken directly to the next step. Crude S2 (2.4 g) was dissolved in THF (30 ml), cooled to 0° C. and treated with a solution of TBAF (1 M in THF, 7.24 ml, 7.24 mmol). The mixture was warmed to room temperature over night and concentrated. Column chromatography on silica gel (hexanes/ethyl acetate) afforded 12 (1.77 g, 3.40 mmol, 93%). $[\alpha]_D^{20}$=−11.4° (c=3.7, $CHCl_3$), IR $v_{max}$ (film) 3463, 3033, 2962, 1810, 1670, 1602, 1488, 1455, 1384, 1264, 1215, 1088 $cm^{-1}$; $^1$H-NMR (400 MHz, $CDCl_3$) δ 7.64-7.61 (1H, m, Ar—H), 7.51-7.20 (11H, m, Ar—H), 7.17-7.12 (1H, m, Ar—H), 5.55 (1H, s, benzylidene-H), 4.99 (1H, d, A of AB, $J_{AB}$ 10.9, —$CH_2$—Bn), 4.84 (1H, d, B of AB, $J_{AB}$ 10.9, —$CH_2$—Bn), 4.75 (1H, d, J 9.8, 1-H), 4.34 (1H, dd, $J_1$ 10.5, $J_2$ 5.0, 6-Ha), 3.97-3.89 (1H, m, 3-H), 3.81 (1H, dd, $J_1$ $J_2$ 10.3, 6-Hb), 3.60 (1H, dd, $J_1$ $J_2$ 9.4, 4-H), 3.55-3.42 (2H, m, 2-H, 5-H), 2.52 (1H, d, J 2.4, 3-OH), 2.42 (3H, s, $CH_3$), 1.31 (9H, s, tBu); $^{13}$C-NMR (100 MHz, $CDCl_3$) δ 149.7, 138.1, 137.1, 136.3, 132.8, 130.1, 129.4, 129.1, 128.7, 128.5, 128.4, 128.2, 126.4, 125.0, 102.0, 88.2 (C-1), 81.1 (C-2), 80.5 (C-4), 75.7, 75.6 (C-3), 70.1 (C-5), 68.8 (C-6), 34.6, 31.5, 20.5; HRMS (ESI): Calcd for $C_{31}H_{36}O_5S$ $[M+Na]^+$ 543.2181. found 543.2181.

(2-Methyl-5-tert-butylphenyl) 4,6-O-benzylidene-2-O-benzyl-3-O-fluorenylmethoxycarbonyl-1-thio-β-D-glucopyranoside (13)

To a solution of 12 (415 mg, 0.80 mmol) and pyridine (129 μl) in DCM (5 ml), Fmoc-Cl (309 mg, 1.20 mmol) was added and the mixture was stirred over night, diluted with DCM and the organic layers were washed with a 0.01 M HCl solution and saturated aqueous $NaHCO_3$ solution. The organic layer was dried over $MgSO_4$ and concentrated. Column chromatography on silica gel (hexanes/ethyl acetate) afforded 13 (561 mg, 0.76 mmol, 95%) as a white solid. $[\alpha]_D^{20}$=−0.3° (c=5.9, $CHCl_3$), IR $v_{max}$ (film) 3033, 2961, 1955, 1754, 1605, 1451, 1385, 1251, 1077 $cm^{-1}$; $^1$H-NMR (400 MHz, $CDCl_3$) δ 7.79-7.73 (2H, m, Fmoc-H), 7.65-7.13 (19H, m, Ar—H), 5.55 (1H, s, benzylidene-H), 5.29-5.22 (1H, m), 4.98 (1H, A of AB, $J_{AB}$ 10.7, —$CH_2$—Bn), 4.82 (1H, d, J 9.8, H-1), 4.72 (1H, B of AB, J 10.7, —$CH_2$—Bn), 4.49-4.42 (1H, m), 4.40-4.28 (2H, m), 4.24-4.18 (1H, m), 3.88-3.67 (3H, m), 3.60-3.52 (1H, m), 2.42 (3H, s, $CH_3$), 1.31 (9H, s, tBu); $^{13}$C-NMR (100 MHz, $CDCl_3$) δ 154.6, 149.8, 143.5, 143.3, 141.4, 137.5, 136.9, 136.6, 130.2, 129.6, 129.2, 128.4, 128.3, 128.2, 128.00, 127.97, 127.30, 127.27, 126.3, 126.2, 125.2, 120.1, 101.6, 88.7 (C-1), 79.5, 79.3, 78.5, 75.7, 70.33, 70.27, 68.8, 46.8, 34.6, 31.4, 20.5; HRMS (ESI): Calcd for $C_{46}H_{46}O_7S$ $[M+Na]^+$ 765.2862. found 765.2886.

(2-Methyl-5-tert-butylphenyl)-2,6-di-O-benzyl-3-O-fluorenylmethoxycarbonyl-1-thio-β-D-glucopyranoside (14)

To a solution of 13 (100 mg, 0.14 mmol) in anhydrous DCM (3 ml) freshly activated molecular sieves (4 Å) were added. The mixture was cooled to −78° C., TES (64 μl, 0.40 mmol) and TfOH (41 μl, 0.46 mmol) were added. After stirring for 3 hours at −78° C. the reaction was quenched by the addition of pyridine, diluted with DCM and washed with a saturated aqueous $NaHCO_3$ solution. The organic phase was then dried over $MgSO_4$, filtered and concentrated. Column chromatography on silica gel (hexanes/ethyl acetate) afforded 14 (73 mg, 0.10 mmol, 73%). $[\alpha]_D^{20}$=+10.5° (c=4.9, CHCl$_3$), IR $\nu_{max}$ (film) 3486, 3031, 2959, 1951, 1750, 1604, 1451, 1387, 1254, 1054 cm$^{-1}$; $^1$H-NMR (400 MHz, CDCl$_3$) δ 7.80-7.74 (2H, m, Fmoc-H), 7.66-7.56 (3H, m, Ar—H), 7.44-7.09 (16H, m, Ar—H), 4.95 (1H, dd, J$_1$ J$_2$ 9.2, 3-H), 4.92 (1H, d, J 10.7, —CH$_2$—Bn), 4.69 (1H, d, J 9.8, 1-H), 4.68 (1H, d, J 10.8, —CH$_2$—Bn), 4.61 (1H, A of AB, J$_{AB}$ 12.0, —CH$_2$-Bn), 4.55 (1H, B of AB, J$_{AB}$ 12.0, —CH$_2$—Bn), 4.50-4.43 (1H, m, Fmoc-CH$_2$), 4.40-4.31 (1H, m, Fmoc-CH$_2$), 4.26-4.20 (1H, m, Fmoc-CH), 3.84 (1H, ddd, J$_1$ J$_2$ 9.5, J$_3$ 3.6, 4-H), 3.81-3.74 (2H, m, 6-H), 3.61 (1H, dd, J$_1$ J$_2$ 9.5, 2-H), 3.56-4.49 (1H, m, 5-H), 2.97 (1H, d, J 3.6, 4-OH), 2.40 (1H, s, CH$_3$), 1.26 (9H, s, tBu); $^{13}$C-NMR (100 MHz, CDCl$_3$) δ 155.7, 149.8, 143.5, 143.4, 141.4, 137.7, 137.6, 136.5, 132.8, 130.1, 129.5, 128.6, 128.4, 128.2 128.04, 127.98, 127.9, 127.3, 125.3, 125.2, 125.0, 120.2, 88.1 (C-1), 83.2 (C-3), 78.5 (C-2), 77.8 (C-5), 75.4, 73.9, 71.0 (C-4), 70.4, 70.3 (C-6), 46.9, 34.6, 31.4, 20.5; HRMS (ESI): Calcd for C$_{46}$H$_{48}$O$_7$S [M+Na]$^+$ 767.3018. found 767.3038.

(2-Methyl-5-tert-butylphenyl)-2,6-di-O-benzyl-3-O-fluorenylmethoxycarbonyl-4-O-levulinoyl-1-thio-β-D-glucopyranoside (3)

To a solution of 14 (480 mg, 0.64 mmol) in DCM (8 ml) and pyridine (0.3 ml) Lev$_2$O (55 mg, 0.26 mmol) was added and stirred for three days. The mixture was diluted with DCM and washed with a 1 M HCl solution and with saturated aqueous NaHCO$_3$ solution. The organic layers were dried over MgSO$_4$ and concentrated. Column chromatography on silica gel (hexanes/ethyl acetate) afforded 3 (428 mg, 0.51 mmol, 79%). [α]$_D^{20}$=+19.2° (c=1.0, CHCl$_3$), IR $\nu_{max}$ (film) 3065, 2955, 1754, 1719, 1604, 1488, 1452, 1363, 1259, 1152, 1070, 1039 cm$^{-1}$; $^1$H-NMR (400 MHz, CDCl$_3$) δ 7.80-7.74 (2H, m, Ar—H), 7.68-7.58 (3H, m, Ar—H), 7.44-7.15 (15H, m, Ar—H), 7.15-7.11 (1H, m, Ar—H), 5.20 (1H, dd, J$_1$ J$_2$ 9.7, 4-H), 5.15-5.07 (1H, m, 3-H), 4.95 (1H, A of AB, J$_{AB}$ 10.8, —CH$_2$—Bn), 4.71 (1H, d, J 9.8, 1-H), 4.69 (1H, B of AB, J$_{AB}$ 10.4, —CH$_2$—Bn), 4.56-4.41 (3H, m), 4.29-4.20 (2H, m), 3.74-3.55 (4H, m, 2-H, 4-H, 6-H), 2.60-2.52 (2H, m, Lev-CH$_2$), 2.42 (3H, s, Lev-CH$_3$), 2.41-2.32 (2H, m, Lev-CH$_2$), 2.02 (3H, s, SPhCH$_3$), 1.26 (9H, s, tBu); $^{13}$C-NMR (100 MHz, CDCl$_3$) δ 206.0, 171.6, 154.8, 149.9, 143.7, 143.5, 141.4, 141.3, 138.0, 137.6, 136.6, 132.7, 130.1, 129.5, 128.4, 128.2, 128.1, 128.0, 127.9, 127.7, 127.4, 127.3, 125.5, 125.4, 125.0, 120.1, 88.2, 80.5, 78.9, 77.3, 75.6, 73.7, 70.6, 69.4, 69.2, 46.7, 37.8, 34.6, 31.4, 29.7, 28.0, 20.5; HRMS (ESI): Calcd for C$_{51}$H$_{54}$O$_9$S [M+Na]$^+$ 865.3386 found 865.3412.

(2-Methyl-5-tert-butylphenyl) 2-O-benzoyl-4,6-O-benzylidene-3-O-tert-butyldimethylsilyl-1-thio-β-D-glucopyranoside (15)

Thioglycoside 12 (1.00 g, 1.84 mmol) was dissolved under argon in anhydrous pyridine (4 mL). DMAP (67 mg, 0.55 mmol) was added and the solution was cooled to 0° C. BzCl (639 μL, 5.51 mmol) was added dropwise and the solution was heated to 70° C. and stirred for 12 h. After completion (TLC: cyclohexane/ethyl acetate, 9:1), the reaction was quenched with methanol. The suspension was diluted with DCM and extracted with 1 M HCl and H$_2$O. Column chromatography on silica gel (hexanes/ethyl acetate) afforded 15 (1.05 g, 1.62 mmol, 88%). [α]$_D^{20}$=+22.9° (c=1.0, CH$_2$Cl$_2$); IR (CH$_2$Cl$_2$): 2959, 2929, 2858, 1732, 1384, 1266, 1096, 1069 cm$^{-1}$; $^1$H-NMR (400 MHz, CDCl$_3$) δ 8.08 (2H, dd, J 8.3, Ar—H), 7.56 (1H, d, J 1.8, Ar—H), 7.52-7.43 (5H, m, Ar—H), 7.37 (3H, dd, J$_1$ 5.2, J$_2$ 2.0, Ar—H), 7.20 (1H, dd, J$_1$ 8.0, J$_2$ 2.1, Ar—H), 7.07 (1H, d, J 8.0, Ar—H), 5.58 (1H, s, benzylidene-H), 5.35 (1H, dd, J$_1$ 10.3, J$_2$ 8.6, 2-H), 4.84 (1H, d, J 10.3, 1-H), 4.38 (1H, dd, J$_1$ 10.5, J$_2$ 5.0, 6-Ha), 4.06 (1H, dd, J$_1$ J$_2$ 8.9, 3-H), 3.88 (1H, dd, J$_1$ 10.3, J$_2$ 5.0, 6-Hb), 3.69 (1H, dd, J$_1$ J$_2$ 9.1 Hz, 4-H), 3.60-3.52 (1H, m, 5-H), 2.18 (3H, s, CH$_3$), 1.28 (9H, s, tBu), 0.70 (9H, s, tBu), −0.05 (3H, s, CH$_3$), −0.14 (3H, s, CH$_3$); $^{13}$C-NMR (100 MHz, CDCl$_3$) δ 133.1, 129.9, 129.8, 129.4, 129.1, 128.3, 128.1, 126.2, 125.1 (C—Ar), 101.9 (C-benzylidene), 88.1 (C-1), 81.3 (C-4), 74.3 (C-3), 73.6 (C-2), 70.6 (C-5), 68.7 (C-6), 31.3 (tBu), 25.5 (tBu), 20.2 (CH$_3$), −4.2 (CH$_3$), −5.0 (CH$_3$); HRMS (ESI): Calcd for C$_{37}$H$_{48}$O$_6$SSi [M+Na]$^+$ 671.2833. found 671.2852.

(2-Methyl-5-tert-butylphenyl) 2-O-benzoyl-4,6-O-benzylidene-1-thio-β-D-glucopyranoside (16)

To a solution of 15 (200 mg, 0.31 mmol) in DMF (1 mL) a solution of TBAF.3H$_2$O (683 mg, 1.85 mmol) and glacial acetic acid (124 μL, 2.16 mmol) in DMF (1 mL) were added. The mixture was warmed to 35° C. for 9 h, diluted with ether and washed with a 0.01 M HCl solution and saturated aqueous NaHCO$_3$ solution. The organic layer was dried over MgSO$_4$ and concentrated. Column chromatography on silica gel (hexanes/ethyl acetate) afforded 16 (150 mg, 0.28 mmol, 91%). [α]$_D^{20}$=−5.5° (c=0.8, CHCl$_3$); IR (CHCl$_3$): 3455, 2963, 2870, 1729, 1268, 1100, 1071 cm$^{-1}$; $^1$H-NMR (400 MHz, CDCl$_3$) δ 8.11 (2H, d, J 7.4, Ar—H), 7.64-7.33 (9H, m, Ar—H), 7.27-7.20 (1H, m, Ar—H), 7.10 (1H, d, J 8.0, Ar—H), 5.59 (1H, s, benzylidene-H), 5.25 (1H, dd, J$_1$ 10.1, J$_2$ 8.7, 2-H), 4.88 (1H, d, J 10.1, 1-H), 4.40 (1H, dd, J$_1$ 10.5, J$_2$ 5.0, 6-Ha), 4.09 (1H, dd, J$_1$ 9.0, J$_2$=8.7, 3-H), 3.87 (1H, dd, J$_1$ 10.4, J$_2$ 5.0, 6-Hb), 3.71 (1H, dd, J$_1$ 9.0, J$_2$ 9.7, 4-H), 3.57 (1H, td, J$_1$ 9.7, J$_2$ 5.0, 5-H), 2.83 (1H, br, 3-OH), 2.23 (3H, s, CH$_3$), 1.29 (9H, s, tBu); $^{13}$C-NMR (100 MHz, CDCl$_3$) δ 166.1 (C=O benzoyl), 149.7, 137.32, 136.9, 133.6, 131.9, 130.4, 130.2, 129.5, 128.6, 128.5, 126.4, 125.6 (aromatics), 102.1 (C-benzylidene), 87.5 (C-1), 80.9 (C-4), 74.0 (C-3), 73.6 (C-2), 70.5 (C-5), 68.7 (C-6), 31.4 (tBu), 20.4 (CH$_3$); HRMS (ESI): Calcd for C$_{31}$H$_{34}$O$_6$S [M+Na]$^+$ 557.1968. found 557.1975.

(2-Methyl-5-tert-butylphenyl) 2-O-benzoyl-4,6-O-benzylidene-3-O-fluorenylmethoxycarbonyl-1-thio-β-D-glucopyranoside (17)

To a solution of 16 (277 mg, 0.52 mmol) and pyridine (130 μl) in DCM (4 ml), Fmoc-Cl (268 mg, 1.04 mmol) was added and the mixture stirred over night, diluted with DCM and the organic layers were washed with a 0.01 M HCl solution and saturated aqueous NaHCO$_3$ solution. The organic layer was dried over MgSO$_4$ and concentrated. Column chromatography on silica gel (hexanes/ethyl acetate) afforded 17 (378 mg, 0.50 mmol, 96%). [α]$_D^{20}$=+50.2° (c=4.5, CHCl$_3$), IR $\nu_{max}$ (film) 3066, 2961, 1752, 1732, 1602, 1488, 1450, 1385, 1316, 1268, 1250, 1093 cm$^{-1}$; $^1$H-NMR (400 MHz, CDCl$_3$) δ 8.06-7.99 (2H, m, Ar—H), 7.73-7.67 (2H, m, Ar—H), 7.61-7.07 (19H, m, Ar—H), 5.60 (1H, s, benzylidene-H), 5.51-5.36 (2H, m, 2-H, 3-H), 4.95 (1H, d, J 9.9, 1-H), 4.46-4.39 (1H, m, 6-H), 4.27-4.16 (2H, m, Fmoc-CH$_2$), 4.06-4.00 (1H, m, Fmoc-CH), 3.98-3.88 (2H, m, 4-H, 6-H), 3.72-3.63 (1H, m, 5-H) 2.23 (1H, s, CH$_3$), 1.29 (9H, s, tBu); $^{13}$C-NMR (100 MHz, CDCl$_3$) δ 165.3, 154.6, 149.8, 143.4, 143.2, 141.3, 141.2, 137.4, 136.8, 133.6, 131.7, 130.5, 130.2, 130.1, 129.3, 129.2, 128.5, 128.3, 127.9, 127.27, 127.25, 126.3, 125.8, 125.3, 125.1, 120.00, 119.99, 101.8, 88.0 (C-1), 78.3 (4-H), 77.3 (C-3), 71.4 (C-2), 70.8 (C-5), 70.5, 68.7 (C-6), 46.6, 34.6, 31.7, 31.4, 20.4, 14.3; HRMS (ESI): Calcd for $C_{46}H_{44}O_8S$ [M+Na]$^+$ 779.2655. found 779.2649.

Dibutyl-2-O-benzoyl-4,6-O-benzylidene-3-O-fluorenyl-methoxycarbonyl-D-gluco-pyranosidephosphate (4)

Thioglucoside 17 (690 mg, 0.91 mmol) was coevaporated with toluene three times and dried in vacuo, then dissolved in anhydrous DCM (10 ml). Freshly activated molecular sieves (4 Å) and dibutyl hydrogen phosphate (542 µl, 2.73 mmol) were added and the solution cooled to 0° C. NIS (246 mg, 1.09 mmol), followed by TfOH (10 µl, 0.11 mmol) was added and stirred at 0° C. for one hour. The reaction was quenched by the addition of pyridine, diluted with DCM and washed with aqueous $Na_2S_2O_3$ and saturated aqueous $NaHCO_3$ solutions. The organic phase was dried over $MgSO_4$, filtered and concentrated. The crude product was purified by column chromatography on silica gel (hexanes/ethyl acetate) to afford 4 (583 mg, 0.74 mmol, 81%) in a mixture of α/β-anomers (α/β=1:4). NMR data are reported for the β-anomer. $[α]_D^{20}$=+8.9° (c=3.1, CHCl$_3$), IR $ν_{max}$ (film) 3067, 2961, 1755, 1733, 1602, 1451, 1268, 1096, 1026 cm$^{-1}$; H-NMR (400 MHz, CDCl$_3$) δ 8.06-7.99 (2H, m, Ar—H), 7.72-7.66 (2H, m, Ar—H), 7.55-7.29 (12H, m, Ar—H), 7.18-7.11 (2H, m, Ar—H), 5.60-5.54 (2H, m, benzylidene, 1-H), 5.50 (1H, dd, J$_1$ J$_2$ 9.4, 2-H), 5.36 (1H, dd, J$_1$ J$_2$ 9.4, 3-H), 4.49-4.41 (1H, m, 6-H), 4.30-4.18 (2H, m, Fmoc-CH$_2$), 4.10-4.01 (3H, m, Fmoc-H, phosphate-CH$_2$), 4.00-3.94 (1H, m, 4-H), 3.90-3.86 (1H, m, 6-H), 3.82-3.67 (3H, m, phosphate-CH$_2$, 5-H), 1.67-1.60 (2H, m, phosphate-CH$_2$), 1.42-1.25 (4H, m, phosphate-CH$_2$), 1.10-1.01 (2H, m, phosphate-CH$_2$), 0.92 (3H, t, J 7.4, phosphate-CH-3), 0.70 (3H, t, J 7.4, phosphate-CH$_3$); $^{13}$C-NMR (100 MHz, CDCl$_3$) δ 165.1, 154.5, 143.4, 143.1, 141.3, 136.6, 133.8, 130.1, 129.4, 128.6, 128.4, 127.9, 127.2, 126.3, 125.3, 125.2, 120.0, 101.9, 96.91, 96.86, 78.1, 77.5, 77.2, 76.8, 75.8, 72.6, 70.6, 68.4, 68.1, 67.1, 46.6, 32.2, 32.1, 32.0, 31.9, 18.7, 18.4, 13.7, 13.5; δ$_P$ (160 MHz, CDCl$_3$) -2.95; HRMS (ESI): Calcd for $C_{43}H_{47}O_{12}P$ [M+Na]$^+$ 809.2703. found 809.2690.

4-Methoxyphenyl-2,3-di-O-benzoyl-4-O-benzyl-α-L-rhamnopyranoside (19)

Rhamnoside 18 (500 mg, 1.39 mmol) was dissolved in a solution of DCM (1 ml) and pyridine (1 ml). DMAP (68 mg, 0.56 mmol) was added and the mixture cooled to 0° C., then BzCl (780 mg, 5.56 mmol) was added and the reaction warmed to room temperature over night. The reaction was quenched with MeOH, diluted with DCM and the organic layer was washed with a 0.01 M HCl solution and saturated aqueous NaHCO$_3$ solution. The organic layer was dried over MgSO$_4$ and concentrated. Column chromatography on silica gel (hexanes/ethyl acetate) afforded 19 (768 g, 1.35 mmol, 97%). $[α]_D^{20}$=+17.6° (c=3.1, CHCl$_3$), IR $ν_{max}$ (film) 3064, 2934, 1725, 1602, 1506, 1452, 1363, 1273, 1213, 1094, 1027 cm$^{-1}$; $^1$H-NMR (400 MHz, CDCl$_3$) δ 8.11-8.05 (2H, m, Ar—H), 7.98-7.93 (2H, m, Ar—H), 7.67-7.61 (1H, m, Ar—H), 7.56-7.49 (3H, m, Ar—H), 7.40-7.35 (2H, m, Ar—H), 7.25-7.16 (5H, m, Ar—H), 7.08-7.03 (2H, m, Ar—H), 6.87-6.82 (2H, m, Ar—H), 5.94 (1H, dd, J$_1$ 9.6, J$_2$ 3.4, 3-H), 5.79 (1H, dd, J$_1$ 3.4, J$_2$1.9, 2-H), 5.54 (1H, d, J 1.8, 1-H), 4.75 (1H, A of AB, J$_{AB}$ 10.9, —CH$_2$—Bn), 4.68 (1H, B of AB, J$_{AB}$ 10.9, —CH$_2$—Bn), 4.20-4.11 (1H, m, 5-H), 3.88 (1H, dd, J$_1$ J$_2$ 9.6, 4-H), 3.78 (3H, s, —CH$_3$), 1.41 (3H, d, J 6.2, 6-H); $^{13}$C-NMR (100 MHz, CDCl$_3$) δ 165.58, 165.55, 155.21, 150.20, 137.7, 133.6, 133.3, 130.0, 129.9, 129.8, 129.71, 128.69, 128.53, 128.48, 128.2, 128.0, 117.9, 114.7, 96.6 (C-1), 79.1 (C-4), 75.3, 72.3 (C-3), 71.2 (C-2), 68.5 (C-5), 55.8, 18.3 (C-6); HRMS (ESI): Calcd for $C_{34}H_{32}O_8$ [M+Na]$^+$ 591.1995. found 591.1985.

2,3-Di-O-benzoyl-4-O-benzyl-α-L-rhamnopyranoside-N-phenyl-trifluoroacetimidate (5)

CAN (2.17 g, 3.96 mmol) was added to a mixture of 19 (750 mg, 1.32 mmol) in MeCN (12 ml) and H$_2$O (12 ml) and stirred vigorously for 2 h. H$_2$O and EtOAc were added, the layers separated, the organic layer washed with H$_2$O and brine, dried over MgSO$_4$ and concentrated. Column chromatography on silica gel (hexanes/ethyl acetate) afforded the lactol as an orange solid (548 mg). A solution of the lactol (548 mg) in DCM (10 ml) was cooled to 0° C., CF$_3$C(NPh)Cl (438 mg, 2.11 mmol) and Cs$_2$CO$_3$ (688 mg, 2.11 mmol) were added and the resulting solution was stirred overnight at room temperature, diluted with DCM, filtered through a plug of celite and concentrated. Column chromatography on silica gel (hexanes/ethyl acetate) afforded 5 (619 mg, 0.98 mmol, 74%). $[α]_D^{20}$=+41.2° (c=4.8, CHCl$_3$), IR $ν_{max}$ (film) 3065, 2981, 1727, 1600, 1490, 1452, 1270, 1208, 1164, 1091 cm$^{-1}$; $^1$H-NMR (400 MHz, CDCl$_3$) δ 8.07-8.02 (2H, m, Ar—H), 7.96-7.89 (2H, m, Ar—H), 7.66-7.60 (1H, m, Ar—H), 7.57-7.46 (3H, m, Ar—H), 7.40-7.19 (9H, m, Ar—H), 7.40-7.19 (9H, m, Ar—H), 7.14-7.07 (1H, m, Ar—H), 6.91-6.82 (2H, m, Ar—H), 6.35 (1H, bs, 1-H), 5.84 (1H, s, 2-H), 5.77 (1H, dd, J$_1$ 9.4, J$_2$ 3.3, 3-H), 5.35 (1H, dd, J$_1$ 3.7, J$_2$ 1.9, 1-H), 4.76 (1H, A of AB, J$_{AB}$ 10.9, —CH$_2$—Bn), 4.68 (1H, B of AB, J$_{AB}$ 10.9, —CH$_2$-Bn), 4.21-4.08 (1H, m, 5-H), 3.87 (1H, dd, J$_1$ J$_2$ 9.5, 4-H), 1.48 (3H, d, J 6.1, 6-H); $^{13}$C-NMR (100 MHz, CDCl$_3$) δ 165.5, 165.3, 143.4, 137.4, 133.7, 133.4, 130.0, 129.8, 129.7, 129.4, 128.9, 128.7, 128.58, 128.57, 128.3, 128.2, 124.6, 119.6, 94.1 (C-1), 78.5 (C-4), 75.5, 72.0 (C-3), 70.7 (C-3), 69.6 (C-2), 18.4 (C-6); HRMS (ESI): Calcd for $C_{35}H_{30}F_3NO_7$ [M+Na]$^+$ 656.1872, found 656.1852.

N-(Benzyl)benzyloxycarbonyl-5-amino-pentanyl 2,6-di-O-benzyl-3-O-fluorenylmethoxycarbonyl-4-O-levulinoyl-α-D-glucopyranosyl-(1→2)-3,4,6-tri-O-benzyl-α-D-glucopyranoside (20)

Glucoside donor 3 (326 mg, 0.34 mmol) and glucoside acceptor 2 (262 mg, 0.35 mmol) were coevaporated with toluene three times and dried in vacuo. The mixture was dissolved in anhydrous Et$_2$O (3 ml), NIS (93 mg, 0.41 mmol) was added and cooled to −35° C. TfOH (3.7 µl, 41 µmol) was added and the mixture was stirred and warmed up to −10° C. in one hour. The reaction was quenched by the addition of pyridine, diluted with DCM and washed with aqueous Na$_2$S$_2$O$_3$ and saturated aqueous NaHCO$_3$ solutions. The phases were separated and the aqueous phase was extracted with DCM. The combined organic phases were dried over MgSO$_4$, filtered and concentrated. The crude product was purified by column chromatography on silica gel (hexanes/ethyl acetate) to afford 20 (343 mg, 0.24 mmol, 70%). $[α]_D^{20}$=+64.4° (c=5.9), IR $ν_{max}$ (film) 3032, 2932, 1755, 1700, 1605, 1497, 1452, 1362, 1259 cm$^{-1}$; $^1$H-NMR (400 MHz, CDCl$_3$) δ 8.00-6.90 (43H, m, Ar—H), 5.41 (1H, dd, J$_1$ J$_2$ 9.7), 5.26 (1H, dd, J$_1$ J$_2$ 9.8), 5.18-5.10 (2H, m), 5.06 (1H, bs, anomeric-H), 5.03-4.96 (2H, m, anomeric-H), 4.88 (1H, app d, J 11.0), 4.82 (1H, app d, J 10.8), 4.68-4.58 (3H, m), 4.52-4.41 (5H, m), 4.39-4.30 (2H, m), 4.26 (1H, app t, J 7.5), 4.14-4.08 (1H, m), 4.07-4.01 (1H, m), 3.82 (1H, dd, J$_1$ 9.9, J$_2$ 3.4), 3.80-3.56 (6H, m), 3.34-3.31 (2H, m), 3.28-3.06 (4H, m), 2.54-2.42 (2H, m), 2.32-2.17 (2H, m), 2.00 (1H, s, Lev- CH₃), 1.65-1.50 (4H, m, linker-CH₂—), 1.30-1.23 (4H, m, linker-CH₂—); ¹³C-NMR (100 MHz, CDCl₃) δ 206.0, 171.5, 154.9, 143.7, 143.6, 141.40, 141.35, 138.0, 137.8, 128.6, 128.54, 128.53, 128.39, 128.37, 128.2, 128.1, 128.0, 127.94, 127.87, 127.74, 127.66, 127.5, 127.3, 126.3, 125.5, 120.1, 120.0, 95.6 (C-anomeric), 94.0 (C-anomeric), 80.7, 78.2, 77.4, 77.0, 76.8, 76.2, 75.9, 75.4, 73.7, 73.5, 72.4, 70.5, 70.3, 68.8, 68.6, 68.4, 67.3, 46.8, 37.8, 31.4, 29.8, 27.9, 23.7; HRMS (ESI): Calcd for C₈₇H₉₁NO₁₇ [M+Na]⁺ 1444.6179. found 1444.6128.

N-(Benzyl)benzyloxycarbonyl-5-amino-pentanyl-2,6-di-O-benzyl-3-O-fluorenylmethoxycarbonyl-α-D-glucopyranosyl-(1→2)-3,4,6-tri-O-benzyl-α-D-glucopyranoside (21)

To a solution of 20 (224 mg, 0.16 mmol) in DCM (4.5 ml) hydrazine hydrate (31 μl, 0.63 mmol) dissolved in AcOH (0.4 ml) and pyridine (0.6 ml) was added and the solution stirred for 1 h. The reaction was then quenched by the addition of acetone and concentrated. Column chromatography on silica gel (hexanes/ethyl acetate) afforded 21 (196 mg, 0.15 mmol, 94%). [α]$_D^{20}$=+57.7° (c=1.7), IR ν$_{max}$ (film) 3423, 3031, 2926, 1753, 1697, 1605, 1586, 1497, 1452, 1422, 1362, 1255, 1068 cm⁻¹; ¹H-NMR (400 MHz, acetone-d6) δ 7.92-7.84 (2H, m, Ar—H), 7.78-7.64 (2H, m, Ar—H), 7.56-7.14 (35H, m, Ar—H), 5.44-5.37 (2H, m), 5.20-5.10 (3H, m), 5.07 (1H, d, J 10.7), 4.89-4.77 (3H, m), 4.66-4.47 (8H, m), 4.46-4.39 (2H, m), 4.27 (1H, app t, J 6.9), 4-20-4.14 (1H, m), 3.99 (1H, app t, J 9.3), 3.89-3.80 (2H, m), 3.78-3.59 (7H, m), 3.59-3.52 (1H, m), 3.49-3.42 (1H, m), 3.25-3.15 (2H, m), 2.82-2.79 (1H, m), 1.60-1.44 (4H, m, linker-CH₂—), 1.33-1.25 (2H, m, linker-CH₂—); ¹³C-NMR (100 MHz, acetone-d6) δ 155.9, 144.7, 144.6, 142.2, 142.1, 139.9, 139.8, 139.74, 139.68, 139.5, 139.4, 129.34, 129.26, 129.1, 129.02, 129.00, 128.9, 128.7, 128.62, 128.55, 128.5, 128.4, 128.20, 128.16, 128.14, 128.05, 128.0, 127.9, 126.1, 126.0, 120.88, 120.86, 96.3, 94.2, 81.8, 80.0, 79.2, 78.0, 76.5, 75.5, 73.8, 73.5, 72.1, 71.9, 71.5, 70.2, 70.08, 70.06, 69.5, 68.6, 67.4, 47.6, 27.5, 24.2; HRMS (ESI): Calcd for C₈₂H₈₅NO₁₅[M+Na]⁺ 1346.5817. found 1346.5784.

N-(Benzyl)benzyloxycarbonyl-5-amino-pentanyl-2-O-benzoyl-4,6-O-benzylidene-β-D-glucopyranosyl-(1→4)-2,6-di-O-benzyl-α-D-glucopyranosyl-(1→2)-3,4,6-tri-O-benzyl-α-D-glucopyranoside (23)

Phosphate 4 (74 mg, 94 μmol) and 21 (48 mg, 36 μmol) were coevaporated with toluene three times, dried in vacuo and then dissolved in anhydrous DCM (1.0 ml). Freshly activated molecular sieves (4 Å) were added and the mixture cooled to −30° C. TMSOTf (18 μl, 98 μmol) was added and then warmed to −7° C. over 1.5 h. The reaction was quenched with pyridine and concentrated in vacuo. Column chromatography on silica gel (toluene/acetone) afforded crude 22. 20% NEt₃ in DCM (1 ml) was added to crude 22 and stirred for 4 h, the mixture was concentrated in vacuo column chromatography on silica gel (toluene/acetone) afforded 23 (20 mg, 14 μmol, 38%). [α]$_D^{20}$=+8.1° (c=1.6), IR ν$_{max}$ (film) 3462, 3032, 2924, 1732, 1699, 1603, 1497, 1453, 1364, 1268, 1093 cm⁻¹; ¹H-NMR (400 MHz, CDCl₃) δ 8.05-7.92 (2H, m, Ar—H), 7.63-7.06 (43H, m, Ar—H), 5.56 (1H, s, benzylidene-H), 5.24 (1H, app t, J 8.5), 5.20-5.11 (2H, m), 5.09-4.98 (2H, m, anomeric-H), 4.88 (1H, app d, J 10.7), 4.79-4.66 (4H, m, anomeric-H), 4.62-4.54 (1H, m), 4.49-4.36 (5H, m), 4.19-4.05 (2H, m), 4.03-3.91 (2H, m), 3.89-3.44 (14H, m), 3.39-3.04 (4H, m), 1.57-1.36 (4H, m, linker-CH₂—), 1.32-1.14 (2H, m, linker-CH₂—); ¹³C-NMR (100 MHz, CDCl₃) δ 165.6, 138.51, 138.46, 138.4, 138.1, 136.8, 133.7, 130.1, 129.6, 129.4, 128.7, 128.6, 128.54, 128.52, 128.47, 128.45, 128.4, 127.98, 127.9, 127.84, 127.78, 127.7, 127.4, 126.4, 102.1, 101.7 (C-anomeric), 95.8 (C-anomeric), 94.5 (C-anomeric), 81.1, 80.8, 80.6, 78.2, 77.9, 77.4, 76.1, 75.2, 74.7, 73.6, 73.4, 72.8, 72.1, 71.6, 70.4, 69.5, 68.7, 68.4, 68.2, 67.8, 67.3, 66.4, 29.8, 29.4, 23.6; HRMS (ESI): Calcd for C₈₇H₉₃NO₁₉ [M+Na]⁺ 1478.6239. found 1478.6136.

N-(Benzyl)benzyloxycarbonyl-5-amino-pentanyl 2,3-di-O-benzoyl-4-O-benzyl-α-L-rhamnopyranosyl-(13)-2-O-benzoyl-4,6-O-benzylidene-3-β-D-glucopyranosyl-(1→4)-[2,3-Di-O-benzoyl-4-O-benzyl-α-L-rhamnopyranosyl-(1→3)]-2,6-di-O-benzyl-α-D-glucopyranosyl-(1→2)-3,4,6-tri-O-benzyl-α-D-glucopyranoside (24)

Compounds 5 (26 mg, 41 μmol) and 23 (10 mg, 6.9 μmol) were coevaporated with toluene three times, dried in vacuo and dissolved in anhydrous DCM (1.0 ml). Freshly activated molecular sieves (4 Å) were added and the mixture cooled to −30° C. TMSOTf (10 μl of a solution of 7.4 μl TMSOTf in 93 μl DCM, 4.1 μmol) was added and the reaction was stirred at −30° C. for 1.5 h. The reaction was quenched with pyridine and concentrated in vacuo. Column chromatography on silica gel (toluene/acetone) afforded 24 (14 mg, 5.5 μmol, 81%). [α]$_D^{20}$=+5.2° (c=0.7), IR ν$_{max}$ (film) 3032, 2933, 1728, 1602, 1585, 1496, 1452, 1363, 1263, 1094, 1069 cm⁻¹; ¹H-NMR (400 MHz, CDCl₃) δ 8.20-6.90 (75H, m, Ar—H), 5.79-5.67 (3H, m), 5.46 (1H, s, benylidene-H), 5.33-5.29 (1H, m), 5.28-5.21 (1H, m), 5.17-5.08 (3H, m, anomeric-H), 5.02 (1H, bs, anomeric-H), 4.92-4.78 (4H, m, anomeric-H), 4.74-4.60 (4H, m), 4.59-4.49 (4H, m, anomeric-H), 4.48-4.44 (1H, m), 4.43-4.31 (4H, m), 4.29-4.13 (4H, m, anomeric-H), 4.03-3.88 (3H, m), 3.83-3.45 (13H, m), 3.40-3.02 (7H, m), 1.65 (1H, d, J 6.2, Rha-CH₃), 1.53-1.32 (4H, m, linker-CH₂—), 1.24-1.10 (2H, m, linker-CH₂—), 0.90 (1H, d, J 6.1, Rha-CH₃); ¹³C-NMR (100 MHz, CDCl₃) δ 165.6, 165.48, 165.5, 164.5, 164.2, 138.3, 137.8, 137.6, 133.1, 130.1, 130.0, 129.94, 129.85, 129.7, 129.4, 129.1, 129.0, 128.9, 128.83, 128.76, 128.7, 128.6, 128.51, 128.47, 128.45, 128.42, 128.36, 128.32, 128.29, 128.23, 128.17, 128.04, 128.00, 127.94, 127.88, 127.8, 127.7, 126.5, 126.4, 100.6 (C-anomeric), 100.5 (C-anomeric), 97.9 (C-anomeric), 97.5, 95.8 (C-anomeric), 93.5 (C-anomeric), 80.2, 79.2, 78.1, 77.5, 77.4, 77.2, 76.8, 76.2, 76.1, 76.0, 74.2, 74.0, 73.6, 72.9, 72.1, 71.6, 71.2, 70.9, 68.7, 67.4, 67.2, 50.6, 47.2, 46.2, 29.9, 23.6, 18.4, 17.5; HRMS (ESI): Calcd for C₁₄₁H₁₄₁NO₃₁ [M+Na]⁺ 2366.9385. found 2366.9440.

5-Amino-pentanyl α-L-rhamnopyranosyl-(1→3)-β-D-glucopyranosyl-(1→4)-[α-L-rhamnopyranosyl-(1→3)]-α-D-glucopyranosyl-(1→2)-α-D-glucopyranoside (1)

Fully protected pentasaccharide 24 (10 mg, 4.3 μmol) was dissolved in a solution of NaOMe (0.5 M) in THF/MeOH (1:1, 1 ml) and heated to 50° C. for 12 h. The mixture was neutralized with Amberlite IR 120 (H⁺) ion exchange resin, filtered and concentrated. Size exclusion chromatography on Sephadex LH-20 (CHCl₃/MeOH=1:1) afforded the de-benzoylated pentasaccharide (5.6 mg), which was dissolved in a mixture of MeOH (0.9 ml), H₂O (0.1 ml) and AcOH (25 μl). The solution was purged with Argon, 10% Pd/C (10 mg) was added and the solution purged with H₂ for 30 min, then stirred under an H₂ atmosphere for 12 h, filtered and concentrated.

Size exclusion chromatography on Sephadex LH-20 (MeOH) afforded 1 (2.3 mg, 2.6 µmol, 61%). NMR data are reported in Table 1, comparison with the data from native PS-I is reported in Table 2. HRMS (MALDI-TOF): Calcd for $C_{35}H_{63}NO_{24}$ [M+Na]$^+$ 904.3632. found 904.3606.

TABLE 1

$^1$H NMR δ (600 MHz, D$_2$O) and $^{13}$C NMR δ (150 MHz, D$_2$O) of pentasaccharide 1.[a]

| | α-Glc (A) | α-Glc (B) | β-Glc (C) | α-Rha (D) | α-Rha (D') | Linker |
|---|---|---|---|---|---|---|
| H-1 | 5.18 | 5.09 | 4.53 | 5.24 | 5.14 | |
| C-1 | 96.1 | 96.8 | 102.4 | 101.8 | 102.0 | |
| H-2 | 3.70 | 3.73 | 3.38 | 4.06 | 4.06 | |
| C-2 | 72.7 | 73.4 | 75.3 | 71.4 | 71.2 | |
| H-3 | 3.70 | 4.03 | 3.61 | 3.88 | 3.81 | |
| C-3 | 76.1 | 77.0 | 83.2 | 71.1 | 71.2 | |
| H-4 | 3.48 | 3.86 | 3.46 | 3.47 | 3.47 | |
| C-4 | 70.5 | 73.8 | 69.1 | 73.0 | 73.0 | |
| H-5 | 3.82 | 4.05 | 3.45 | 4.43 | 4.03 | |
| C-5 | 72.5 | 72.3 | 77.2 | 69.5 | 69.8 | |
| H-6 a/b | 3.88/3.78 | 3.92 | 3.80/3.96 | 1.27 | 1.27 | |
| C-6 | 61.6 | 60.3 | 62.2 | 17.5 | 17.5 | |
| H-1' a/b | | | | | | 3.79/3.59 |
| C-1' | | | | | | 68.7 |
| H-2' | | | | | | 1.70 |
| C-2' | | | | | | 29.0 |
| H-3' | | | | | | 1.49 |
| C-3' | | | | | | 23.5 |
| H-4' | | | | | | 1.70 |
| C-4' | | | | | | 27.7 |
| H-5' | | | | | | 3.01 |
| C-5' | | | | | | 40.4 |

[a]$^1$H and $^{13}$C NMR resonances were assigned based on HSQC, HMBC, COSY and TOCSY experiments.

TABLE 2

Comparison of $^1$H and $^{13}$C NMR δ between 1 and the native PS-I repeating unit.[a]

| | α-Glc (A) | α-Glc (B) | β-Glc (C) | α-Rha (D) | α-Rha (D') |
|---|---|---|---|---|---|
| H-1 | 5.18 | 5.09 | 4.53 | 5.24 | 5.14 |
| | *5.75* | *5.13* | *4.53* | *5.23* | *5.17* |
| C-1 | 96.1 | 96.8 | 102.4 | 101.8 | 102.0 |
| | *93.5* | *98.0* | *102.4* | *101.9* | *101.4* |
| H-2 | 3.70 | 3.73 | 3.38 | 4.06 | 4.06 |
| | *3.68* | *3.70* | *3.38* | *4.07* | *4.09* |
| C-2 | 72.7 | 73.4 | 75.3 | 71.4 | 71.2 |
| | *77.3* | *73.6* | *75.2* | *71.1* | *71.2* |
| H-3 | 3.70 | 4.03 | 3.61 | 3.88 | 3.81 |
| | *3.89* | *4.01* | *3.62* | *3.85* | *3.97* |
| C-3 | 76.1 | 77.0 | 83.2 | 71.1 | 71.2 |
| | *72.1* | *77.5* | *83.0* | *71.0* | *70.9* |
| H-4 | 3.48 | 3.86 | 3.46 | 3.47 | 3.47 |
| | *3.53* | *3.86* | *3.46* | *3.46* | *4.07* |
| C-4 | 70.5 | 73.8 | 69.1 | 73.0 | 73.0 |
| | *70.1* | *73.6* | *69.1* | *73.0* | *78.9* |
| H-5 | 3.82 | 4.05 | 3.45 | 4.43 | 4.03 |
| | *3.91* | *4.06* | *3.45* | *4.44* | *4.12* |
| C-5 | 72.5 | 72.3 | 77.2 | 69.5 | 69.8 |
| | *73.8* | *72.4* | *77.1* | *69.4* | *68.6* |
| H-6 a/b | 3.88/3.78 | 3.92 | 3.80/3.96 | 1.27 | 1.27 |
| | n.d. | n.d. | *3.80/3.95* | *1.27* | *1.33* |
| C-6 | 61.6 | 60.3 | 62.2 | 17.5 | 17.5 |
| | n.d. | n.d. | *62.2* | *17.5* | *17.8* |

[a]data of native PS-I reported in italic taken from: J. Ganeshapillai et al., *Carbohydr. Res.*, 2008, 343, 703.

Synthesis of Pentasaccharide 1 and Intermediates According to Schemes 6-8

(2-Methyl-5-tert-butylphenyl) 4,6-O-benzylidene-2-O-benzyl-3-O-(4-bromo)benzyl-1-thio-β-D-glucopyranoside (25)

To a solution of 12 (200 mg, 0.38 mmol) in anhydrous DMF (2 ml), NaH (22 mg, 0.92 mmol) was added followed by para-bromobenzyl (PBB) bromide (288 mg, 1.15 mmol) at 0° C. The mixture was warmed to room temperature over 2 h, cooled to 0° C. and quenched by the addition of MeOH. Et$_2$O was added and the organic layer washed with 0.1 M HCl solution and with saturated aqueous NaHCO$_3$ solution. The phases were separated and the organic layer was dried over MgSO$_4$ and concentrated. Column chromatography (cyclohexane/ethyl acetate) afforded 25 (276 mg) along with aromatic impurities and was taken to the next step without further purification.

(2-Methyl-5-tert-butylphenyl) 2,6-di-O-benzyl-3-O-(4-bromo)benzyl-1-thio-β-D-glucopyranoside (26)

To a solution of 25 (140 mg, 0.20 mmol) in anhydrous DCM (4 ml) freshly activated molecular sieves (4 Å) were added. The mixture was cooled to −78° C., TES (97 µl, 0.61 mmol) and TfOH (61 µl, 0.69 mmol) were added. After stirring for 3 hours at −78° C., the reaction was quenched by the addition of saturated aqueous NaHCO$_3$ solution, diluted with DCM and washed with a saturated aqueous NaHCO$_3$ solution. The organic phase was then dried over MgSO$_4$, filtered and concentrated. Column chromatography on silica gel (cyclohexane/ethyl acetate) afforded 26 (81 mg, 0.12 mmol, 58%). $^1$H-NMR (400 MHz, CDCl$_3$) δ 7.65-7.60 (m, 1H, ArH), 7.54-7.10 (m, 16H, ArH), 4.98 (d, 1H, J=10.3 Hz, benzyl), 3.65-3.44 (m, 6H, benzyl, 1-H), 3.79-3.70 (m, 3H, 6-H, 4-H), 3.56-3.43 (m, 3H, 2-H, 3-H, 5-H), 2.76 (d, 1H, J=2.2 Hz, 4-OH), 2.40 (s, 3H, CH$_3$), 1.26 (s, 9H, tBu); $^{13}$C-NMR (100 MHz, CDCl$_3$) δ 149.7, 138.1, 137.72, 137.67, 136.1, 133.3, 131.7, 130.0, 129.6, 128.9, 128.6, 128.5, 128.3, 128.0, 128.0, 124.7, 121.8, 88.2 (C-1), 86.2 (C-2), 80.7 (C-3), 77.5 (C-5), 75.7, 74.7, 73.9, 72.7 (C-4), 70.7 (C-6), 31.4, 20.5; HRMS (ESI): Calcd for $C_{38}H_{43}BrO_5SNa^+$ [M+Na]$^+$ 713.1907. found 713.1951.

(2-Methyl-5-tert-butylphenyl) 2,6-di-O-benzyl-3-O-(4-bromo)benzyl-4-O-levulinoyl-1-thio-β-D-glucopyranoside (27)

To a solution of 26 (1.55 g, 2.24 mmol) in DCM (20 ml) at 0° C., DMAP (274 mg, 2.24 mmol), LevOH (1.30 ml, 11.20 mmol) and DCC (2.31 g, 11.20 mmol) were added. The solution was warmed to room temperature and stirred for 16 h. The reaction was diluted with DCM and the organic layers were washed with a 0.1 M HCl solution and saturated aqueous NaHCO$_3$ solution. The organic layer was dried over MgSO$_4$ and concentrated. Column chromatography on silica gel (hexanes/ethyl acetate) afforded 27 (1.54 g, 1.95 mmol, 87%). $[α]_D^{20}$=+6.4° (c=3.4, CHCl$_3$), IR $ν_{max}$ (film) 2963, 1744, 1718, 1488, 1361, 1261, 1068, 1038, 1012 cm$^{-1}$; $^1$H-NMR (400 MHz, CDCl$_3$) δ 7.70-7.05 (m, 17H, Ar—H), 5.11-5.04 (m, 1H, 4-H), 4.97 (app. d, 1H, J=10.4 Hz, benzyl-H), 4.77-4.60 (m, 4H, benzyl-H, 1-H), 4.48 (s, 1H, PBB-H), 3.70-3.54 (m, 5H, 2-H, 3-H, 5-H, 6-H), 2.64-2.55 (m, 2H, Lev-CH$_2$), 2.40 (s, 3H, S—CH$_3$), 2.35-2.29 (m, 2H, Lev-CH$_2$), 2.12 (s, 3H, Lev-CH$_3$), 1.25 (s, 9H, tBu); $^{13}$C-NMR (100 MHz, CDCl$_3$) δ 206.2 (Lev-carbonyl), 171.7, 149.8, 138.1, 138.0, 137.5, 136.2, 133.2, 131.6, 130.0, 129.6, 128.9, 128.5, 128.4, 128.3, 128.1, 128.0, 127.69, 124.71, 121.6, 88.3 (C-1), 84.1, 81.1, 77.4, 75.8, 74.5, 73.7, 71.3, 69.7, 37.8, 34.6, 31.4, 29.9, 28.0, 20.5; HRMS (MALDI-TOF): Calcd for $C_{43}H_{49}BrO_7SNa^+$ $[M+Na]^+$ 811.2275. found 811.2026.

(2-Methyl-5-tert-butylphenyl) 2-O-benzoyl-4-O-benzyl-3-O-tert-butyldimethylsilyl-1-thio-β-D-glucopyranoside (28)

To a solution of 15 (800 mg, 1.23 mmol) in anhydrous DCM (12 ml) freshly $BH_3$·THF (1 M in THF, 7.4 ml, 7.4 mmol) and TMSOTf (0.11 ml, 0.62 mmol) were added drop wise at 0° C. The reaction was warmed to room temperature over 2 hours, cooled to 0° C. again and quenched by the drop wise addition of saturated aqueous $NaHCO_3$ solution. The Emulsion was diluted with DCM and washed with a saturated aqueous NaHCO3 solution. The organic phase was then dried over MgSO4, filtered and concentrated. Crude 28 was taken to the next step.

(2-Methyl-5-tert-butylphenyl) 2-O-benzoyl-4,6-di-O-benzyl-3-O-tert-butyldimethylsilyl-1-thio-β-D-glucopyranoside (29)

To a solution of crude 28 (approx. 1.23 mmol) in THF/DMF (9:1, 10 ml) at 0° C., BnBr (0.18 ml, 1.50 mmol) and NaH (36 mg, 1.50 mmol) were added. The solution was warmed to room temperature over 2 h, then cooled to 0° C. again and further BnBr (0.18 ml, 1.50 mmol) was added. The reaction was warmed to room temperature over 30 min, cooled to 0° C. and quenched by the addition of water. After dilution with $Et_2O$ the phases were separated and the aqueous layer extracted with $Et_2O$. The organic phase was then dried over MgSO4, filtered and concentrated. Column chromatography on silica gel (hexanes/ethyl acetate) afforded 29 (797 mg, 1.08 mmol, 88%). $^1$H-NMR (400 MHz, $CDCl_3$) δ 8.14-7.00 (m, 18H, Ar—H), 5.31 (dd, 1H, $J_1$=10.1 Hz, $J_2$=8.9 Hz, 2-H), 4.83 (app. d, 1H, J=11.3 Hz, benzyl-Ha), 4.72 (d, 1H, J=10.2 Hz, 1-H), 4.63 (app. d, 1H, J=11.0 Hz, benzyl-$H_b$), 4.58 (app. d, 2H, J=3.1 Hz, benzyl-H), 3.95 (app. t, 1H, J=8.7 Hz, 3-H), 3.78-3.51 (m, 4H, 4-H, 5-H, 6-H), 2.15 (s, 3H, S—$CH_3$), 1.25 (s, 9H, S-tBu), 0.79 (s, 9H, TBS-tBu), 0.00 (s, 3H, TBS-$CH_3$), −0.16 (s, 3H, TBS-$CH_3$); $^{13}$C-NMR (100 MHz, $CDCl_3$) δ 165.6, 149.7, 138.2, 136.5, 133.2, 130.5, 130.1, 129.8, 129.2, 128.5, 128.4, 128.0, 127.72, 128.0, 127.6, 124.7, 88.0 (C-1), 79.5 (C-5), 78.9 (C-4), 77.0 (C-3), 75.1, 73.6 (C-2), 73.5, 69.0 (C-6), 31.4, 25.8, 20.3, −3.9, −4.1; HRMS (ESI): Calcd for $C_{44}H_{56}O_6SSiNa^+$ $[M+Na]^+$ 763.3459. found: 763.3500

N-(Benzyl)benzyloxycarbonyl-5-amino-pentanyl 2,6-di-O-benzyl-3-O-(4-bromo)benzyl-α-D-glucopyranosyl-(1→2)-3,4,6-Tri-O-benzyl-α-D-glucopyranoside (30)

Thioglucoside 27 (323 mg, 0.41 mmol) and glucoside 2 (222 mg, 0.29 mmol) were coevaporated with toluene three times and dried in vacuo. The mixture was dissolved in Ether (4 ml), freshly activated and acid washed molecular sieves (4 Å) and NIS (105 mg, 0.47 mmol) were added and cooled to −40° C. TfOH (4.2 µl, 0.05 mmol) was added and the mixture was stirred and warmed up to −10° C. in one hour. The reaction was quenched by the addition of pyridine, diluted with DCM and washed with aqueous $Na_2S_2O_3$ and saturated aqueous $NaHCO_3$ solutions. The phases were separated and the aqueous phase was extracted with DCM. The combined organic phases were dried over MgSO4, filtered and concentrated. The crude product was purified by column chromatography on silica gel (toluene/acetone) to afford 30 (276 mg, 0.20 mmol, 69%). $[\alpha]_D^{20}$=+54.1° (c=4.8, $CHCl_3$), IR $v_{max}$ (film) 3031, 2923, 2864, 1744, 1698, 1497, 1454, 1420, 1360, 1209 cm$^{-1}$; $^1$H-NMR (400 MHz, $CDCl_3$) δ 7.60-7.02 (m, 39H, Ar—H), 5.24-5.10 (m, 3-H), 5.09-4.93 (m, 3H, 2× anomeric-H), 4.89-4.37 (m, 13H), 4.13-4.00 (m, 2H), 3.99-3.56 (m, 8H), 3.50-3.08 (m, 5H), 2.63-2.47 (m, 2H), 2.25-2.18 (m, 2H), 2.13 (s, 3H, Lev-$CH_3$), 1.71-1.38 (m, 4H, linker-H), 1.36-1.14 (m, 2H, linker-H); $^{13}$C-NMR (100 MHz, $CDCl_3$) δ 206.3 (Lev-carbonyl), 171.4, 138.7, 138.3, 138.1, 138.1, 137.8, 131.4, 129.6, 128.7, 128.5, 128.4, 128.3, 128.1, 128.03, 127.98, 127.93, 127.88, 127.8, 127.60, 127.57, 127.4, 121.4, 95.5 (C-anomeric), 93.5 (C-anomeric), 80.9, 79.3, 78.8, 78.1, 75.7, 75.3, 74.1, 73.7, 73.5, 72.3, 70.5, 70.2, 68.6, 68.3, 68.1, 67.3, 37.8, 30.0, 29.5, 27.9, 23.7; HRMS (MALDI-TOF): Calcd for $C_{79}H_{86}BrNO_{15}Na^+$ $[M+Na]^+$ 1390.5073. found 1390.5105.

N-(Benzyl)benzyloxycarbonyl-5-amino-pentanyl 2,6-di-O-benzyl-3-O-(4-bromo)benzyl-α-D-glucopyranosyl-(1→2)-3,4,6-Tri-O-benzyl-α-D-glucopyranoside (31)

To a solution of 30 (300 mg, 0.22 mmol) in DCM (5.0 ml) hydrazine hydrate (32 µl, 0.66 mmol) dissolved in AcOH (0.4 ml) and pyridine (0.6 ml) was added and the solution stirred for 1 h. The reaction was then quenched by the addition of acetone and concentrated. Column chromatography on silica gel (hexanes/ethyl acetate) afforded 31 (117 mg, 0.09 mmol, 96%). $[\alpha]_D^{20}$=+56.5° (c=2.7, $CHCl_3$), IR $v_{max}$ (film) 3453, 2963, 1695, 1454, 1420, 1360, 1259, 1013 cm$^{-1}$; H-NMR (600 MHz, $CDCl_3$) δ 7.90-7.00 (39H, m, Ar—H), 5.25-5.13 (m, 2H), 5.10 (bs, 1H, anomeric-H), 5.05 (bs, 1H, anomeric-H), 4.98-4.43 (m, 14H), 4.10-3.53 (m, 13H), 3.45-3.10 (m, 3H), 1.65-1.40 (m, 4H, linker-H), 1.34-1.15 (m, 2H, linker-H); $^{13}$C-NMR (150 MHz, $CDCl_3$) δ 138.7, 138.2, 138.1, 131.6, 129.7, 128.6, 128.49, 128.45, 128.1, 128.0, 127.97, 127.91, 127.85, 127.74, 127.71, 127.3, 121.6, 95.6 (C-anomeric), 93.9 (C-anomeric), 81.4, 81.0, 78.9, 78.1, 77.4, 77.2, 77.0, 75.8, 75.2, 74.4, 73.6, 73.6, 72.1, 71.1, 70.5, 69.3, 68.6, 68.3, 67.3, 50.3, 47.2, 46.2, 43.3, 29.5, 27.7, 23.6; HRMS (MALDI-TOF): Calcd for $C_{74}H_{80}BrNO_{13}Na^+$ $[M+Na]^+$ 1292.4705. found 1292.4701.

N-(Benzyl)benzyloxycarbonyl-5-amino-pentanyl 2-O-benzoyl-4,6-di-O-benzyl-3-O-tert-butyldimethylsilyl-α-D-glucopyranosyl-(1→4)-2,6-di-O-benzyl-3-O-(4-bromo)benzyl-α-D-glucopyranosyl-(1→2)-3,4,6-tri-O-benzyl-α-D-glucopyranoside (32)

Thioglucoside 29 (233 mg, 0.31 mmol) and disaccharide 31 (266 mg, 0.21 mmol) were coevaporated with toluene three times and dried in vacuo. The mixture was dissolved in DCM (7 ml), freshly activated and acid washed molecular sieves (4 Å) and NIS (80 mg, 0.36 mmol) were added and cooled to −30° C. TfOH (3.2 µl, 0.04 mmol) was added and the mixture was stirred and warmed up to −17° C. in one hour. The reaction was quenched by the addition of pyridine, diluted with DCM and washed with aqueous $Na_2S_2O_3$ and saturated aqueous $NaHCO_3$ solutions. The phases were separated and the aqueous phase was extracted with DCM. The combined organic phases were dried over MgSO4, filtered and concentrated. The crude product was purified by column chromatography on silica gel (toluene/acetone) to afford 32 (354 mg, 0.19 mmol, 92%). $[\alpha]_D^{20}$=+52.5° (c=2.6, $CHCl_3$), IR $v_{max}$ (film) 3031, 2928, 2859, 1733, 1699, 1603, 1497, 1454, 1421, 1362, 1314, 1265, 1070 cm$^{-1}$; $^1$H-NMR (400 MHz, CDCl$_3$) δ 7.91-7.05 (m, 54H, Ar—H), 5.21-5.11 (m, 3H), 5.04 (bs, 1H, anomeric-H), 5.01-4.95 (m, 2H, anomeric-H), 4.81 (app. d, 1H, J=11.3 Hz), 4.74-4.35 (m, 17H, anomeric-H), 4.23 (app. d, 1H, J=12.3 Hz), 3.98 (app. t, 1H, J=9.4 Hz), 3.93-3.87 (m, 1H), 3.82 (app. t, 1H, J=9.3 Hz), 3.74-3.66 (m, 4H), 3.64-3.45 (m, 10H), 3.42-3.36 (m, 1H), 3.34-3.06 (m, 4H), 1.56-1.35 (m, 4H), 1.25-1.09 (m, 2H), 0.79 (s, 9H, tBu), 0.02 (s, 3H), −0.19 (s, 3H); $^{13}$C-NMR (100 MHz, CDCl$_3$) δ 164.8, 138.7, 138.7, 138.4, 138.4, 138.4, 138.1, 133.1, 131.1, 130.1, 130.0, 129.6, 128.7, 128.6, 128.49, 128.48, 128.43, 128.41, 128.40, 128.37, 128.35, 128.2, 128.0, 127.93, 127.86, 127.8, 127.7, 127.64, 127.58, 127.5, 127.4, 120.8, 100.3 (C-anomeric), 96.1 (C-anomeric), 59.0 (C-anomeric) 80.5, 80.0, 79.1, 78.6, 77.7, 76.1, 75.5, 75.4, 75.3, 75.2, 74.7, 74.4, 73.8, 73.6, 73.5, 72.3, 70.6, 70.3, 69.1, 68.7, 67.6, 67.2, 50.6, 47.2, 46.3, 29.4, 28.1, 25.8, 23.6, 17.9, −3.86, −3.89; HRMS (MALDI-TOF): Calcd for C$_{107}$H$_{120}$BrNO$_{19}$SiNa$^+$ [M+Na]$^+$ 1852.7299 found 1852.7375.

N-(Benzyl)benzyloxycarbonyl-5-amino-pentanyl 2-O-benzoyl-4,6-di-O-benzyl-β-D-glucopyranosyl-(1→4)-2,6-di-O-benzyl-α-D-glucopyranosyl-(12)-3,4,6-tri-O-benzyl-α-D-glucopyranoside (33)

A solution of 32 (100 mg, 0.06 mmol), (3,4-dimethoxyphenyl)boronic acid (20 mg, 0.11 mmol), TBABr (1.8 mg, 5.5 μmol), K$_3$PO$_4$ (35 mg, 0.16 mmol) in EtOH (4 ml) was subjected to three freeze-pump-saw cycles. To this solution Pd(OAc)$_2$ (1.2 mg, 5.5 μmol) was added and stirred for 2 hours. The mixture was diluted with EtOAc and washed with saturated aqueous NaHCO$_3$ solution. The aqueous phase was back extracted with EtOAc. The combined organic phases were dried over MgSO$_4$, filtered and concentrated. The crude product was purified by column chromatography on silica gel (toluene/acetone) to afford the Suzuki coupling product (95 mg, 0.05 mmol, 92%) which was dissolved in DCM/H$_2$O/saturated aqueous NaHCO$_3$ (100:9:1, 11 ml). To this emulsion DDQ (34 mg, 0.15 mmol) was added, stirred vigorously for 16 hours, diluted with DCM and washed with saturated aqueous NaHCO$_3$ solutions. The combined organic phases were dried over MgSO$_4$, filtered and concentrated. The crude product was dissolved in DMF (2.5 ml), and treated with a solution of TBAF.3H$_2$O (137 mg, 0.43 mmol) and AcOH (29 μl, 0.51 mmol) in DMF (2.5 ml) at 50° C. for three days. After dilution with Et$_2$O the phases were separated and the organic phase washed with a 0.1 M HCl solution, saturated aqueous NaHCO$_3$ solution and brine. The organic phase was then dried over MgSO4, filtered and concentrated. The crude product was purified by column chromatography on silica gel (toluene/acetone) to afford 33 (52 mg, 0.03 mmol, 68%). [c]D$^{20}$=+38.9° (c=1.5, CHCl$_3$), IR $v_{max}$ (film) 3462, 3031, 2924, 2867, 1729, 1699, 1497, 1454, 1422, 1362, 1315, 1268, 1095, 1069 cm$^{-1}$; H-NMR (400 MHz, CDCl$_3$) δ 8.07-7.00 (m, 50H), 5.25-5.05 (m, 3H), 5.03-4.94 (m, 2H, 2× anomeric-H), 4.90 (app. d, J=10.6, 1H), 4.82-4.35 (m, 16H), 4.27 (app. d, J=12.1, 1H), 4.16 (app. dd, J=9.2, 8.8, 1H), 4.06 (app. d, J=12.2, 1H), 3.99 (app. t, J=9.3, 1H), 3.93-3.42 (m, 15H), 3.28 (s, 4H), 1.73-1.36 (m, 4H, linker-H), 1.34-1.08 (m, 2H, linker-H); $^{13}$C-NMR (100 MHz, CDCl$_3$) δ 166.2, 139.0, 138.5, 138.4, 137.9, 137.7, 133.6, 130.1, 129.4, 128.72, 128.65, 128.62, 128.59, 128.57, 128.52, 128.46, 128.45, 128.40, 128.36, 128.30, 128.24, 128.18, 127.97, 127.95, 127.93, 127.88, 127.8, 127.61, 127.57, 127.37, 101.2 (C-anomeric), 95.9 (C-anomeric), 94.8 (C-anomeric), 81.6, 78.4, 78.2, 78.0, 77.5, 77.4, 77.2, 76.8, 76.6, 76.3, 75.0, 74.7, 73.9, 73.6, 73.2, 72.7, 72.2, 70.4, 69.3, 69.1, 68.7, 67.3, 50.4, 47.3, 29.5, 28.1, 23.6; HRMS (MALDI-TOF): Calcd for C$_{94}$H$_{101}$NO$_{19}$Na$^+$ [M+Na]$^+$ 1570.6860. found 1570.6362.

N-(Benzyl)benzyloxycarbonyl-5-amino-pentanyl 2,3-di-O-benzoyl-4-O-benzyl-α-L-rhamnopyranosyl-(1→3)-2-O-benzoyl-4,6-O-benzyl-β-D-glucopyranosyl-(1→4)-[2,3-di-O-benzoyl-4-O-benzyl-α-L-rhamnopyranosyl-(1→3)]-2,6-di-O-benzyl-α-D-glucopyranosyl-(1→2)-3,4,6-tri-O-benzyl-α-D-glucopyranoside (34)

Rhamnosyl-imidate 5 (72 mg, 140 μmol) and trisaccharide 33 (42 mg, 27 μmol) were coevaporated with toluene three times, dried in vacuo and dissolved in anhydrous DCM (3.0 ml). Freshly activated molecular sieves (4 Å) were added and the mixture cooled to −40° C. TMSOTf (25 μl of a solution of 100 μl TMSOTf in 900 μl DCM, 14 μmol) was added and the reaction was warmed to −20° C. over 1.5 h. The reaction was quenched with TEA and concentrated. Size exclusion chromatography on Sephadex LH-20 (CHCl$_3$/MeOH 1:1) afforded 34 (58 mg, 24 μmol, 88%). [α]$_D^{20}$=+49.7° (c=2.2, CHCl$_3$), IR $v_{max}$ (film) 3031, 2927, 2863, 1729, 1700, 1602, 1497, 1453, 1273, 1264, 1095, 1069 cm$^{-1}$; $^1$H-NMR (600 MHz, CDCl$_3$) δ 8.08-6.98 (m, 80, Ar—H), 5.89 (app. dd, J=9.4, 3.5, 1H), 5.85 (app. dd, J=3.5, 1.7, 1H), 5.66 (app. dd, J=9.4, 3.5, 1H), 5.49-5.42 (m, 1H), 5.39 (app. dd, J=3.5, 1.8, 1H), 5.32-5.25 (m, 1H), 5.16-5.12 (m, 2H), 5.085.05 (m, 1H), 5.04-4.99 (m, 1H), 4.97 (d, J=1.6, 1H), 4.954.25 (m, 20H), 4.24-3.43 (m, 20H), 3.39-3.00 (m, 5H), 1.67 (d, J=6.2, 3H), 1.60-1.32 (m, 4H), 1.32-1.06 (m, 2H), 0.94 (d, J=6.1, 3H); $^{13}$C-NMR (150 MHz, CDCl$_3$) δ 165.43, 165.21, 164.49, 164.12, 139.19, 138.54, 138.37, 138.16, 137.83, 137.74, 133.13, 133.01, 132.95, 132.69, 132.68, 130.38, 130.14, 130.11, 129.99, 129.94, 129.89, 129.78, 129.75, 129.74, 129.45, 128.95, 128.70, 128.67, 128.65, 128.62, 128.55, 128.47, 128.45, 128.41, 128.39, 128.36, 128.26, 128.23, 128.19, 128.15, 128.02, 127.95, 127.93, 127.91, 127.75, 127.66, 127.36, 127.22, 99.53, 97.97, 97.73, 95.81, 93.74, 80.83, 80.40, 80.26, 79.27, 78.40, 78.25, 77.52, 76.58, 76.15, 75.91, 75.74, 75.16, 74.68, 74.20, 74.01, 73.68, 73.58, 73.27, 72.87, 72.19, 71.93, 71.20, 71.16, 70.59, 70.33, 68.69, 68.09, 67.99, 67.33, 67.22, 50.61, 47.18, 46.26, 29.44, 23.56, 18.58, 17.75; HRMS (MALDI-TOF): Calcd for C$_{148}$H$_{149}$NO$_{31}$Na$^+$ [M+Na]$^+$ 2459.0006. found 2459.0636.

5-Amino-pentanyl α-L-rhamnopyranosyl-(1→3)-β-D-glucopyranosyl-(1→4)-[α-L-rhamnopyranosyl-(1→3)]-α-D-glucopyranosyl-(1→2)-α-D-glucopyranoside (1)

To a solution of fully protected pentasaccharide 34 (23 mg, 9.4 μmol) in THF (1.5 ml) NaOMe (0.5 M, in MeOH, 1 ml) was added and stirred for 12 h. The mixture was neutralized with Amberlite IR 120 (H$^+$) ion exchange resin, filtered and concentrated. Column chromatography on silica gel (DCM/acetone/MeOH) afforded the de-benzoylated pentasaccharide (16 mg), which was dissolved in a mixture of THF (1 ml) MeOH (1 ml), H$_2$O (0.7 ml) and AcOH (0.1 ml). The solution was purged with Ar, 10% Pd/C (30 mg) was added and the solution purged with H$_2$ for 30 min, then stirred under an H$_2$ atmosphere for 12 h, filtered and concentrated. Size exclusion chromatography on Sephadex LH-20 (MeOH) afforded 1 (5.0 mg, 5.7 μmol, 60%). NMR data is consistent with previously reported.[3]

EXAMPLE 2

Preparation of PS-I Substructures

5-Amino-pentanyl D-glucopyranosyl-(1→2)-α-D-glucopyranoside (35)

A solution of protected disaccharide 33 (40 mg, 31 µmol) in a mixture of MeOH (5.0 ml), THF (2.5 ml) $H_2O$ (2.0 ml) and AcOH (0.5 ml) was purged with Ar. After that 10% Pd/C (70 mg) was added and the solution purged with $H_2$ for 30 min, then stirred under an $H_2$ atmosphere for 12 h, filtered and concentrated. The crude product was purified by reversed phase solid phase extraction (RP SPE) (Waters Sep-Pak®, C18) to afford 35 (13.3 mg, 31 µmol, 99%). $^1$H-NMR (600 MHz, $D_2O$) δ 5.23 (d, J=3.4, 1H, anomeric), 5.16 (d, J=3.6, 1H, anomeric), 4.02-3.80 (m, 8H), 3.75 (app. dd, J=9.9, 3.5, 2H) 3.68-3.61 (m, 2H), 3.53 (app. td, J=9.6, 4.7, 2H), 3.09 (app. t, J=7.5, 2H), 1.81-1.71 (m, 4H, linker), 1.59-1.49 (m, 2H, linker); $^{13}$C-NMR (150 MHz, $D_2O$) δ 98.6 (anomeric), 97.9 (anomeric), 77.7, 75.4, 74.5, 74.4, 74.2, 74.0, 72.3, 72.1, 70.4, 63.3, 63.1, 42.1, 30.6, 29.2, 25.1; HRMS (MALDI-TOF): Calcd for $C_{17}H_{33}NO_{11}H^+$ [M+H]$^+$ 428.2126. found 428.2147.

5-Amino-pentanyl β-D-glucopyranosyl-(1→4)-α-D-glucopyranosyl-(1→2)-α-D-glucopyranoside (36)

To a solution of protected trisaccharide 33 (60 mg, 31 µmol) in THF (2 ml) NaOMe (0.5 M in MeOH, 0.5 ml) was added and stirred for 4 h. The mixture was neutralized with Amberlite IR 120 (H+) ion exchange resin, filtered and concentrated. The crude product was dissolved in a mixture of THF (5.0 ml) MeOH (2.5 ml), $H_2O$ (2.0 ml) and AcOH (0.5 ml). The solution was purged with Ar, then 10% Pd/C (30 mg) was added and the solution purged with $H_2$ for 30 min, then stirred under an $H_2$ atmosphere for 12 h, filtered and concentrated. Purification by RP SPE (Waters Sep-Pak®, C18) afforded 36 (13.3 mg, 31 µmol, 66%). $^1$H-NMR (600 MHz, $D_2O$) δ 5.22 (d, J=3.3, 1H, anomeric α-Glc), 5.15 (d, J=3.6, 1H, anomeric α-Glc), 4.60 (d, J=7.9, 1H, anomeric β-Glc), 4.14-4.08 (m, 1H), 4.03-3.91 (m, 5H), 3.90-3.79 (m, 4H), 3.78-3.72 (m, 3H), 3.71-3.62 (m, 2H), 3.62-3.47 (m, 4H), 3.40 (t, J=8.7, 1H), 3.09 (t, J=7.5, 2H), 1.83-1.72 (m, 4H, linker), 1.59-1.49 (m, 2H, linker). $^{13}$C-NMR (150 MHz, $D_2O$) δ 100.7 (anomeric 3-Glc), 94.0 (anomeric α-Glc), 93.4 (anomeric α-Glc), 76.8, 74.2, 73.7, 73.5, 71.3, 69.8, 69.6, 69.5, 69.2, 68.7, 67.7, 67.6, 65.9, 58.8, 57.9, 37.5, 26.1, 24.6, 20.6; HRMS (MALDI-TOF): Calcd for $C_{23}H_{43}NO_{16}Na^+$ [M+Na]$^+$ 612.2474. found 612.2424.

(2-Methyl-5-tert-butylphenyl) 2-O-benzoyl-4,6-di-O-benzyl-1-thio-β-D-glucopyranoside (40)

A solution of TBAF.3$H_2O$ (1.10 g, 3.48 mmol) and acetic acid (266 µl, 4.64 mmol) in DMF (4 ml) was added to a solution of 29 (430 mg, 0.58 mmol) in DMF (4 ml). The mixture was stirred for 3 days at 35° C. After dilution with $Et_2O$ the phases were separated and the organic phase washed with a 0.1 M HCl solution, saturated aqueous $NaHCO_3$ solution and brine. The organic phase was then dried over MgSO4, filtered and concentrated. The product 40 was taken directly to the next step.

(2-Methyl-5-tert-butylphenyl) 2,3-di-O-benzoyl-4-O-benzyl-α-L-rhamnopyranosyl-(1→3)2-O-benzoyl-4,6-di-O-benzyl-1-thio-β-D-glucopyranoside (41)

Rhamnosyl-imidate 5 (373 mg, 0.59 mmol) and glucoside 40 (approx. 0.58 mmol) were coevaporated with toluene three times, dried in vacuo and dissolved in anhydrous DCM (3.0 ml). Freshly activated molecular sieves (4 Å) were added and the mixture cooled to −40° C. TMSOTf (10 µl, 53 µmol) was added and the reaction was warmed to −20° C. over 1.5 h. The reaction was quenched with TEA and concentrated. Column chromatography on silica gel (hexanes/ethyl acetate) afforded 41 (490 mg, 0.46 mmol, 79%). $[\alpha]_D^{20}$=+70.7° (c=1.9, CHCl$_3$), IR $\nu_{max}$ (film) 2963, 1728, 1602, 1451, 1259, 1090, 1067, 1025 cm$^{-1}$; $^1$H-NMR (400 MHz, CDCl$_3$) δ 8.02-7.03 (m, 33H), 5.72 (dd, J=9.4, 3.5, 1H), 5.53-5.42 (m, 2H), 5.22 (d, J=1.9, 1H), 4.88 (d, J=10.6, 1H), 4.77-4.47 (m, 6H), 4.24-4.13 (m, 2H), 3.92-3.80 (m, 3H), 3.68-3.59 (m, 2H), 2.18 (s, 3H), 1.25 (s, 9H), 1.08 (d, J=6.2, 3H). $^{13}$C-NMR (100 MHz, CDCl$_3$) δ 149.8, 138.1, 138.0, 133.1, 130.3, 130.0, 129.9, 129.8, 129.7, 129.7, 128.64, 128.57, 128.51, 128.46, 128.42, 128.39, 128.37, 128.32, 128.28, 128.24, 128.20, 128.1, 128.00, 127.97, 127.9, 127.83, 127.80, 127.75, 125.7, 124.4, 97.6, 86.6, 79.3, 77.5, 77.2, 76.8, 75.7, 75.6, 75.0, 74.4, 73.8, 72.0, 71.3, 68.3, 67.9, 31.5, 19.5, 18.0; HRMS (MALDI-TOF): Calcd for $C_{65}H_{66}O_{12}SNa^+$ [M+Na]$^+$ 1093.4167. found 1093.4159.

N-(Benzyl)benzyloxycarbonyl-5-amino-pentanyl 2,3-di-O-benzoyl-4-O-benzyl-α-L-rhamnopyranosyl-(1→3)2-O-benzoyl-4,6-di-O-benzyl-1-thio-β-D-glucopyranoside (42)

Disaccharide 41 (50 mg, 47 µmol) and 5-aminopentanol (31 mg, 93 µmol) were coevaporated with toluene three times and dried in vacuo. The mixture was dissolved in DCM (3 ml) and NIS (13 mg, 56 µmol) was added and cooled to −20° C. TfOH (0.5 µl, 6 µmol) was added and the mixture was stirred and warmed up to 0° C. in two hours. The reaction was quenched by the addition of aqueous $Na_2S_2O_3$ and saturated aqueous $NaHCO_3$. The phases were separated and the aqueous phase was extracted with DCM. The combined organic phases were dried over MgSO$_4$, filtered and concentrated. The crude product was purified by column chromatography on silica gel (hexanes/ethyl acetates) to afford 42 (52 mg, 43 µmol, 91%). $[\alpha]_D^{20}$=+50.3° (c=2.6, CHCl$_3$), IR $\nu_{max}$ (film) 3032, 2936, 1730, 1698, 1452, 1265, 1069 cm$^{-1}$; $^1$H-NMR (400 MHz, CDCl$_3$) δ 8.23-6.80 (m, 40H, aromatic), 5.73 (dd, J=9.4, 3.5, 1H), 5.46 (dd, J=3.4, 1.9, 1H), 5.35 (dd, J=9.2, 7.9, 1H), 5.24 (d, J=1.9, 1H, anomeric Rha), 5.14 (bs, 2H), 4.89 (app. d, J=10.6, 1H), 4.72-4.59 (m, 4H), 4.56-4.35 (m, 4H, anomeric Glc), 4.22-4.12 (m, 2H), 3.91-3.76 (m, 4H), 3.68-3.58 (m, 2H), 3.42-3.33 (m, 1H), 3.05-2.88 (m, 2H), 1.50-1.29 (m, 4H, linker), 1.24-0.98 (m, 5H, linker, Rha CH$_3$). $^{13}$C-NMR (100 MHz, CDCl$_3$) δ 165.7, 164.8, 138.2, 138.0, 137.6, 133.1, 132.8, 30.0, 129.92, 129.88, 129.8, 129.7, 128.6, 128.5, 128.42, 128.38, 128.36, 128.31, 128.30, 128.2, 128.0, 127.94, 127.93, 127.8, 127.7, 101.1 (anomeric Glc), 97.6 (anomeric Rha), 79.3, 77.8, 76.9, 75.64, 75.59, 74.9, 74.6, 73.8, 71.9, 71.3, 68.9, 68.3, 67.2, 29.2, 23.2, 18.0 (Rha CH$_3$); HRMS (MALDI-TOF): Calcd for $C_{74}H_{75}NO_{15}Na^+$ [M+Na]$^+$ 1240.5029. found 1240.4792.

5-Amino-pentanyl α-L-rhamnopyranosyl-(1→3)-β-D-glucopyranoside (38)

To a solution of protected disaccharide 42 (50 mg, 41 µmol) in THF (2 ml) NaOMe (0.5 M in MeOH, 0.5 ml) was added and stirred for 4 h. The mixture was neutralized with Amberlite IR 120 (H+) ion exchange resin, filtered and concentrated. The crude product was dissolved in a mixture of THF (5.0 ml) MeOH (2.5 ml), $H_2O$ (2.0 ml) and AcOH (0.5 ml). The solution was purged with Ar, then 10% Pd/C (100 mg) was added and the solution purged with H$_2$ for 30 min, then stirred under an H$_2$ atmosphere for 12 h, filtered and concentrated. Purification by RP SPE (Waters Sep-Pak®, C18) afforded 38 (15.7 mg, 27 μmol, 78%). $^1$H-NMR (600 MHz, D$_2$O) δ 5.20 (s, 1H, anomeric Rha), 4.53 (d, J=8.1, 1H, anomeric Glc), 4.15-4.04 (m, 2H), 4.02-3.96 (m, 2H), 3.85 (app. dd, J=9.7, 3.3, 1H), 3.81-3.73 (m, 2H), 3.66 (app. t, J=8.7, 1H), 3.56-3.49 (m, 3H), 3.44 (t, J=8.7, 1H), 3.08 (app. t, J=7.5, 2H), 1.75 (tt, J=14.6, 7.2, 4H, linker), 1.57-1.49 (m, 2H, linker), 1.32 (d, J=6.3, 3H, Rha CH$_3$); $^{13}$C-NMR (150 MHz, D$_2$O) δ 100.0 (anomeric Glc), 99.1 (anomeric Rha), 80.3, 73.9, 71.8, 70.0, 68.4, 68.2, 68.1, 66.9, 66.2, 58.8, 37.4, 26.2, 24.4, 20.1, 14.5 (Rha CH$_3$); HRMS (MALDI-TOF): Calcd for C$_{17}$H$_{33}$NO$_{10}$Na$^+$ [M+Na]$^+$ 434.1997. found 434.1975.

N-(Benzyl)benzyloxycarbonyl-5-amino-pentanyl 2,6-di-O-benzyl-3-O-(4-bromo)benzyl-4-O-levulinoyl-1-thio-β-D-glucopyranoside (43)

Thioglucoside 27 (300 mg, 0.38 mmol) and 5-aminopentanol (200 mg, 0.61 mmol) were coevaporated with toluene three times and dried in vacuo. The mixture was dissolved in Ether (4 ml) and Dioxane (4 ml), NIS (103 mg, 0.46 mmol) was added and cooled to −10° C. TfOH (4 μl, 46 μmol) was added and the mixture was stirred and warmed up to 0° C. in three hours. The reaction was quenched by the addition of aqueous Na$_2$S$_2$O$_3$ and saturated aqueous NaHCO$_3$. The phases were separated and the aqueous phase was extracted with DCM. The combined organic phases were dried over MgSO$_4$, filtered and concentrated. The crude product was purified by column chromatography on silica gel (hexanes/ethyl acetates) to afford 43 (140 mg, 0.15 mmol, 39%). [α]$_D^{20}$=+22.0° (c=3.4, CHCl$_3$), IR ν$_{max}$ (film) 2920, 1743, 1697, 1454, 1420, 1360, 1208, 1153, 1069, 1038 cm$^{-1}$; $^1$H-NMR (400 MHz, CDCl$_3$) δ 7.696.92 (m, 24H, ar), 5.22-5.15 (m, 2H), 5.09-5.03 (m, 1H), 4.81 (app. d, J=11.9, 1H), 4.76-4.68 (m, 2H, anomeric), 4.63-4.56 (m, 2H), 4.54-4.46 (m, 4H), 3.89 (app. t, J=9.4, 1H), 3.84-3.78 (m, 1H), 3.62-3.45 (m, 4H), 3.38-3.18 (m, 3H), 2.66-2.53 (m, 2H), 2.43-2.29 (m, 2H), 2.13 (s, 3H, Lev CH$_3$), 1.66-1.48 (m, 4H, linker), 1.38-1.27 (m, 2H, linker); $^{13}$C-NMR (100 MHz, CDCl$_3$) δ 206.3 (Lev carbonyl), 171.6, 138.2, 138.1, 138.0, 131.4, 129.6, 129.4, 128.7, 128.5, 128.3, 128.1, 128.03, 127.99, 127.9, 127.6, 127.4, 121.3, 96.9 (anomeric), 79.8, 79.6, 74.3, 73.7, 73.2, 70.9, 69.0, 68.9, 68.3, 67.3, 37.8, 29.9 (Lev CH$_3$), 29.2, 28.0, 23.6; HRMS (MALDI-TOF): Calcd for C$_{52}$H$_{58}$BrNO$_{10}$Na$^+$ [M+Na]$^+$ 958.3134. found 958.3112.

N-(Benzyl)benzyloxycarbonyl-5-amino-pentanyl 2,6-di-O-benzyl-3-O-(4-bromo)benzyl-1-thio-β-D-glucopyranoside (44)

To a solution of 43 (140 mg, 0.15 mmol) in DCM (5.0 ml) hydrazine hydrate (26 μl, 0.54 mmol) dissolved in AcOH (0.4 ml) and pyridine (0.6 ml) was added and the solution stirred for 1 h. The reaction was then quenched by the addition of acetone and concentrated. Column chromatography on silica gel (hexanes/ethyl acetate) afforded 44 (102 mg, 0.12 mmol, 81%). [α]$_D^{20}$=+24.3° (c=4.2, CHCl$_3$), IR ν$_{max}$ (film) 3454, 3031, 2920, 1696, 1454, 1422, 1229, 1055 cm$^{-1}$; $^1$H-NMR (400 MHz, CDCl$_3$) δ 7.48-7.04 (m, 24H, Ar), 5.16-5.09 (m, 2H), 4.86 (app. d, J=11.7, 1H), 4.70-4.43 (m, 8H), 3.75-3.55 (m, 6H), 3.45 (app. dd, J=9.5, 3.6, 1H), 3.32-3.14 (m, 3H), 1.59-1.44 (m, 4H, linker), 1.33-1.23 (m, 2H, linker); $^{13}$C-NMR (100 MHz, CDCl$_3$) δ 138.3, 138.1, 138.0, 131.6, 129.5, 128.6, 128.52, 128.47, 128.02, 127.98, 127.9, 127.8, 127.7, 127.4, 121.6, 96.9 (anomeric), 81.7, 79.8, 74.6, 73.7, 72.9, 71.4, 70.1, 69.8, 68.1, 67.3, 50.4, 47.3, 29.2, 27.7, 23.7; HRMS (MALDI-TOF): Calcd for C$_{47}$H$_{52}$BrNO$_8$Na$^+$ [M+Na]$^+$ 860.2769. found 860.2508.

N-(Benzyl)benzyloxycarbonyl-5-amino-pentanyl 2,3-di-O-benzoyl-4-O-benzyl-α-L-rhamnopyranosyl-(1→3)-2-O-benzoyl-4,6-O-benzyl-β-D-glucopyranosyl-(1→4)-2,6-di-O-benzyl-3-O-(4-bromo)benzyl-α-D-glucopyranoside (45)

Disaccharide 41 (144 mg, 0.13 mmol) and glucoside 44 (102 mg, 0.12 mmol) were coevaporated with toluene three times and dried in vacuo. The mixture was dissolved in DCM (4 ml) and NIS (36 mg, 0.16 mmol) was added and cooled to −20° C. TfOH (1.4 μl, 16 μmol) was added and the mixture was stirred and warmed up to 0° C. in two hours. The reaction was quenched by the addition of aqueous Na$_2$S$_2$O$_3$ and saturated aqueous NaHCO$_3$. The phases were separated and the aqueous phase was extracted with DCM. The combined organic phases were dried over MgSO$_4$, filtered and concentrated. The crude product was purified by column chromatography on silica gel (hexanes/ethyl acetates) to afford 45 (200 mg, 0.12 mmol, 95%). [α]$_D^{20}$=+36.9° (c=5.2, CHCl$_3$), IR ν$_{max}$ (film) 3031, 2866, 1730, 1698, 1602, 1452, 1262, 1092 cm$^{-1}$; $^1$H-NMR (400 MHz, CDCl$_3$) δ 8.31-6.72 (m, 54H, Ar), 5.73 (app. dd, J=9.4, 3.4, 1H), 5.44 (app. dd, J=3.4, 1.9, 1H), 5.37 (app. dd, J=9.3, 8.1, 1H), 5.21 (bs, 2H), 5.17-5.09 (m, 2H), 4.88 (app. d, J=10.9, 1H), 4.76-4.39 (m, 13H), 4.31 (app. d, J=12.2, 1H), 4.19 (app. dd, J=9.5, 6.1, 1H), 4.03-3.63 (m, 9H), 3.49-3.42 (m, 3H), 3.37-3.15 (m, 4H), 1.59-1.40 (m, 4H), 1.28-1.11 (m, 5H); $^{13}$C-NMR (100 MHz, CDCl$_3$) δ 165.2, 164.6, 164.5, 138.9, 138.5, 138.2, 138.0, 137.89, 137.87, 137.6, 133.1, 133.0, 132.9, 131.1, 129.9, 129.8, 129.7, 129.63, 129.59, 129.4, 129.2, 128.7, 128.6, 128.5, 128.43, 128.35, 128.3, 128.24, 128.19, 128.14, 128.08, 128.0, 127.90, 127.89, 127.74, 127.67, 127.61, 127.55, 127.3, 120.7, 100.3 (anomeric), 97.7 (anomeric), 96.9 (anomeric), 80.3, 79.1, 78.0, 77.4, 76.7, 75.6, 75.2, 74.9, 74.8, 74.5, 73.6, 73.5, 73.1, 71.9, 71.1, 69.7, 68.8, 68.3, 68.0, 67.7, 67.2, 29.0, 23.3, 17.9 (Rha CH$_3$); HRMS (MALDI-TOF): Calcd for C$_{101}$H$_{102}$BrNO$_{20}$Na$^+$ [M+Na]$^+$ 1750.6071. found 1759.5921.

5-Amino-pentanyl α-L-rhamnopyranosyl-(1→3)-β-D-glucopyranosyl-(1→4)-α-D-glucopyranoside (37)

To a solution of protected trisaccharide 45 (61 mg, 35 μmol) in THF (2 ml) NaOMe (0.5 M in MeOH, 0.5 ml) was added and stirred for 4 h. The mixture was neutralized with Amberlite IR 120 (H$^+$) ion exchange resin, filtered and concentrated. The crude product was dissolved in a mixture of THF (5.0 ml) MeOH (2.5 ml), H$_2$O (2.0 ml) and AcOH (0.5 ml). The solution was purged with Ar, then 10% Pd/C (100 mg) was added and the solution purged with H$_2$ for 30 min, then stirred under an H$_2$ atmosphere for 12 h, filtered and concentrated. Purification by RP SPE (Waters Sep-Pak®, C18) afforded 37 (12.5 mg, 30 μmol, 75%). 1H-NMR (600 MHz, D$_2$O) δ 5.21 (s, 1H, anomeric Rha), 4.99 (d, J=2.9, 1H, anomeric α-Glc), 4.61 (d, J=8.0, 1H, anomeric β-Glc), 4.15-4.05 (m, 2H), 4.02-3.97 (m, 2H), 3.93-3.79 (m, 6H), 3.73-3.66 (m, 3H), 3.64-3.49 (m, 5H), 3.09 (t, J=7.1, 2H), 1.81-1.71 (m, 4H, linker), 1.59-1.50 (m, 2H, linker), 1.33 (d, J=6.0, 3H, Rha CH$_3$); $^{13}$C-NMR (150 MHz, D$_2$O) δ 102.9 (anomeric Rha), 101.7 (anomeric β-Glc), 98.4 (anomeric α-Glc), 82.7, 79.7, 76.5, 74.5, 72.6, 72.4, 71.6, 71.1, 71.0, 70.8, 69.4, 68.6, 68.5, 61.2, 60.6, 40.0, 28.6, 27.1, 23.0, 17.1. (Rha CH$_3$);

HRMS (MALDI-TOF): Calcd for $C_{23}H_{43}BrNO_{15}Na^+$ [M+Na]$^+$ 596.2525. found 596.2540.

N-(Benzyl)benzyloxycarbonyl-5-amino-pentanyl 2,3-di-O-benzoyl-4-O-benzyl-α-L-rhamnopyranoside (46)

Rhamnoside-imidate (127 mg, 0.20 mmol) and 5-aminopentanol (160 mg, 0.49 mmol) were coevaporated with toluene three times, dried in vacuo and dissolved in anhydrous DCM (3 ml). Freshly activated molecular sieves (4 Å) were added and the mixture cooled to −30° C. TMSOTf (3.6 µl, 20 µmol) was added and the reaction was warmed to −20° C. over 1 h. The reaction was quenched with TEA and concentrated. Column chromatography on silica gel (hexanes/ethyl acetate) afforded 46 (145 mg, 0.19 mmol, 94%). $[α]_D^{20}$=+54.1° (c=2.6, CHCl$_3$), IR $ν_{max}$ (film) 2963, 1727, 1260, 1018 cm$^{-1}$; $^1$H-NMR (400 MHz, CDCl$_3$) δ 8.28-7.00 (m, 25H, Ar), 5.73 (app. dd, J=9.6, 3.4, 1H), 5.59 (bs, 1H), 5.19 (app d, J=11.3, 2H), 4.87 (bs, 1H, anomeric), 4.68 (app. dd, J=28.1, 10.9, 2H), 4.53 (bs, 2H), 3.96 (bs, 1H), 3.79 (app. t, J=9.5, 1H), 3.75-3.61 (m, 1H), 3.48-3.21 (m, 3H), 1.65-1.51 (m, 4H), 1.45-1.27 (m, 5H); $^{13}$C-NMR (100 MHz, CDCl$_3$) δ 165.6, 165.5, 138.1, 137.8, 133.4, 133.2, 130.0, 129.9, 129.7, 128.7, 128.6, 128.47, 128.46, 128.2, 127.99, 127.95, 127.4, 97.5 (anomeric), 79.3, 75.3, 72.6, 71.5, 68.0, 67.8, 67.3, 29.3, 23.6, 18.3; HRMS (MALDI-TOF): Calcd for $C_{47}H_{49}NO_9Na^+$ [M+Na]$^+$ 794.3300. found 794.3264.

5-Amino-pentanyl α-L-rhamnopyranoside (39)

To a solution of protected rhamnoside 46 (145 mg, 0.19 mmol) in THF (4 ml) NaOMe (0.5 M in MeOH, 0.5 ml) was added and stirred for 4 h. The mixture was neutralized with Amberlite IR 120 (H$^+$) ion exchange resin, filtered and concentrated. The crude product was dissolved in a mixture of THF (10 ml) MeOH (5 ml), H$_2$O (4 ml) and AcOH (1 ml). The solution was purged with Ar, then 10% Pd/C (300 mg) was added and the solution purged with H$_2$ for 30 min, then stirred under an H$_2$ atmosphere for 12 h, filtered and concentrated. Purification by RP SPE (Waters Sep-Pak®, C18) afforded 39 (44 mg, 0.18 mmol, 94%). $^1$H-NMR (600 MHz, D$_2$O) δ 4.85 (s, 1H, anomeric Rha), 4.01-3.96 (m, 1H), 3.81-3.70 (m, 3H), 3.62-3.57 (m, 1H), 3.50 (app. t, J=9.6, 1H), 3.11-3.03 (m, 2H), 1.78-1.67 (m, 4H, linker), 1.56-1.46 (m, 2H), 1.34 (d, J=6.3, 3H, Rha CH$_3$)$^{13}$C-NMR (150 MHz, D$_2$O) δ 98.3 (anomeric), 70.6, 70.0, 68.8, 67.1, 66.1, 38.0, 26.6, 25.1, 21.0, 15.2 (Rha CH$_3$); HRMS (MALDI-TOF): Calcd for $C_{11}H_{23}NO_5Na^+$ [M+Na]$^+$ 272.1468. found 272.1433.

EXAMPLE 3

Preparation and Characterization of an Pentasaccharide-Protein Conjugate

Polysaccharide vaccines provoke exclusively a T-cell independent immune response and do not induce an immunoglobulin class switch. The synthetic repeating unit 1 of the *Clostridium difficile* glycopolymer PS-I was conjugated to the protein carrier Crm$_{197}$. The detoxified diphtheria toxoid Crm$_{197}$ was chosen as a carrier since it is an approved constituent of licensed vaccines (Barocchi et al. (2007), Vaccine 25, 2963-73).

Conjugations

Figure 2A:
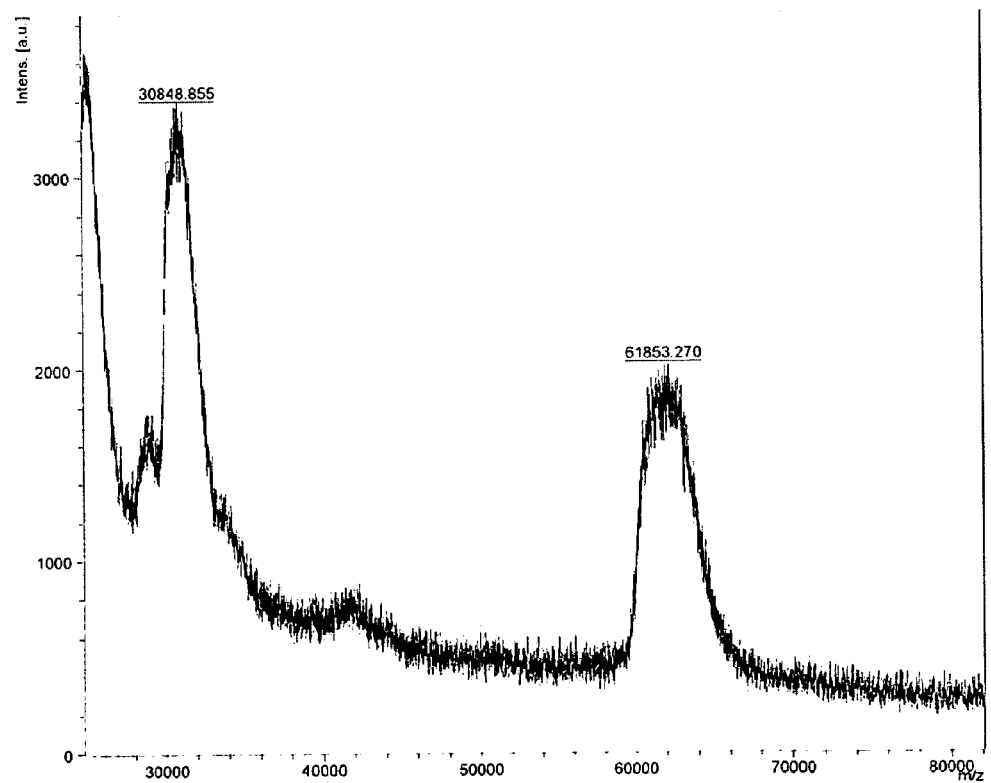
Figure 2B:
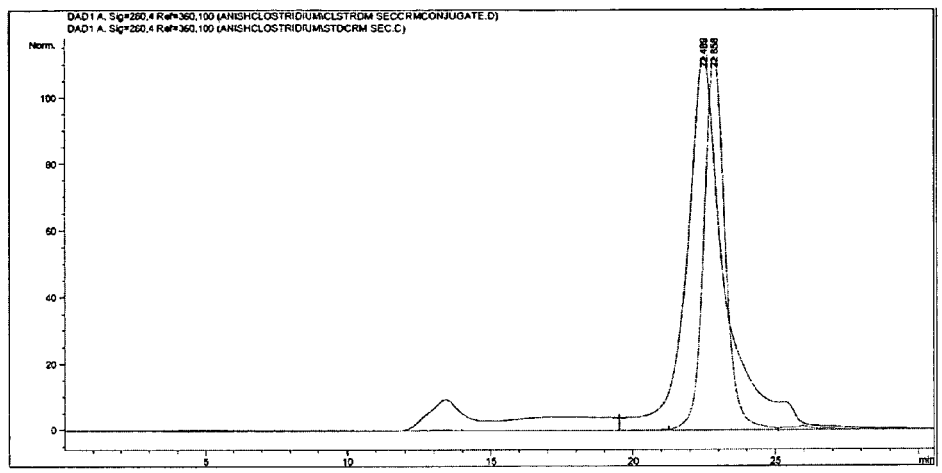
Figure 2C:

A) To a solution of Di(N-succinimidyl) adipate (5.8 mg, 17 µmol) in DMSO (250 µl) and NEt$_3$ (20 µl) pentasaccharide 1 (500 µg, 0.57 µmol) dissolved in DMSO (250 µl) was added dropwise. The solution was stirred for 2 h, diluted with phosphate buffer (1.0 ml, 100 µM, pH 7.5) and extracted with CHCl$_3$. CRM$_{197}$ (rDNA) (250 µl, 250 µg, Pfenex Inc (USA)) was added to the aqueous layer and stirred for 5 h. Conjugate 1a was desalted and concentrated. An average load of 3.6 pentasaccharide units per protein was determined by MALDI-TOF MS, SEC-HPLC and SDS PAGE confirmed modification of the protein (FIG. 2). SEC-HPLC $t_R$=22.49 min, MS (MALDI-TOF) found 61853 Da.

Figure 3:
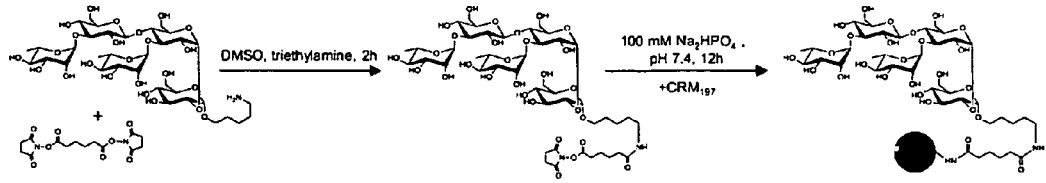

B) First, the primary amine group of the linker moiety of PS-I pentasaccharide 1 was reacted with one of the ester groups of the spacer molecule di(N-succinimidyl) adipate in water-free DMSO (12.7 mg in 120 µl) in the presence of 10 µl triethylamine at room temperature over 2 hours, with the spacer used in 10-fold molar excess to avoid dimer formation. After addition of 400 µL 0.1 M Na-phosphate buffer, pH 7.4, unreacted spacer molecules were removed by chloroform extraction. The remaining ester group of the spacer moiety was then reacted with the ε-amino groups of lysine residues on the CRM$_{197}$ protein (Pfenex) in 0.1 M Na-phosphate buffer, pH 7.4, at room temperature over 12 hours (FIG. 3). For one reaction, 3 mg of PS-I pentasaccharide and 1 mg of CRM$_{197}$ (solubilized in 1 mL 0.1 M Na-phosphate buffer, pH 7.4) was used. The resulting conjugate was purified by ultrafiltration (10 kDa, Amicon, Millipore) with deionized water. The protein concentration was determined by bicinchoninic acid (BCA) assay (Pierce).

Figure 4A:
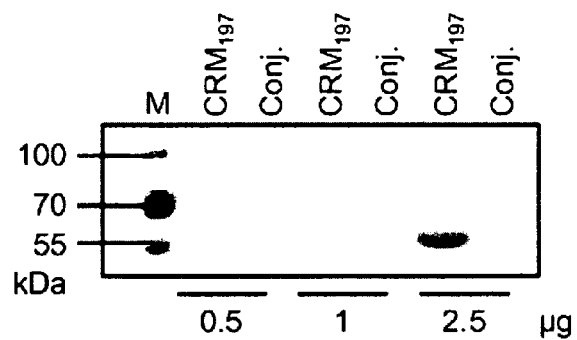

Successful conjugation was confirmed by SDS-PAGE as shown in FIG. 4a. Marker M is PageRuler Plus Prestained Protein Ladder (Thermo Scientific). Conjugate samples are shifted towards higher masses compared with unconjugated CRM$_{197}$.

Figure 4B:
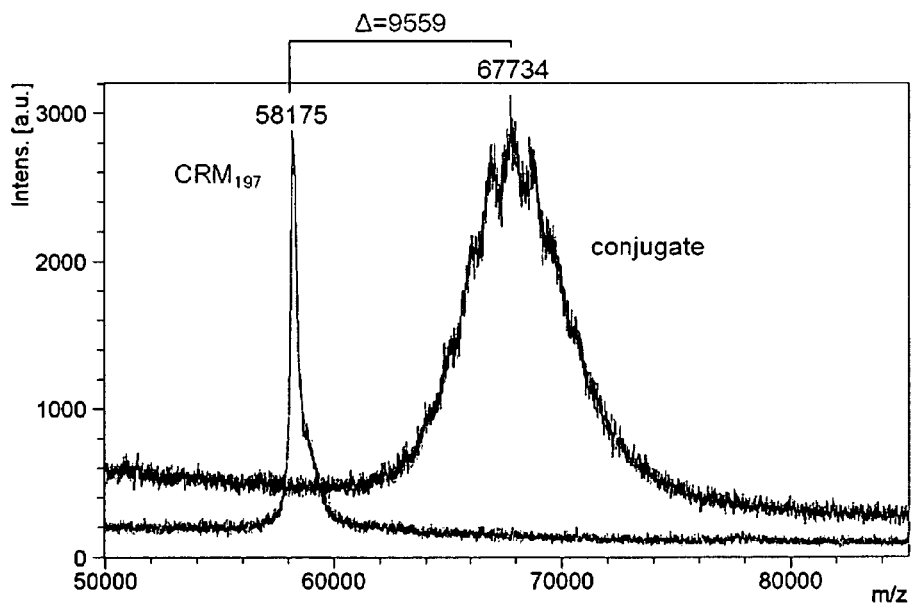

The oligosaccharide/CRM$_{197}$ ratio was determined by MALDI-TOF MS. The mass analysis of CRM$_{197}$ yielded a m/z ion at 58.2 kDa. The mass analysis of the conjugate yielded a major m/z ion at 67.7 kDa and further peaks ~1000 Da apart, corresponding to conjugates of different valencies (FIG. 4b). An average of 9.6 PS-I pentasaccharide 1 molecules were loaded on one CRM$_{197}$ protein, resulting in conjugate 1b.

Knowing the protein concentration of the conjugate, as determined by bicinchoninic acid (BCA) assay, and the average sugar loading, the carbohydrate content was calculated to 300±46 µg/mL (mean±SD) and verified by colorimetric anthrone assay (302±76 µg/mL), an approved method for the carbohydrate determination of the licensed pneumococcal conjugate vaccine Prevenar (Pfizer).

SDS-PAGE

Pentasaccharide 1-CRM$_{197}$ conjugate and unconjugated CRM$_{197}$ were dissolved in Lämmli buffer (0.125 M Tris, 20% (v/v) glycerol, 4% (w/v) SDS, 5% (v/v) beta-mercaptoethanol, bromophenol, pH 6.8) and boiled at 95° C. for 5 minutes. Samples were run in 10% polyacrylamide gels and stained with 0.025% (w/v) Coomassie Brilliant blue R-250 in an aqueous solution containing 40% (v/v) methanol and 7% (v/v) acetic acid.

MALDI-TOF Mass Spectrometry

Conjugation was confirmed by matrix-assisted laser desorption/ionization-time of flight mass spectrometry (MALDI-TOF MS) using an Autoflex™ Speed instrument (Bruker Daltonics, Bremen, Germany). The mass spectrometer was operated in positive linear mode. Spectra were acquired over an m/z range from 50,000 to 85,000 Da and data was analyzed with the FlexAnalysis software provided with the instrument. 2',4'-dihydroxyacetonephenone (DHAP) was used as matrix, samples were spotted using the dried droplet technique.

Anthrone Assay

Anthrone assays were performed in 96-well format in a modified assay according to Leyva et al., *Biologicals* 36:134-141, 2008. Briefly, 75 μL of anthrone reagent (0.1% (w/v) in concentrated sulfuric acid) was added to each well of a 96-well microtiter plate containing 25 μL of standard solutions, sample dilutions and blank. Plates were first placed at 4° C. for 10 minutes, then incubated at 100° C. for 20 minutes, and cooled down at room temperature for 20 minutes. Absorbance at 579 nm was determined in a microplate reader. Colorimetric response was compared to a standard curve based on glucose and rhamnose in a 3:2 molar ratio.

EXAMPLE 4

Immunization and Monoclonal Antibodies

Figure 5:
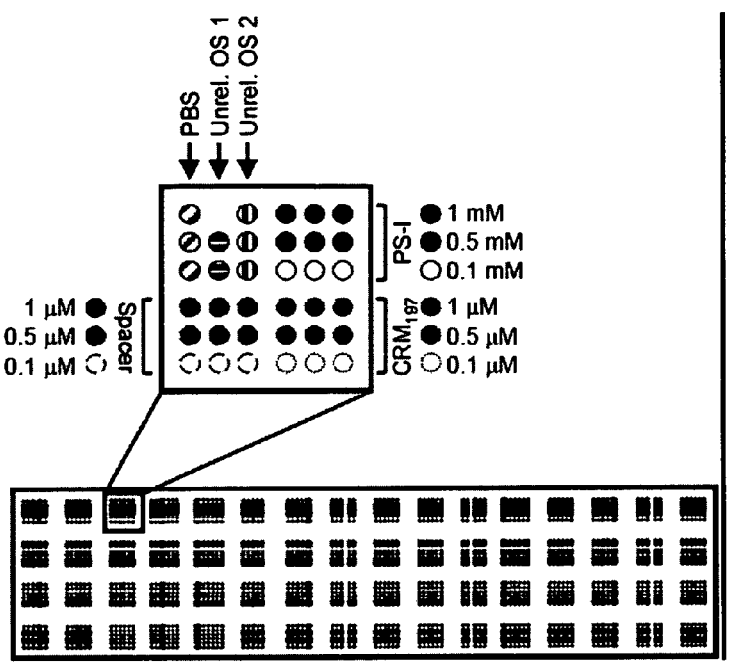

To test the immunogenicity of the PS-I pentasaccharide hapten, three groups of six female C57BL/6 mice each were immunized subcutaneously (s.c.) with conjugate (one group without adjuvant, one group with Freund's adjuvant, one group with Alum adjuvant). Each mouse received an amount of conjugate corresponding to 3 μg PS-I pentasaccharide 1 antigen. Initial immunizations (priming) was followed by an immunization after two weeks (boosting). Sera were collected in one-week intervals. IgG antibody responses were evaluated by microarray. PS-I pentasaccharide 1 in three different concentrations (1, 0.5 and 0.1 mM), $CRM_{197}$ (1, 0.5 and 0.1 μM) and bovine serum albumin (BSA)-spacer-GlcNAc conjugate (1, 0.5 and 0.1 μM) were spotted in triplicate onto the surface of the microarray slides (N-hydroxysuccinimid ester-activated glass slides (CodeLink)) as shown in FIG. 5. BSA-spacer-GlcNAc was used to assess immunogenicity against the spacer moiety of the conjugate. As negative controls, phosphate-buffer saline (PBS), as well as two unrelated oligosaccharides (both at a concentration of 1 mM) were also included. Microarrays were designed such that high-throughput analysis of 64 samples per array was possible.

PS-I pentasaccharide-specific IgG antibody responses were identified in pooled sera of three groups (each n=6) of immunized mice after priming, and more pronounced after boosting (week 3), as determined by microarray analysis (FIG. 6).

IgG antibody responses were quantified by determination of the fluorescence intensity values using the sera of individual mice. While the conjugate already showed immunogenicity without adjuvant (FIG. 7, left diagram, white bars), IgG titers against PS-I pentasaccharide were markedly increased when Freund's adjuvant was used (light grey bars), and, more pronounced, with Alum adjuvant (dark grey bars). IgG antibody titers against the carrier protein $CRM_{197}$ were lower in mice immunized without adjuvant than in mice immunized with Freund's and Alum adjuvant (FIG. 7, central diagram). There was no IgG response against the spacer moiety in mice immunized without adjuvant, but in mice immunized with Freund's and Alum adjuvants (FIG. 7, right diagram).

As an IgG-specific detection antibody, Anti-Mouse IgG (whole molecule)-FITC (Sigma) was used in the tests of FIGS. 6 and 7. Slides were analyzed on a GenePix Pro 4300A microarray scanner and data was analyzed using the GenePix Pro 7 software (both Molecular Devices). Individual mice sera at week 0 ('preblee'), week 2 ('prime') and week 3 ('boosted') were analyzed by microarray (FIG. 6). Total fluorescence intensity values were determined with the GenePix Pro 7 software and background fluorescence (PBS) was subtracted for each value. Data shown is mean±S.E.M. (standard error of the mean) for n=6 values. "Unrel. OS" in FIG. 5 means unrelated oligosaccharide.

To get an insight into the subclasses of IgG antibodies raised against PS-I pentasaccharide, microarray analysis with pooled sera using subclass-specific detection antibodies against IgG1, IgG2a and IgG3 was performed.

Figure 8:
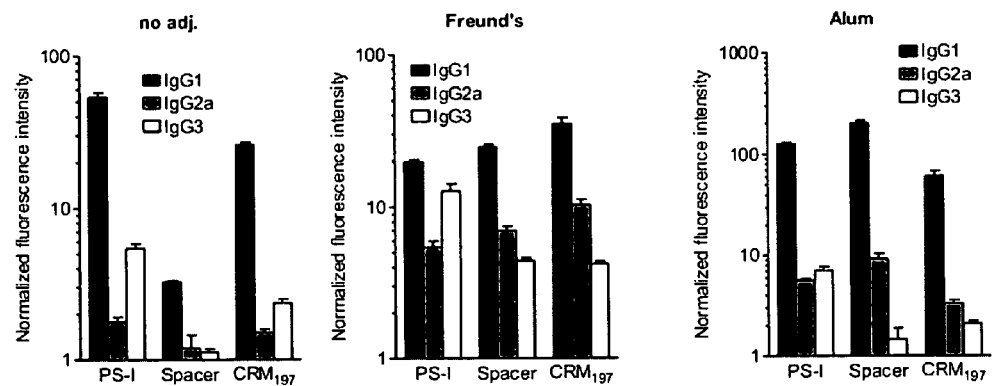

FIG. 8 shows the isotype analysis of the IgG immune response by microarray. Pooled sera at a 1:100 dilution were analyzed with isotype-specific detection antibodies (anti-IgG1, Invitrogen A21125; anti-IgG2a, Invitrogen A21241; anti-IgG3, Invitrogen A21151). Data shown is mean, n=6, S.E.M., normalized to background fluorescence intensity, of mice after boosting (week 3).

As evident from FIG. 8, while antibodies against PS-I are almost exclusively of the IgG1 subtype in mice immunized with conjugate without adjuvant (left panel) or Alum adjuvant (right panel), mice immunized with Freund's adjuvant show a relatively high proportion of antibodies of the IgG2a and IgG3 subclasses in addition to IgG1. IgG3 and IgG2a are mainly induced by T-cell independent antigens such as polysaccharides, while IgG1 is mainly T-cell dependent and directed against protein antigens.

Figure 9:
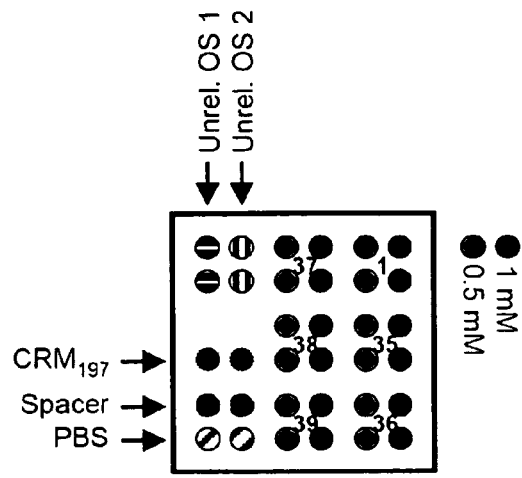

To assess whether antibodies raised with PS-I pentasaccharide antigen 1 recognize substructures of the antigen as well, which allows to define the minimal epitope, microarray slides with substructures 35-39 in addition to 1 were prepared (FIG. 9). $CRM_{197}$, BSA-spacer-GlcNAc were included as well as two unrelated oligosaccharides and PBS as negative controls. This array was used to assess immune responses in pooled sera of the three groups of mice immunized with conjugate.

FIG. 10 shows the deletion sequence analysis of the immune response of mice immunized with glycoconjugate without adjuvant. Pooled sera of mice (n=6) were analyzed on deletion sequence microarray as in FIG. 9, using Alexa Fluor 635 goat anti-mouse IgG (Invitrogen) as detection antibody. Unrel. OS, unrelated oligosaccharide.

FIG. 11 shows the deletion sequence analysis of the immune response of mice immunized with glycoconjugate and Freund's adjuvant.

FIG. 11 shows the deletion sequence analysis of the immune response of mice immunized with glycoconjugate and Alum adjuvant.

As shown in FIGS. 10 and 11, sera of mice immunized without adjuvant or with Freund's adjuvant contain antibodies against substructure with rhamnose, while the IgG responses against disaccharide 38 is generally higher than those against trisaccharide 37, albeit 37 is closer to the original PS-I pentasaccharide antigen 1 used for immunization. The IgG antibody response in mice immunized with Alum adjuvant shows a more specific reactivity against the PS-I pentasaccharide with lower titers against deletion sequences 38 and 37 (FIG. 12). No antibody response against oligoglucose disaccharide 35 nor trisaccharide 36 was detected in any of the groups. Disaccharide 38 may be the minimal epitope of the PS-I pentasaccharide.

Monoclonal antibodies were generated with the traditional hybridoma technique [Köhler and Milstein, 1975]. Three monoclonal antibodies (mAbs), 2C5, 10A1 and 10D6, were selected for evaluation with deletion sequence microarray and isotype-specific detection antibodies. All three mABs showed identical patterns on the microarray, exclusively bound to PS-I pentasaccharide 1 but none of the substructures, and were of the IgG1 subtype (FIG. 13).

Figure 13:
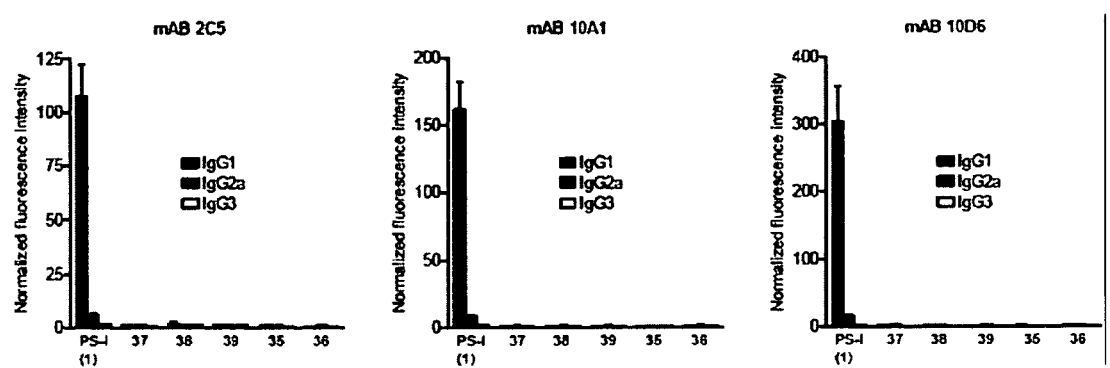

FIG. 13 shows different monoclonal antibodies against PS-I. One mouse of the Alum group was subjected to a second boosting immunization (s.c.) at week 5 and three final boostings (intraperitoneal, i.p.) at three consecutive days in week 7. One day after final boosting, the mouse was sacrificed, the spleen was removed and subjected to monoclonal antibody development. After three rounds of subcloning, supernatants of three monoclonal antibodies (mAB)-producing clones, 2C5, 10A1 and 10D6, were subjected to isotype analysis as in FIG. 8, using hybridoma supernatants in a 1:3125 dilution.

Immunizations

Six to eight-weeks old female C57BL/6 mice were immunized s.c. with conjugate corresponding to 3 μg PS-I pentasaccharide 1 with Freund's (priming immunizations with Freund's Complete Adjuvant, boosting immunizations with Freund's Incomplete Adjuvant, both Sigma) or Aluminium Hydroxide Gel Adjuvant (Brenntag Biosector, Frederikssund, Denmark), or without adjuvant. Mice received boosting injections after 2 weeks. For all immunizations, antigen was diluted in sterile PBS to a total injection volume of 100 μL per mouse. Blood was collected in one-week intervals via the tail vein and erythrocytes separated from serum by centrifugation. Serum serum antibody responses were analyzed by microarray. One mouse of the Alum group received a second boosting injection s.c. at week 5 after first immunization, and, prior to being sacrificed, three final boosting injections via the intraperitoneal (i.p.) route, on three consecutive days at week 7.

Preparation of Microarrays

Oligosaccharides bearing an amine linker, or proteins, were dissolved in sodium phosphate buffer (50 mM, pH 8.5) and printed robotically using a piezoelectric spotting device (S11, Scienion, Berlin, Germany) onto NHS-activated glass slides (CodeLink). Slides were incubated in a humid chamber to complete reaction for 24 hours and stored in an anhydrous environment. Prior to the experiment, remaining succinimidyl groups were quenched by incubating slides in 100 mM ethanolamine in sodium phosphate buffer (pH 9, 50 mM) for 1 hour at 50° C. Slides were rinsed three times with deionized water and dried by centrifugation.

Microarray Binding Assays

The quenched array slides were blocked for 1 hour with 1% (w/v) BSA in PBS, then washed three times with PBS and dried by centrifugation. A FlexWell 64 (Grace Bio-Labs, Bend, Oreg., USA) grid was applied to the slides. Resulting 64 wells were used for 64 individual experiments. Slides were incubated with sera dilutions or hybridoma supernatants (all dilutions were prepared with PBS) for 1 hour at room temperature in a humid chamber, washed three times with PBS-Tween-20 (0.1% v/v) and dried by centrifugation. Then, slides were incubated with fluorescence-labeled detection antibody diluted in 1% BSA in PBS (w/v) for 1 hour at room temperature in a humid chamber. Slides were washed three times with PBS-Tween-20 (0.1% v/v) and rinsed once with deionized water and dried by centrifugation. Slides were scanned with a GenePix 4300A scanner (Molecular Devices) using the GenePix Pro 7 software. Detection antibodies used were Anti-Mouse IgG (whole molecule)-FITC (Sigma), Alexa Fluor 635 Goat Anti-Mouse IgG (H+L) (Life Technologies) and Alexa Fluor 594 Goat Anti-Mouse IgG1 (γ1) (Life Technologies) in 1:400 dilutions, as well as Alexa Fluor 647 Goat Anti-Mouse IgG2a (γ2a) and Alexa Fluor 488 Goat Anti-Mouse IgG3 (γ3) (Life Technologies) in 1:200 dilutions.

Monoclonal Antibodies

Monoclonal antibodes (mABs) were generated using the standard method by Köhler and Milstein, 1975. Briefly, spleenocytes of one mouse were fused with $10^8$ mouse myeloma cells in the presence of 50% PEG 1500. Fused cells were selected with complete growth medium (IMDM supplemented with 10% heat-inactivated fetal calf serum, 2 mM L-glutamine, 24 μM beta-mercaptoethanol, 100 μM hypoxanthine, 16 μM thymidine, non-essential amino acids, 100 U/mL penicillin, 100 μg/mL streptomycin, 50 μg/mL gentamycin, 10% hybridoma cloning supplement (BM Condimed H1, Roche)) with 0.4 μM aminopterin. Cells were maintained at 37° C. at 5% $CO_2$. Hybridoma cells were subjected to three consecutive subcloning steps by limited dilution. Clones producing antibodies against PS-I pentasaccharide were identified by microarray analysis.

The invention claimed is:

1. A method for preparing a pentasaccharide having the sequence α-L-Rhap-(1→3)-β-D-Glcp-(1→4)-[α-L-Rhap-(1→3)]-α-D-Glcp-(1→2)-α-D-Glcp and represented by structure 1 or 1'

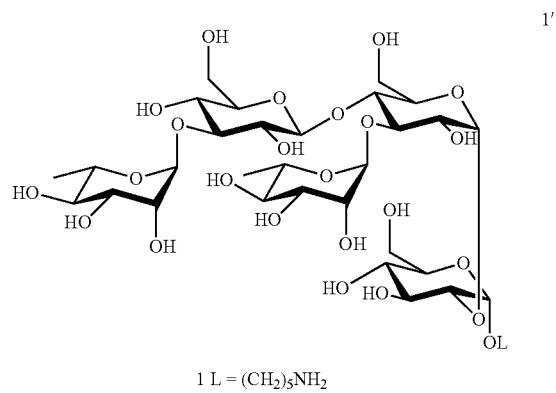

1 L = $(CH_2)_5NH_2$ or a derivative thereof in which at least one hydroxyl group thereof is substituted by at least one other functional group or atom, said method comprising
a) assembling a monosaccharide building block 2', wherein the specific protected amino linker of building block 2 is replaced by a different protected or unprotected linker L, and building blocks 3 or 4 to yield the corresponding disaccharide 21', reacting the disaccharide 21' with building block 4 to form the trisaccharide 23', subjecting the trisaccharide 23' to a bis-glycosylation reaction with 2 molecules of building block 5 to yield the corresponding fully protected pentasaccharide 24' and finally, after deprotection, to yield pentasaccharide 1', wherein the specific amino linker of pentasaccharide 1 is replaced by a different linker L, or
b) assembling a monosaccharide building block 2', wherein the specific protected amino linker of building block 2 is replaced by a different protected or unprotected linker L, and building block 27 to yield the corresponding disaccharide 30', reacting the disaccharide 30' with building block 4 or 29 to form the corresponding protected trisaccharide 32', deprotecting the trisaccharide 32' to obtain trisaccharide 33', subjecting the trisaccharide 33' to a bis-glycosylation reaction with 2 molecules of building block 5 to yield the corresponding fully protected pentasaccharide 34' and finally, after deprotection, to yield pentasaccharide 1', wherein the specific amino linker of pentasaccharide 1 is replaced by a different linker L,
wherein the different linker L is $(CH_2)_n NH_2$, with n being an integer from 2 to 50, and where 2, 2', 3, 4, 5, 21', 23', 24', 27, 29, 30', 32', 33', 34' are defined as follows:

51 52
-continued
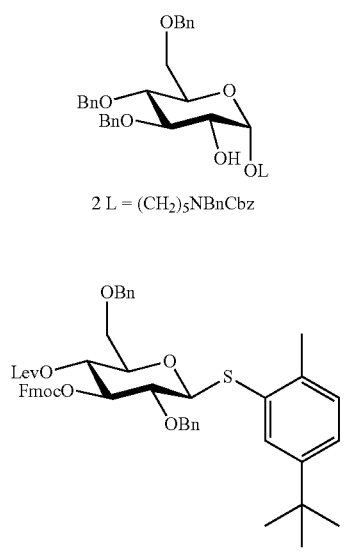
2 L = (CH₂)₅NBnCbz
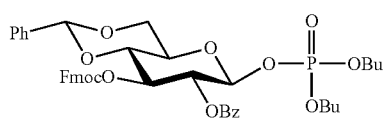
3
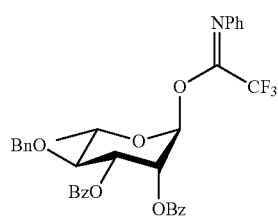
4
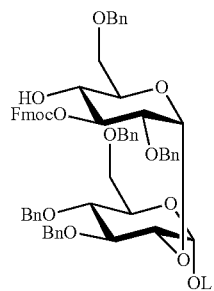
5
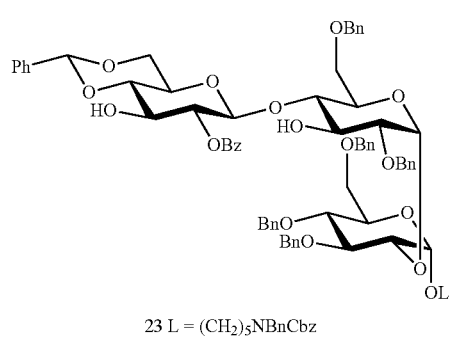
21 L = (CH₂)₅NBnCbz
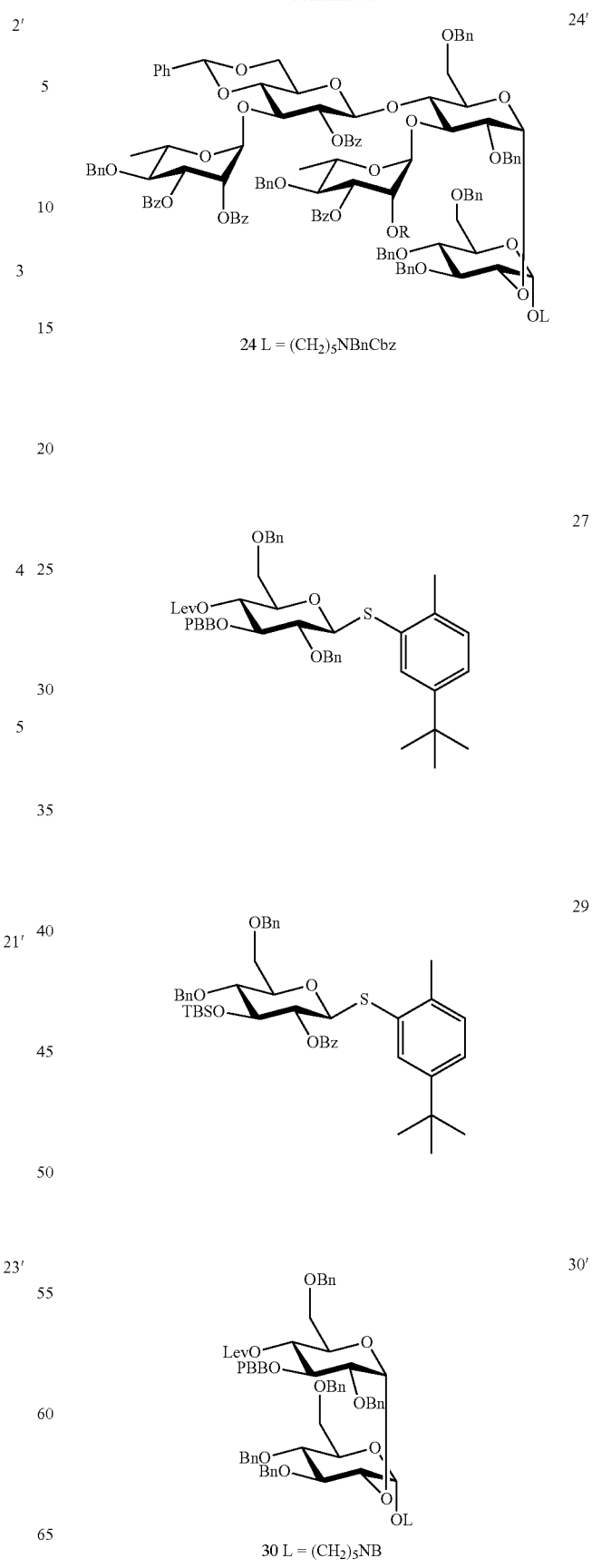

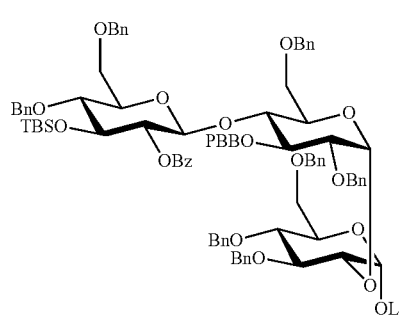
32 L = (CH₂)₅NBnCbz
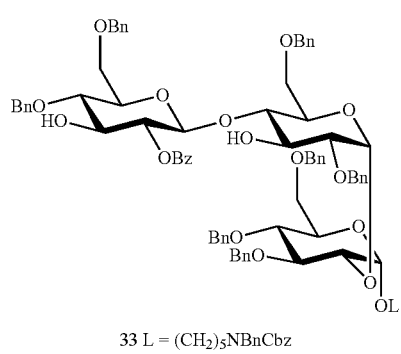
33 L = (CH₂)₅NBnCbz
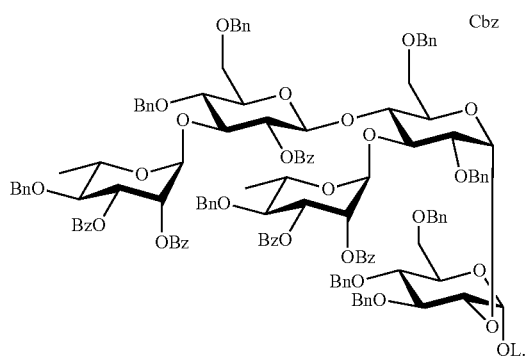
34 L = (CH₂)₅NBnCbz
2. The method according to claim 1, wherein the different linker L of pentasaccharide 1' is $(CH_2)_n NH_2$, with n being an integer from 3 to 10.
\* \* \* \* \*